US007863450B2

(12) United States Patent
Celanire et al.

(10) Patent No.: US 7,863,450 B2
(45) Date of Patent: *Jan. 4, 2011

(54) COMPOUNDS COMPRISING AN OXAZOLINE OR THIAZOLINE MOIETY, PROCESSES FOR MAKING THEM, AND THEIR USES

(75) Inventors: Sylvain Celanire, Feigeres (FR); Patrice Talaga, Watermael-Boitsfort (BE); Regorius Leurs, Amsterdam (NL); Frederic Denonne, Brussels (BE); Henkdrik Timmerman, Oegstgeest (NL); Florence Lebon, Lillois (BE)

(73) Assignee: UCB Pharma, S.A., Brussels (BE)

( * ) Notice: Subject to any disclaimer, the term of this patent is extended or adjusted under 35 U.S.C. 154(b) by 664 days.

This patent is subject to a terminal disclaimer.

(21) Appl. No.: 11/910,153

(22) PCT Filed: Mar. 29, 2006

(86) PCT No.: PCT/EP2006/002860

§ 371 (c)(1),
(2), (4) Date: Sep. 28, 2007

(87) PCT Pub. No.: WO2006/103057

PCT Pub. Date: Oct. 5, 2006

(65) Prior Publication Data

US 2008/0161331 A1  Jul. 3, 2008

(30) Foreign Application Priority Data

Mar. 31, 2005 (EP) .................................. 05006971

(51) Int. Cl.
C07D 211/68 (2006.01)
C07D 401/00 (2006.01)
A61K 31/445 (2006.01)

(52) U.S. Cl. ..................... 546/194; 546/209; 514/319
(58) Field of Classification Search ................. 546/194, 546/209; 514/319
See application file for complete search history.

(56) References Cited

U.S. PATENT DOCUMENTS

| 4,843,087 | A | 6/1989 | Diana |
| 5,260,261 | A | 11/1993 | Prisbylla |
| 5,525,599 | A | 6/1996 | Lin |
| 6,436,939 | B2 | 8/2002 | Carruthers et al. |
| 7,790,720 | B2 * | 9/2010 | Celanire et al. .......... 514/236.8 |

FOREIGN PATENT DOCUMENTS

| FR | 2 673 626 | 11/1992 |
| JP | 10-316617 | 12/1998 |
| WO | WO 93/00359 | 1/1993 |
| WO | WO 96/40659 | 12/1996 |
| WO | WO 00/06556 | 2/2000 |
| WO | WO 02/12214 | 2/2002 |
| WO | WO 03/097582 | 11/2003 |

OTHER PUBLICATIONS

Massa, Silvio, et al., "[[[(Thienylcarbonyl) alkyl]oxy]phenyl]- and[[[(Pyrrylcarbonyl)alkyl]oxy]phenyl]oxazoline Derivatives with Potent and Selective Antihuman Rhinovirus Activity," J. Med. Chem. 1995, 38, pp. 803-809.
Database Caplus, Chemical Abstracts Service, XP002352583.
Database Caplus, Chemical Abstracts Service, XP002352584.
Database Caplus, Chemical Abstracts Service, XP002352585.
Lai, Yen-Shi, et al., "Synthesis and Protein Kinase C. Inhibitory Activities of Balanol Analogs with Replacement of the Perhydroazepine Moiety," J. Med. Chem. 1997, 40, pp. 226-235.
Matsumoto, Takashi, et al., "C-Glycosyl Juglone in Angucycline Synthesis: Total Synthesis of Galtamycinone, Common Aglycon of C-Glycosyl Naphthacenequinone-Type Angucyclines," Tetrahedron, 1997, vol. 53, No. 48, pp. 16533-16544.
Serrano, Jose Luis, et al., "Improving FLC Properties. Simplicity, Planarity, and Rigidity in New Chiral Oxazoline Derivatives," J. Am. Chem. Soc. 1995, 117, pp. 8312-8321.
Database Caplus, Chemical Abstracts Service, XP002352586.

* cited by examiner

*Primary Examiner*—Rita J Desai
*Assistant Examiner*—John Mabry
(74) *Attorney, Agent, or Firm*—McDonnell Boehnen Hulbert & Berghoff LLP

(57) ABSTRACT

The present invention relates to compounds comprising an oxazoline or thiazoline moiety, processes for preparing them, pharmaceutical compositions comprising said compounds and their uses as $H_3$-receptor ligands, (I), wherein $A^1$ is CH C(CH$_3$) or N; $R^1$ is hydrogen or halogen; $R^2$ is (II); $A^2$ is O or S; $R^3$ is hydrogen, halogen, $C_{1-4}$ alkyl or $C_{1-4}$ alkoxy; $R^4$ is hydrogen, halogen, $C_{1-4}$ alkyl, $C_{1-4}$ alkoxy, trifluoromethyl or —O—(CH$_2$)n-NR$^{12a}{}_R$ each CH$_2$ in —O—(CH$_2$)n-NR$^{12a}{}_R$12b being optionally substituted by one or two $C_{1-4}$ alkyl; $R^5$ is hydrogen or —O—(CH$_2$)$_m$—NR$^{13a}{}_R{}^{13b}$, each CH$_2$ in —O—(CH$_2$)$_m$—NR$^{13a}$R$^{13b}$ being optionally substituted by one or two $C_{1-4}$ alkyl, and at least one of $R^4$ and $R^5$ should be a —O—(CH$_2$)n-NR$^{12/13a}$R$^{12/13b}$ group.

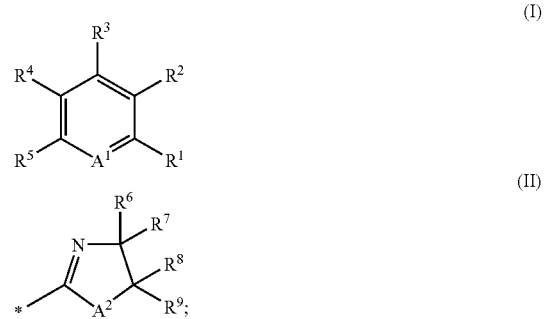

3 Claims, No Drawings

COMPOUNDS COMPRISING AN OXAZOLINE OR THIAZOLINE MOIETY, PROCESSES FOR MAKING THEM, AND THEIR USES

CROSS-REFERENCE TO RELATED APPLICATIONS

This application is a U.S. National Stage of International Application No. PCT/EP2006/002860, filed Mar. 29, 2006.

The present invention relates to compounds comprising an oxazoline, or thiazoline moiety, processes for preparing them, pharmaceutical compositions comprising said compounds and their uses as pharmaceuticals.

The histamine $H_3$ receptor has been known for several years and identified pharmacologically in 1983 by Arrang, J. M. et al. (Nature 1983, 302, 832). Since the cloning of the human histamine $H_3$ receptor in 1999, histamine $H_3$ receptors have been successively cloned by sequence homology from a variety of species, including rat, guinea pig, mouse and monkey.

Histamine $H_3$-receptor agonists, antagonists and inverse agonists have shown potential therapeutic applications as described in the literature, for example by Stark, H. (Exp. Opin. Ther. Patents 2003, 13, 851).

The histamine $H_3$ receptor is predominantly expressed in the mammalian central nervous system but can also be found in the autonomic nervous system. Evidence has been shown that the histamine $H_3$ receptor displays high constitutive activity, which activity occurs in the absence of endogenous histamine or of a $H_3$-receptor agonist. Thus, a histamine $H_3$ receptor antagonist and/or inverse agonist could inhibit this activity.

The general pharmacology of histamine $H_3$ receptor, including $H_3$-receptor subtypes, has been reviewed by Hancock, A. A (Life Sci. 2003, 73, 3043). The histamine $H_3$ receptor is not only considered as a presynaptic autoreceptor on histaminergic neurons, but also as a heteroreceptor on non-histaminergic neurons (Barnes, W. et al., Eur. J. Pharmacol. 2001, 431, 215). Indeed, the histamine $H_3$ receptor has been shown to regulate the release of histamine but also of other important neurotransmitters, including acetylcholine, dopamine, serotonin, norepinephrin and γ-aminobutyric acid (GABA).

Thus, the histamine $H_3$ receptor is of current interest for the development of new therapeutics and the literature suggests that novel histamine $H_3$-receptor antagonists or inverse agonists may be useful for the treatment and prevention of diseases or pathological conditions of the central nervous system including as mild cognitive impairment (MCI), Alzheimer's disease, learning and memory disorders, cognitive disorders, attention deficit disorder (ADD), attention-deficit hyperactivity disorder (ADHD), Parkinson's disease, schizophrenia, dementia, depression, epilepsy, seizures or convulsions, sleep/wake disorders, narcolepsy, and/or obesity.

$H_3$-receptor ligands alone or in combination with an acetylcholinesterase inhibitor may also be useful in the treatment of cholinergic-deficit disorders, mild cognitive impairment and Alzheimer's disease as reported by Morisset, S. et al. in Eur. J. Pharmacol. 1996, 315, R1-R2.

$H_3$-receptor ligands, alone or in combination with a histamine $H_1$-receptor antagonist may be useful for the treatment of upper airway allergic disorders, as reported by McLeod, R. et al. in J. Pharmacol. Exp. Ther. 2003, 305, 1037.

As described in international patent application WO02/072093, $H_3$-receptor ligands alone or in combination with a muscarinic receptor ligand and particularly with a muscarinic $M_2$-receptor antagonist, may be useful for the treatment of cognitive disorders, Alzheimer's disease, attention-deficit hyperactivity disorder.

$H_3$-receptor ligands may also be useful in the treatment of sleep/wake and arousal/vigilance disorders such as hypersomnia, and narcolepsy according to Passani, M. B. et al. in Trends Pharmacol. Sci. 2004, 25(12), 618-25.

In general, $H_3$-receptor, and particularly $H_3$-receptor antagonists or inverse agonists may be useful in the treatment of all type of cognitive-related disorders as reviewed by Hancock, A. A and Fox, G. B. in Expert Opin. Invest. Drugs 2004, 13, 1237.

In particular, histamine $H_3$-receptor antagonists or inverse agonists may be useful in the treatment of cognitive dysfunctions in diseases such as mild cognitive impairment, dementia, Alzheimer's disease, Parkinson's disease, Down's syndrome as well as in the treatment of attention-deficit hyperactivity disorder (ADHD) as non-psychostimulant agents (see for example Witkin, J. M. et al., Pharmacol. Ther. 2004, 103(1), 1-20).

$H_3$ receptor antagonists or inverse agonists may also be useful in the treatment of psychotic disorders such as schizophrenia, migraine, eating disorders such as obesity, inflammation, pain, anxiety, stress, depression and cardiovascular disorders, in particular acute myocardial infarction.

There is therefore a need to manufacture new compounds which can potentially act as $H_3$-receptor ligands.

Early literature reports (e.g. Ali, S. M. et al., in J. Med. Chem. 1999, 42, 903 and Drugs Fut. 1996, 21, 507) describe that an imidazole function is essential for high affinity histamine $H_3$-receptor ligands; this is confirmed, for example, by U.S. Pat. No. 6,506,756B2, U.S. Pat. No. 6,518,287B2, U.S. Pat. No. 6,528,522B2 and U.S. Pat. No. 6,762,186B2 which relate to substituted imidazole compounds that have $H_3$-receptor antagonist or dual histamine $H_1$-receptor and $H_3$-receptor antagonist activity.

International patent application WO 02/12214 describes non-imidazole aryloxyalkylamines useful for the treatment of conditions and disorders mediated by the histamine receptor.

U.S. Pat. No. 4,992,433 describes compounds comprising oxazoline and pyridazinamine moieties having antiviral activity.

Massa, S. et al. in J. Med. Chem. 1995, 38, 803 describe thienyl and pyrryl compounds comprising an oxazoline moiety which compounds have an antirhinovirus activity.

It has now surprisingly been found that certain compounds comprising an oxazoline, or thiazoline moiety may act as $H_3$-receptor ligands and therefore may demonstrate therapeutic properties for one or more pathologies that we have described above.

Therefore, in a first aspect, the present invention relates to a compound of formula (I), geometrical isomers, enantiomers, diastereoisomers, pharmaceutically acceptable salts and all possible mixtures thereof,

(I)

wherein
A$^1$ is CH, C(CH$_3$) or N;
R$^1$ is hydrogen or halogen;
R$^2$ is

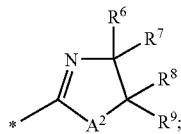

(II)

A$^2$ is O or S;
R$^3$ is hydrogen, halogen, C$_{1-4}$ alkyl or C$_{1-4}$ alkoxy;
R$^4$ is hydrogen, halogen, C$_{1-4}$ alkyl, C$_{1-4}$ alkoxy, trifluoromethyl or —O—(CH$_2$)$_n$—NR$^{12a}$R$^{12b}$ each CH$_2$ in —O—(CH$_2$)$_n$—NR$^{12a}$R$^{12b}$ being optionally substituted by one or two C$_{1-4}$ alkyl;
R$^5$ is hydrogen or —O—(CH$_2$)$_m$—NR$^{13a}$R$^{13b}$, each CH$_2$ in —O—(CH$_2$)$_m$—NR$^{13a}$R$^{13b}$ being optionally substituted by one or two C$_{1-4}$ alkyl;
R$^6$ is hydrogen or C$_{1-4}$ alkyl;
R$^7$ is hydrogen, C$_{1-8}$ alkyl, aryl, arylalkyl, or —(CH$_2$)$_v$—NR$^{14a}$R$^{14b}$;
or R$^6$ and R$^7$ are linked together to form a C$_{2-8}$ alkylene in which one methylene of the alkylene is optionally replaced by a nitrogen atom which nitrogen atom is optionally substituted by an arylalkyl or C$_{1-8}$ alkyl;
or R$^7$ and R$^9$ are linked together to form a C$_{3-6}$ alkylene;
R$^8$ is hydrogen; or R$^8$ and R$^9$ are linked together to form a C$_{2-8}$ alkylene;
R$^9$ is hydrogen or aryl; or R$^7$ and R$^9$ are linked together to form a C$_{3-6}$ alkylene; or
R$^8$ and R$^9$ are linked together to form a C$_{2-8}$ alkylene;
R$^{12a}$ and R$^{12b}$ are linked together to form a C$_{3-6}$ alkylene, each methylene of the alkylene being optionally substituted by one or two C$_{1-4}$ alkyl;
R$^{13a}$ and R$^{13b}$ are linked together to form a C$_{3-6}$ alkylene, each methylene of the alkylene being optionally substituted by one or two C$_{1-4}$ alkyl, an amino group or an aminoalkyl, one methylene being optionally replaced by a nitrogen atom, said nitrogen atom being optionally substituted by a C$_{1-8}$ alkyl or an aminoalkyl;
R$^{14a}$ and R$^{14b}$ are linked together to form a C$_{3-6}$ alkylene, each methylene of the alkylene being optionally substituted by one or two C$_{1-4}$ alkyl;
n and m are independently an integer comprised between 2 and 8;
v is an integer comprised between 1 and 4;
with the proviso that R$^4$ is —O—(CH$_2$)$_n$—NR$^{12a}$R$^{12b}$, when R$^5$ is hydrogen and that R$^5$ is —O—(CH$_2$)$_m$—NR$^{13a}$R$^{13b}$, when R$^4$ is hydrogen, halogen, trifluoromethyl, C$_{1-4}$ alkyl or C$_{1-4}$ alkoxy;
with the proviso that at least one of R$^6$, R$^7$, R$^8$ and R$^9$ is different from H.

The asterisk shows the point of attachment of substituent R$^2$.

The term "alkyl", as used herein, is a group which represents saturated, monovalent hydrocarbon radicals having straight (unbranched), branched or cyclic moieties, or combinations thereof and containing 1-10 carbon atoms, preferably 1-8 carbon atoms; more preferably alkyl groups have 1-6 carbon atoms, most preferably alkyl groups have 1-4 carbon atoms. Alkyl moieties may optionally be substituted by 1 to 5 substituents independently selected from the group consisting of halogen, hydroxy, alkoxy or aryl. Preferred alkyl groups are methyl, isopropyl, tert-butyl and cyclohexylmethyl.

The term "cycloalkyl", as used herein, represents a monovalent group of 3 to 8 carbon atoms, usually 3 to 6 carbon atoms derived from a saturated cyclic hydrocarbon, which may be substituted by any suitable group including but not limited to one or more moieties selected from groups as described above for the alkyl groups. Preferred cycloalkyl are cyclopropyl, cyclopentyl and cyclohexyl.

The term "alkylene", as used herein, represents a group of formula —(CH$_2$)$_x$— in which x is comprised between 1 and 10, preferably comprised between 2 and 8, more preferably comprised between 2 and 6.

The term "methylene" as used herein represents a group of formula —CH$_2$—.

The term "aryl" as used herein, is defined as a phenyl group optionally substituted by 1 to 4 substituents independently selected from halogen, C$_{1-4}$ alkyl or C$_{1-4}$ alkoxy. Preferred aryl is phenyl.

The term "phenyl", as used herein, represents an aromatic hydrocarbon group of formula —C$_6$H$_5$.

The term "halogen", as used herein, represents an atom of fluorine, chlorine, bromine, or iodine.

The term "hydroxy", as used herein, represents a group of formula —OH.

The term "alkoxy", as used herein, represents a group of formula OR$^a$ wherein R$^a$ is an alkyl group, as defined above. Preferred alkoxy group is methoxy.

The term "carbonyl", used herein represents a group of formula C═O.

The term "amino group", as used herein, represents a group of formula —NH$_2$, NHR$^b$ or NR$^b$R$^c$ wherein R$^b$ and R$^c$C are alkyl groups as defined above in the specification or are linked together to form with N a pyrrolidinyl, piperidinyl or azepanyl group. Preferred amino groups are dimethylamino or 1-pyrrolidinyl.

The term "aminoalkyl", as used herein, represents a C$_{1-4}$ alkyl group substituted by an amino group as defined above. Preferred aminoalkyl group are 2-pyrrolidin-1-ylethyl and pyrrolidin-1 ylmethyl.

The term "arylalkyl", as used herein, represents a group of formula —R$^d$-aryl in which R$^d$ is C$_{1-4}$ alkylene. Preferred arylalkyl group is benzyl.

Usually, A$^1$ is CH, C(CH$_3$) or N. Preferably A$^1$ is CH or N. In a particular embodiment A$^1$ is CH.

Usually, A$^2$ is O or S. More preferably, A$^2$ is O. In a particular embodiment A$^2$ is S.

Usually in one embodiment, R$^1$ is hydrogen. Usually, in another embodiment, R$^1$ is hydrogen or fluorine.

Preferably, R$^1$ is hydrogen.

Usually in one embodiment, R$^3$ is hydrogen or halogen. Usually, in another embodiment, R$^3$ is hydrogen, bromine, methyl or methoxy.

Preferably, R$^3$ is hydrogen or bromine. More preferably, R$^3$ is hydrogen.

Usually, in one embodiment, R$^4$ is hydrogen or —O—(CH$_2$)$_n$—NR$^{12a}$R$^{12b}$. Usually, in another embodiment, R$^4$ is hydrogen, fluorine, chlorine, methyl, methoxy, trifluoromethyl or —O—(CH$_2$)$_n$—NR$^{12a}$R$^{12b}$. Preferably, R$^4$ is hydrogen or —O—(CH$_2$)$_n$—NR$^{12a}$R$^{12b}$. More preferably, R$^4$ is hydrogen.

Usually, R$^{12a}$ and R$^{12b}$ are linked together to form a C$_{3-6}$ alkylene, each methylene being optionally substituted by one or two C$_{1-4}$ alkyl. Preferably, —NR$^{12a}$R$^{12b}$ is selected from the group consisting of 1-piperidinyl, 1-pyrrolidinyl or 2-methylpyrrolidin-1-yl.

Usually, n is comprised between 2 and 5. Preferably, n is equal to 3.

Usually, $R^5$ is hydrogen or $-O-(CH_2)_m-NR^{13a}R^{13b}$, each $CH_2$ in $-O-(CH_2)_m-NR^{13a}R^{13b}$ being optionally substituted by one or two $C_{1-4}$ alkyl.

Preferably, $R^5$ is hydrogen or $-O-(CH_2)_m-NR^{13a}R^{13b}$, each $CH_2$ in $-O-(CH_2)_m-NR^{13a}R^{13b}$ being optionally substituted by one or two methyl. More preferably, $R^5$ is $-O-(CH_2)_m-NR^{13a}R^{13b}$.

Usually in one embodiment, $R^{13a}$ and $R^{13b}$ are linked together to form a $C_{3-6}$ alkylene, each methylene of the alkylene being optionally substituted by one or two $C_{1-4}$ alkyl, or an amino group, one methylene of the alkylene being optionally replaced by a nitrogen atom, said nitrogen atom being optionally substituted by a $C_{1-8}$ alkyl or an aminoalkyl. Usually, in another embodiment, $R^{13a}$ and $R^{13b}$ are linked together to form a $C_{3-6}$ alkylene, each methylene of the alkylene being optionally substituted by one or two $C_{1-4}$ alkyl, a dimethylamino or a pyrrolidin-1 ylmethyl, one methylene of the alkylene being optionally replaced by a nitrogen atom, which nitrogen atom is substituted by a $C_{1-8}$ alkyl or a pyrrolidin-1-ylethyl.

Preferably, $-NR^{13a}R^{13b}$ is selected from the group consisting of 1-piperidinyl, 1-pyrrolidinyl, 2-methylpyrrolidin-1-yl, 4-isopropylpiperazin-1-yl, 2-methylpiperidin-1-yl, 3-(dimethylamino)pyrrolidin-1-yl, 3,5-dimethylpiperidin-1-yl or 2,5-dimethylpyrrolidin-1-yl;

More preferably, $-NR^{13a}R^{13b}$ is selected from the group consisting of 1-piperidinyl, 1-pyrrolidinyl and 2-methylpyrrolidin-1-yl.

Most preferably, $-NR^{13a}R^{13b}$ is selected from the group consisting of 1-piperidinyl and 2-methylpyrrolidin-1-yl. In a particularly preferred embodiment according to the invention $-NR^{13a}R^{13b}$ is 2-methylpyrrolidin-1-yl.

Usually, m is comprised between 2 and 5. Preferably, m is equal to 3.

Usually in one embodiment, $R^6$ is hydrogen or $C_{1-4}$ alkyl; or $R^6$ and $R^7$ are linked together to form a $C_{2-8}$ alkylene in which one methylene of the alkylene is optionally replaced by a nitrogen atom which nitrogen atom is optionally substituted by an arylalkyl or a $C_{3-6}$ cycloalkyl. Usually, in another embodiment, $R^6$ is hydrogen or $C_{1-4}$ alkyl; or $R^6$ and $R^7$ are linked together to form a $C_{2-8}$ alkylene in which one methylene of the alkylene is optionally replaced by a nitrogen atom which nitrogen atom is optionally substituted by a benzyl, a $C_{3-6}$ cycloalkyl or a $C_{1-8}$ alkyl.

Preferably, $R^6$ is hydrogen or methyl; or $R^6$ and $R^7$ are linked together to form a $C_{2-5}$ alkylene, one methylene of the alkylene being optionally replaced by a nitrogen atom, said nitrogen atom being optionally substituted by a cyclopentyl or a benzyl group.

More preferably, $R^6$ is hydrogen or methyl; or $R^6$ and $R^7$ are linked together to form a $C_{4-5}$ alkylene, one methylene of the alkylene being optionally replaced by a nitrogen atom, said nitrogen atom being optionally substituted by a cyclopentyl or a benzyl group.

Most preferably, $R^6$ is hydrogen or methyl; or $R^6$ and $R^7$ are linked together to form a $C_5$ alkylene, one methylene of the alkylene being optionally replaced by a nitrogen atom, said nitrogen atom being optionally substituted by a cyclopentyl or a benzyl group.

Usually, in one embodiment, $R^7$ is hydrogen, $C_{1-8}$ alkyl, aryl, arylalkyl, or $-(CH_2)_v-NR^{14a}R^{14b}$; or $R^6$ and $R^7$ are linked together to form a $C_{2-8}$ alkylene in which one methylene is optionally replaced by a nitrogen atom, which nitrogen atom is optionally substituted by an arylalkyl or a $C_{3-6}$ cycloalkyl; or $R^7$ and $R^9$ are linked together to form a $C_{3-6}$ alkylene. Usually in another embodiment, $R^7$ is hydrogen, $C_{1-8}$ alkyl, phenyl, benzyl or $(CH_2)_v-NR^{14a}R^{14b}$; or $R^6$ and $R^7$ are linked together to form a $C_{2-8}$ alkylene in which one methylene of the alkylene is optionally replaced by a nitrogen atom which nitrogen atom is optionally substituted by a benzyl, a $C_{3-6}$ cycloalkyl or a $C_{1-8}$ alkyl; or $R^7$ and $R^9$ are linked together to form a $C_{3-6}$ alkylene.

Preferably, $R^7$ is hydrogen, methyl, tert-butyl, cyclohexylmethyl, phenyl, benzyl or $-(CH_2)_v-NR^{14a}R^{14b}$; or $R^6$ and $R^7$ are linked together to form a $C_{2-5}$ alkylene one methylene of the alkylene being optionally replaced by a nitrogen atom, said nitrogen atom being optionally substituted by a cyclopentyl or a benzyl group; or $R^7$ and $R^9$ are linked together to form a $C_4$ alkylene.

More preferably, $R^7$ is methyl, tert-butyl, benzyl or $-(CH_2)_v-NR^{14a}R^{14b}$; or $R^6$ and $R^7$ are linked together to form a $C_{4-5}$ alkylene one methylene of the alkylene being optionally replaced by a nitrogen atom, said nitrogen atom being optionally substituted by a cyclopentyl or a benzyl group; or $R^7$ and $R^9$ are linked together to form a $C_4$ alkylene.

Most preferably, $R^7$ is selected from the group consisting of methyl, piperidin-1-ylmethyl, pyrrolidin-1-ylmethyl; or $R^6$ and $R^7$ are linked together to form a $C_5$ alkylene.

Usually in one embodiment, $R^{14a}$ and $R^{14b}$ are linked together to form a $C_{3-6}$ alkylene, each methylene of the alkylene being optionally substituted by one or two $C_{1-4}$ alkyl. Usually in another embodiment, $R^{14a}$ and $R^{14b}$ are linked together to form a $C_{3-6}$ alkylene, each methylene of the alkylene being optionally substituted by a methyl group. Preferably, $-NR^{14a}R^{14b}$ is selected from the group consisting of 1-piperidinyl, 1-pyrrolidinyl and 1-azepanyl.

Usually, v is an integer comprised between 1 and 3. Preferably, v is equal to 1 or 2. Most preferably, v is equal to 1.

Usually in one embodiment, $R^8$ is hydrogen; or $R^8$ and $R^9$ are linked together to form a $C_{2-8}$ alkylene. Usually in another embodiment, $R^8$ is hydrogen; or $R^8$ and $R^9$ are linked together to form a $C_{2-5}$ alkylene.

Preferably, $R^8$ is hydrogen; or $R^8$ and $R^9$ are linked together to form a $C_5$ alkylene. More preferably, $R^8$ is hydrogen.

Usually in one embodiment, $R^9$ is hydrogen or aryl; or $R^7$ and $R^9$ are linked together to form a $C_{3-6}$ alkylene; or $R^8$ and $R^9$ are linked together to form a $C_{2-8}$ alkylene. Usually in another embodiment, $R^9$ is hydrogen or phenyl; or $R^7$ and $R^9$ are linked together to form a $C_{3-6}$ alkylene; or $R^8$ and $R^9$ are linked together to form a $C_{2-5}$ alkylene.

Preferably, $R^9$ is hydrogen or phenyl; or $R^7$ and $R^9$ are linked together to form a $C_4$ alkylene; or $R^8$ and $R^9$ are linked together to form a $C_5$ alkylene.

More preferably, $R^9$ is hydrogen; or $R^7$ and $R^9$ are linked together to form a $C_4$ alkylene.

Most preferably, $R^9$ is hydrogen.

Combinations of one or more of these preferred groups are especially preferred.

Usually in one embodiment, the present invention relates to compounds of formula (I), geometrical isomers, enantiomers, diastereoisomers, pharmaceutically acceptable salts and all possible mixtures thereof,

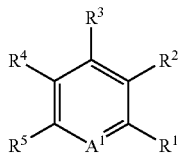

(I)

wherein
$A^1$ is CH or N;
$R^1$ is hydrogen;
$R^2$ is

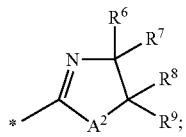

(II)

$A^2$ is O or S;
$R^3$ is hydrogen or halogen;
$R^4$ is hydrogen or —O—$(CH_2)_n$—$NR^{12a}R^{12b}$;
$R^5$ is hydrogen or —O—$(CH_2)_m$—$NR^{13a}R^{13b}$, each $CH_2$ in —O—$(CH_2)_m$—$NR^{13a}R^{13b}$ being optionally substituted by one or two $C_{1-4}$ alkyl;
$R^6$ is hydrogen or $C_{1-4}$ alkyl; or $R^6$ and $R^7$ are linked together to form a $C_{2-8}$ alkylene in which one methylene of the alkylene is optionally replaced by a nitrogen atom which nitrogen atom is optionally substituted by an arylalkyl or a $C_{3-6}$ cycloalkyl;
$R^7$ is hydrogen, $C_{1-8}$ alkyl, aryl, arylalkyl, or —$(CH_2)_v$—$NR^{14a}R^{14b}$; or $R^6$ and $R^7$ are linked together to form a $C_{2-8}$ alkylene in which one methylene is optionally replaced by a nitrogen atom which nitrogen atom is optionally substituted by a $C_{3-6}$ cycloalkyl or an arylalkyl; or $R^7$ and $R^9$ are linked together to form a $C_{3-6}$ alkylene;
$R^8$ is hydrogen; or $R^8$ and $R^9$ are linked together to form a $C_{2-8}$ alkylene;
$R^9$ is hydrogen or aryl; or $R^7$ and $R^9$ are linked together to form a $C_{3-6}$ alkylene; or
$R^8$ and $R^9$ are linked together to form a $C_{2-8}$ alkylene;
$R^{12a}$ and $R^{12b}$ are linked together to form a $C_{3-6}$ alkylene, each methylene of the alkylene being optionally substituted by a $C_{1-4}$ alkyl;
$R^{13a}$ and $R^{13b}$ are linked together to form a $C_{3-6}$ alkylene, each methylene of the alkylene being optionally substituted by one or two $C_{1-4}$ alkyl, an amino group, one methylene of the alkylene being optionally replaced by a nitrogen atom, said nitrogen atom being optionally substituted by a $C_{1-8}$ alkyl;
$R^{14a}$ and $R^{14b}$ are linked together to form a $C_{3-6}$ alkylene, each methylene of the alkylene being optionally substituted by one or two $C_{1-4}$ alkyl;
n and m are independently an integer comprised between 2 and 5;
v is an integer comprised between 1 and 3;
with the proviso that $R^4$ is —O—$(CH_2)_n$—$NR^{12a}R^{12b}$, when $R^5$ is hydrogen and that $R^5$ is —O—$(CH_2)_m$—$NR^{13a}R^{13b}$, when $R^4$ is hydrogen;
with the proviso that at least one of $R^6$, $R^7$, $R^8$ and $R^9$ is different from H.

Usually in another embodiment, the invention relates to compounds of formula (I), geometrical isomers, enantiomers, diastereoisomers, pharmaceutically acceptable salts and all possible mixtures thereof,

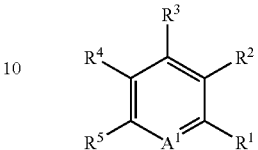

(I)

wherein
$A^1$ is CH, C(CH$_3$) or N;
$R^1$ is hydrogen or fluorine;
$R^2$ is

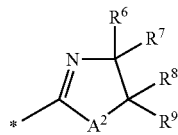

(II)

$A^2$ is O or S;
$R^3$ is hydrogen, bromine, methyl or methoxy;
$R^4$ is hydrogen, fluorine, chlorine, methyl, methoxy, trifluoromethyl or —O—$(CH_2)_n$—$NR^{12a}R^{12b}$;
$R^5$ is hydrogen or —O—$(CH_2)_m$—$NR^{13a}R^{13b}$, each $CH_2$ in —O—$(CH_2)_m$—$NR^{13a}R^{13b}$ being optionally substituted by one or two $C_{1-4}$ alkyl;
$R^6$ is hydrogen or a $C_{1-4}$ alkyl; or $R^6$ and $R^7$ are linked together to form a $C_{2-8}$ alkylene in which one methylene of the alkylene is optionally replaced by a nitrogen atom, which nitrogen atom is optionally substituted by benzyl, a $C_{1-8}$ alkyl, or a $C_{3-6}$ cycloalkyl;
$R^7$ is hydrogen, a $C_{1-8}$ alkyl, phenyl, benzyl or —$(CH_2)_v$—$NR^{14a}R^{14b}$; or $R^6$ and $R^7$ are linked together to form a $C_{2-8}$ alkylene in which one methylene of the alkylene is optionally replaced by a nitrogen atom which nitrogen atom is optionally substituted by a benzyl, a $C_{1-8}$ alkyl, or a $C_{3-6}$ cycloalkyl; or $R^7$ and $R^9$ are linked together to form a $C_{3-6}$ alkylene;
$R^8$ is hydrogen; or $R^8$ and $R^9$ are linked together to form a $C_{2-5}$ alkylene;
$R^9$ is hydrogen or phenyl; or $R^7$ and $R^9$ are linked together to form a $C_{3-6}$ alkylene; or $R^8$ and $R^9$ are linked together to form a $C_{2-5}$ alkylene;
$R^{12a}$ and $R^{12b}$ are linked together to form a $C_{3-6}$ alkylene, each methylene of the alkylene being optionally substituted by one or two $C_{1-4}$ alkyl;
$R^{13a}$ and $R^{13b}$ are linked together to form a $C_{3-6}$ alkylene, each methylene of the alkylene being optionally substituted by one or two $C_{1-4}$ alkyl, a dimethylamino group, or pyrrolidin-1 ylmethyl, one methylene of the alkylene being optionally replaced by a nitrogen atom, which nitrogen atom is substituted by a $C_{1-8}$ alkyl, a $C_{3-6}$ cycloalkyl or a pyrrolidin-1-ylethyl;

$R^{14a}$ and $R^{14b}$ are linked together to form a $C_{3-6}$ alkylene, each methylene of the alkylene being optionally substituted by a methyl;

n and m are independently an integer comprised between 2 and 5;

v is an integer comprised between 1 and 3;

with the proviso that $R^4$ is $-O-(CH_2)_n-NR^{12a}R^{12b}$, when $R^5$ is hydrogen and that $R^5$ is $-O-(CH_2)_m-NR^{13a}R^{13b}$, when $R^4$ is hydrogen, fluorine, chlorine, methyl, methoxy or trifluoromethyl;

with the proviso that at least one of $R^6$, $R^7$, $R^8$ and $R^9$ is different from H.

Preferably, the invention relates to compounds of formula (I), geometrical isomers, enantiomers, diastereoisomers, pharmaceutically acceptable salts and all possible mixtures thereof,

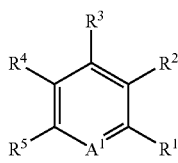
(I)

wherein
$A^1$ is CH or N;
$R^1$ is hydrogen;
$R^2$ is

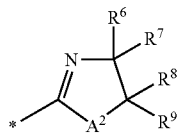
(II)

$A^2$ is O or S;
$R^3$ is hydrogen or bromine;
$R^4$ is hydrogen or $-O-(CH_2)_n-NR^{12a}R^{12b}$;
$R^5$ is hydrogen or $-O-(CH_2)_m-NR^{13a}R^{13b}$, each $CH_2$ in $-O-(CH_2)_m-NR^{13a}R^{13b}$ being optionally substituted by one or two methyl;

$R^6$ is hydrogen or methyl; or $R^6$ and $R^7$ are linked together to form a $C_{2-5}$ alkylene, one methylene of the alkylene being optionally replaced by a nitrogen atom, said nitrogen atom being optionally substituted by a cyclopentyl or a benzyl group;

$R^7$ is hydrogen, methyl, tert-butyl, cyclohexylmethyl, phenyl, benzyl or $-(CH_2)_v-NR^{14a}R^{14b}$; or $R^6$ and $R^7$ are linked together to form a $C_{2-5}$ alkylene, one methylene of the alkylene being optionally replaced by a nitrogen atom, said nitrogen atom being optionally substituted by a cyclopentyl or a benzyl group; or $R^7$ and $R^9$ are linked together to form a $C_4$ alkylene;

$R^8$ is hydrogen; or $R^8$ and $R^9$ are linked together to form a $C_5$ alkylene;

$R^9$ is hydrogen or phenyl; or $R^7$ and $R^9$ are linked together to form a $C_4$ alkylene; or $R^8$ and $R^9$ are linked together to form a $C_{2-8}$ alkylene;

$-NR^{12a}R^{12b}$ is selected from the group consisting of 1-piperidinyl, 1-pyrrolidinyl or 2-methylpyrrolidin-1-yl;

$-NR^{13a}R^{13b}$ is selected from the group consisting of 1-piperidinyl, 1-pyrrolidinyl, 2-methylpyrrolidin-1-yl, 4-isopropylpiperazin-1-yl, 2-methylpiperidin-1-yl, 3-(dimethylamino)pyrrolidin-1-yl, 3,5-dimethylpiperidin-1-yl or 2,5-dimethylpyrrolidin-1-yl;

$-NR^{14a}R^{14b}$ is selected from the group consisting of 1-piperidinyl, 1-azepanyl or 1-pyrrolidinyl;

n is equal to 3;

m is an integer equal to 3;

v is an integer equal to 1 or 2;

with the proviso that $R^4$ is $-O-(CH_2)_n-NR^{12a}R^{12b}$ when $R^5$ is hydrogen and that $R^5$ is $-O-(CH_2)_m-NR^{13a}R^{13b}$ when $R^4$ is hydrogen.

More preferably, the invention relates to compounds of formula (I) geometrical isomers, enantiomers, diastereoisomers, pharmaceutically acceptable salts and all possible mixtures thereof,

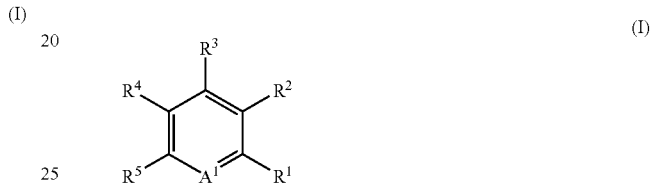
(I)

wherein
$A^1$ is CH or N;
$R^1$ is hydrogen;
$R^2$ is

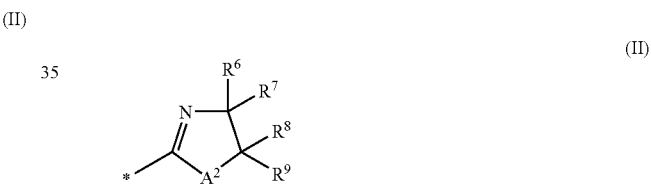
(II)

$A^2$ is O;
$R^3$ is hydrogen;
$R^4$ is hydrogen;
$R^5$ is $-O-(CH_2)_m-NR^{13a}R^{13b}$;
$R^6$ is hydrogen or methyl; or $R^6$ and $R^7$ are linked together to form a $C_{4-5}$ alkylene, one methylene of the alkylene being optionally replaced by a nitrogen atom, said nitrogen atom being optionally substituted by a cyclopentyl or a benzyl group;

$R^7$ is methyl, tert-butyl, benzyl or $-(CH_2)_v-NR^{14a}R^{14b}$; or $R^6$ and $R^7$ are linked together to form a $C_{4-5}$ alkylene, one methylene of the alkylene being optionally replaced by a nitrogen atom, said nitrogen atom being optionally substituted by a cyclopentyl or a benzyl group; or $R^7$ and $R^9$ are linked together to form a $C_4$ alkylene;

$R^8$ is hydrogen;

$R^9$ is hydrogen; or $R^7$ and $R^9$ are linked together to form a $C_4$ alkylene;

$-NR^{13a}R^{13b}$ is selected from the group consisting of 1-piperidinyl, 1-pyrrolidinyl, and 2-methylpyrrolidin-1-yl;

$-NR^{14a}R^{14b}$ is selected from the group consisting of 1-piperidinyl, 1-pyrrolidinyl or 1-azepanyl;

m is an integer equal to 3; and v is an integer equal to 1 or 2.

Most preferably, the invention relates to compound of formula (I), geometrical isomers, enantiomers, diastereoisomers, pharmaceutically acceptable salts and all possible mixtures thereof,

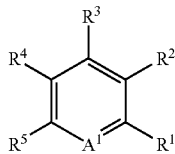

(I)

wherein
$A^1$ is CH or N;
$R^1$ is hydrogen;
$R^2$ is

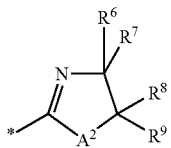

(II)

$A^2$ is O;
$R^3$ is hydrogen;
$R^4$ is hydrogen;
$R^5$ is —O—$(CH_2)_m$—$NR^{13a}R^{13b}$;
$R^6$ is hydrogen or methyl; or $R^6$ and $R^7$ are linked together to form a $C_5$ alkylene, one methylene of the alkylene being optionally replaced by a nitrogen atom, said nitrogen atom being optionally substituted by a cyclopentyl or a benzyl group;
$R^7$ is methyl, piperidin-1-ylmethyl or pyrrolidin-1 ylmethyl; or $R^6$ and $R^7$ are linked together to form a $C_5$ alkylene, one methylene of the alkylene being optionally replaced by a nitrogen atom, said nitrogen atom being optionally substituted by a cyclopentyl or a benzyl group;
$R^8$ is hydrogen;
$R^9$ is hydrogen;
—$NR^{13a}R^{13b}$ is selected from the group consisting of 1-piperidinyl and 2-methylpyrrolidin-1-yl; and
m is an integer equal to 3.

Preferred compounds of formula (I) according to the invention are:
1-{3-[4-(4,4-dimethyl-4,5-dihydro-1,3-oxazol-2-yl)phenoxy]propyl}piperidine;
1-{3-[4-(4,4-dimethyl-4,5-dihydro-1,3-oxazol-2-yl)phenoxy]propyl}-4-isopropylpiperazine;
1-{3-[4-(4,4-dimethyl-4,5-dihydro-1,3-oxazol-2-yl)phenoxy]propyl}-3,5-dimethylpiperidine;
4,4-dimethyl-2-{3-[3-(2-methylpyrrolidin-1-yl)propoxy]phenyl}-4,5-dihydro-1,3-oxazole;
1-(3-{4-[(4S,5R)-4-methyl-5-phenyl-4,5-dihydro-1,3-oxazol-2-yl]phenoxy}propyl)piperidine;
2-[4-(3-piperidin-1-ylpropoxy)phenyl]-3-oxa-1-azaspiro[4.5]dec-1-ene;
2-[3-(3-piperidin-1-ylpropoxy)phenyl]-3-oxa-1-azaspiro[4.5]dec-1-ene;
1-(3-{4-[(4R)-4-benzyl-4,5-dihydro-1,3-oxazol-2-yl]phenoxy}propyl)piperidine;
2-[4-(3-pyrrolidin-1-ylpropoxy)phenyl]-3-oxa-1-azaspiro[4.5]dec-1-ene;
2-{4-[3-(2-methylpiperidin-1-yl)propoxy]phenyl}-3-oxa-1-azaspiro[4.5]dec-1-ene;
2-[3-(3-pyrrolidin-1-ylpropoxy)phenyl]-3-oxa-1-azaspiro[4.5]dec-1-ene;
4,4-dimethyl-2-{4-[3-(2-methylpyrrolidin-1-yl)propoxy]phenyl}-4,5-dihydro-1,3-oxazole;
5-(4,4-dimethyl-4,5-dihydro-1,3-oxazol-2-yl)-2-[3-(2-methylpyrrolidin-1-yl)propoxy]pyridine;
4,4-dimethyl-2-(4-{3-[(2R)-2-methylpyrrolidin-1-yl]propoxy}phenyl)-4,5-dihydro-1,3-oxazole;
2-{6-[3-(2-methylpyrrolidin-1-yl)propoxy]pyridin-3-yl}-3-oxa-1-azaspiro[4.5]dec-1-ene;
1-{3-[3-bromo-4-(4,4-dimethyl-4,5-dihydro-1,3-oxazol-2-yl)phenoxy]propyl}piperidine;
2-(4-{3-[2,5-dimethylpyrrolidin-1-yl]propoxy}phenyl)-4,4-dimethyl-4,5-dihydro-1,3-oxazole;
1-{3-[4-(4,4-dimethyl-4,5-dihydro-1,3-oxazol-2-yl)phenoxy]propyl}-N,N-dimethylpyrrolidin-3-amine;
1-(3-{4-[4-(piperidin-1-ylmethyl)-4,5-dihydro-1,3-oxazol-2-yl]phenoxy}propyl)piperidine;
1-(3-{4-[4-(pyrrolidin-1-ylmethyl)-4,5-dihydro-1,3-oxazol-2-yl]phenoxy}propyl)piperidine;
1-(3-{4-[4-(2-pyrrolidin-1-ylethyl)-4,5-dihydro-1,3-oxazol-2-yl]phenoxy}propyl)piperidine;
1-{3-[4-(4,4-dimethyl-4,5-dihydro-1,3-thiazol-2-yl)phenoxy]propyl}piperidine;
5-[4-(3-piperidin-1-ylpropoxy)phenyl]-6-oxa-4-azaspiro[2.4]hept-4-ene;
(4S)-4-tert-butyl-2-{4-[3-(2-methylpyrrolidin-1-yl)propoxy]phenyl}-4,5-dihydro-1,3-oxazole;
(3aR,7aR)-2-{4-[3-(2-methylpyrrolidin-1-yl)propoxy]phenyl}-3a,4,5,6,7,7a-hexahydro-1,3-benzoxazole;
(4S)-2-{4-[3-(2-methylpyrrolidin-1-yl)propoxy]phenyl}-4-phenyl-4,5-dihydro-1,3-oxazole;
(4S)-4-(cyclohexylmethyl)-2-{4-[3-(2-methylpyrrolidin-1-yl)propoxy]phenyl}-4,5-dihydro-1,3-oxazole;
2-[4-(3-piperidin-1-ylpropoxy)phenyl]-1-oxa-3-azaspiro[4.5]dec-2-ene;
8-benzyl-2-{4-[3-(2-methylpyrrolidin-1-yl)propoxy]phenyl}-3-oxa-1,8-diazaspiro[4.5]dec-1-ene;
7-benzyl-2-{4-[3-(2-methylpyrrolidin-1-yl)propoxy]phenyl}-3-oxa-1,7-diazaspiro[4.4]non-1-ene;
8-cyclopentyl-2-{4-[3-(2-methylpyrrolidin-1-yl)propoxy]phenyl}-3-oxa-1,8-diazaspiro[4.5]dec-1-ene;
5-[4-methyl-4-(pyrrolidin-1-ylmethyl)-4,5-dihydro-1,3-oxazol-2-yl]-2-[3-(2-methylpyrrolidin-1-yl)propoxy]pyridine;
5-[4-methyl-4-(piperidin-1-ylmethyl)-4,5-dihydro-1,3-oxazol-2-yl]-2-[3-(2-methylpyrrolidin-1-yl)propoxy]pyridine;
1-[(4-methyl-2-{6-[3-(2-methylpyrrolidin-1-yl)propoxy]pyridin-3-yl}-4,5-dihydro-1,3-oxazol-4-yl)methyl]azepane;
2-{4-[3-(2-methylpyrrolidin-1-yl)propoxy]phenyl}-3-oxa-1,8-diazaspiro[4.5]dec-1-ene;
2-[4-(1-methyl-3-piperidin-1-ylpropoxy)phenyl]-3-oxa-1-azaspiro[4.5]dec-1-ene; and
2-[4-(2-methyl-3-piperidin-1-ylpropoxy)phenyl]-3-oxa-1-azaspiro[4.5]dec-1-ene.

More preferred compounds of formula (I) according to the invention are:
1-{3-[4-(4,4-dimethyl-4,5-dihydro-1,3-oxazol-2-yl)phenoxy]propyl}piperidine;
2-[4-(3-piperidin-1-ylpropoxy)phenyl]-3-oxa-1-azaspiro[4.5]dec-1-ene;
1-(3-{4-[(4R)-4-benzyl-4,5-dihydro-1,3-oxazol-2-yl]phenoxy}propyl)piperidine;

2-[4-(3-pyrrolidin-1-ylpropoxy)phenyl]-3-oxa-1-azaspiro[4.5]dec-1-ene;
4,4-dimethyl-2-{4-[3-(2-methylpyrrolidin-1-yl)propoxy]phenyl}-4,5-dihydro-1,3-oxazole;
4,4-dimethyl-2-(4-{3-[(2R)-2-methylpyrrolidin-1-yl]propoxy}phenyl)-4,5-dihydro-1,3-oxazole;
2-{6-[3-(2-methylpyrrolidin-1-yl)propoxy]pyridin-3-yl}-3-oxa-1-azaspiro[4.5]dec-1-ene;
1-(3-{4-[4-(piperidin-1-ylmethyl)-4,5-dihydro-1,3-oxazol-2-yl]phenoxy}propyl)piperidine;
1-(3-{4-[4-(pyrrolidin-1-ylmethyl)-4,5-dihydro-1,3-oxazol-2-yl]phenoxy}propyl)piperidine;
1-(3-{4-[4-(2-pyrrolidin-1-ylethyl)-4,5-dihydro-1,3-oxazol-2-yl]phenoxy}propyl)piperidine;
(4S)-4-tert-butyl-2-{4-[3-(2-methylpyrrolidin-1-yl)propoxy]phenyl}-4,5-dihydro-1,3-oxazole;
(3aR,7aR)-2-{4-[3-(2-methylpyrrolidin-1-yl)propoxy]phenyl}-3a,4,5,6,7,7a-hexahydro-1,3-benzoxazole;
8-benzyl-2-{4-[3-(2-methylpyrrolidin-1-yl)propoxy]phenyl}-3-oxa-1,8-diazaspiro[4.5]dec-1-ene;
7-benzyl-2-{4-[3-(2-methylpyrrolidin-1-yl)propoxy]phenyl}-3-oxa-1,7-diazaspiro[4.4]non-1-ene;
8-cyclopentyl-2-{4-[3-(2-methylpyrrolidin-1-yl)propoxy]phenyl}-3-oxa-1,8-diazaspiro[4.5]dec-1-ene;
5-[4-methyl-4-(pyrrolidin-1-ylmethyl)-4,5-dihydro-1,3-oxazol-2-yl]-2-[3-(2-methylpyrrolidin-1-yl)propoxy]pyridine;
5-[4-methyl-4-(piperidin-1-ylmethyl)-4,5-dihydro-1,3-oxazol-2-yl]-2-[3-(2-methylpyrrolidin-1-yl)propoxy]pyridine;
1-[(4-methyl-2-{6-[3-(2-methylpyrrolidin-1-yl)propoxy]pyridin-3-yl}-4,5-dihydro-1,3-oxazol-4-yl)methyl]azepane; and
2-{4-[3-(2-methylpyrrolidin-1-yl)propoxy]phenyl}-3-oxa-1,8-diazaspiro[4.5]dec-1-ene.

Most preferred compounds of formula (I) according to the invention are:
4,4-dimethyl-2-{4-[3-(2-methylpyrrolidin-1-yl)propoxy]phenyl}-4,5-dihydro-1,3-oxazole;
4,4-dimethyl-2-(4-{3-[(2R)-2-methylpyrrolidin-1-yl]propoxy}phenyl)-4,5-dihydro-1,3-oxazole;
2-{6-[3-(2-methylpyrrolidin-1-yl)propoxy]pyridin-3-yl}-3-oxa-1-azaspiro[4.5]dec-1-ene;
1-(3-{4-[4-(piperidin-1-ylmethyl)-4,5-dihydro-1,3-oxazol-2-yl]phenoxy}propyl)piperidine;
1-(3-{4-[4-(pyrrolidin-1-ylmethyl)-4,5-dihydro-1,3-oxazol-2-yl]phenoxy}propyl)piperidine;
8-benzyl-2-{4-[3-(2-methylpyrrolidin-1-yl)propoxy]phenyl}-3-oxa-1,8-diazaspiro[4.5]dec-1-ene;
8-cyclopentyl-2-{4-[3-(2-methylpyrrolidin-1-yl)propoxy]phenyl}-3-oxa-1,8-diazaspiro[4.5]dec-1-ene; and
5-[4-methyl-4-(piperidin-1-ylmethyl)-4,5-dihydro-1,3-oxazol-2-yl]-2-[3-(2-methylpyrrolidin-1-yl)propoxy]pyridine.

The "pharmaceutically acceptable salts" according to the invention include therapeutically active, non-toxic acid salt forms which the compounds of formula (I) are able to form.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic, and the like.

Conversely said salt forms can be converted into the free forms by treatment with an appropriate base.

Preferred salt forms are maleate, tartrate, fumarate, chlorhydrate, and trifluoroacetate.

Compounds of the formula (I) and their salts can be in the form of a solvate, which is included within the scope of the present invention. Such solvates include for example hydrates, alcoholates and the like.

Many of the compounds of formula (I) and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula (I) or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are included within the scope of the present invention.

The invention also includes within its scope prodrug forms of the compounds of formula (I) and its various sub-scopes and sub-groups.

The term "prodrug" as used herein includes compound forms which are rapidly transformed in vivo to the parent compound according to the invention, for example, by hydrolysis in blood. Prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialkysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

A. According to one embodiment, compounds of general formula (I) wherein $R^2$ is a group of formula (II) and $A^2$ is an oxygen atom, hereafter referred to as compounds of formula (Ib), may be obtained after several reaction steps via intermediates of formula (III) starting from compounds (VII) as shown in Scheme 1.

Scheme 1

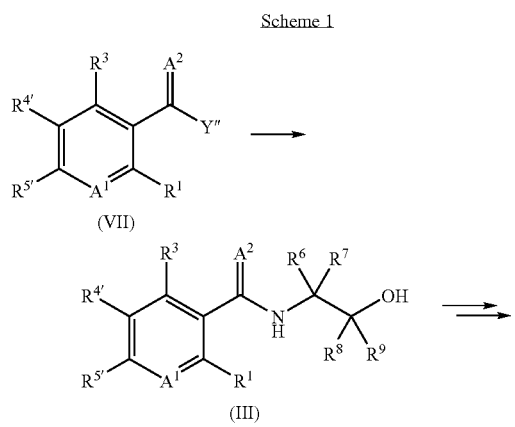

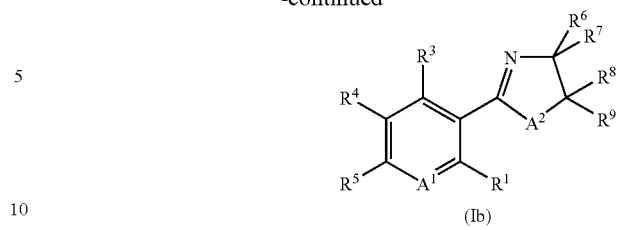

Usually, as shown in Scheme 2, the intermediate of formula (III) will undergo a cyclisation, in certain cases through an intermediate of formula (III'), leading to a compound of formula (Ia) or leading directly to a compound of formula (Ib). Compounds of formula (Ia) may be converted subsequently into compounds of formula (Ib) using a variety of conditions which will be detailed hereafter.

Scheme 2

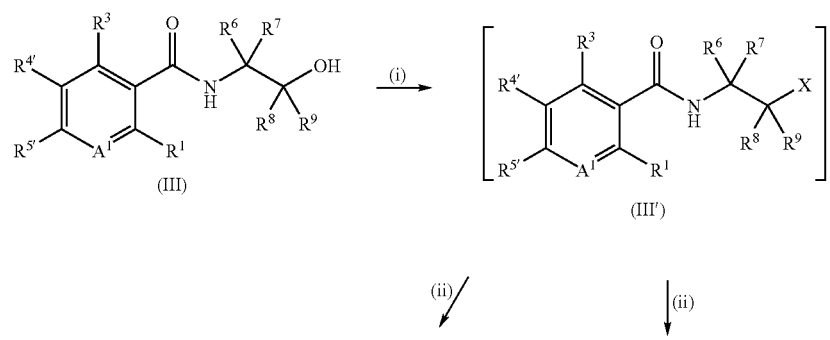

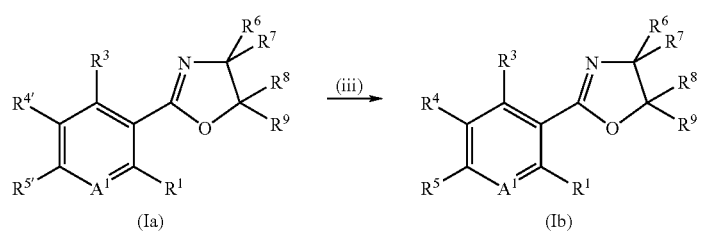

Unless specified otherwise:

For compounds of formula (III), (III'), (Ia) and (Ib), $A^1$, $R^1$, $R^3$, $R^6$, $R^7$, $R^8$ and $R^9$ and proviso for $R^6$, $R^7$, $R^8$ and $R^9$ are as defined above in the specification for compounds of formula (I). In compounds of formula (III'), X is a halogen atom, preferably chlorine, or a sulfonate group. The term "sulfonate group" as used herein represents a group of formula —O—$SO_2$—$R^f$ wherein $R^f$ is an alkyl or an aryl as defined hereabove in the specification. Preferred sulfonate groups are methanesulfonate or para-toluenesulfonate group.

When $A^1$ is CH in compounds of formula (III) and (III'), $R^{4'}$ is $R^4$ as defined above for compounds of formula (I); or —O—$(CH_2)_n$—Cl or —O—$CH_2$-phenyl; $R^{5'}$ is $R^5$ as defined above for compounds of formula (I); or —O—$(CH_2)_m$—Cl or —O—$CH_2$-phenyl; with the proviso that $R^{4'}$ is —O—$(CH_2)_n$—$NR^{12a}R^{12b}$ or —O—$(CH_2)_n$—Cl or —O—$CH_2$-phenyl, when $R^{5'}$ is hydrogen and that $R^{5'}$ is —O—$(CH_2)_m$—$NR^{13a}R^{13b}$, or —O—$(CH_2)_m$—Cl or —O—$CH_2$-phenyl, when $R^{4'}$ is hydrogen, halogen, $C_{1-4}$ alkyl, $C_{1-4}$ alkoxy, or trifluoromethyl;

When $A^1$ is CH in compounds of formula (Ia), $R^{4'}$ is hydroxy or —O—$(CH_2)_n$—Cl or —O—$CH_2$-phenyl; $R^{5'}$ is hydroxy or —O—$(CH_2)_m$—Cl or —O—$CH_2$-phenyl; with the proviso that $R^{4'}$ is —O—$(CH_2)_n$—Cl or —O—$CH_2$-phenyl or hydroxy, when $R^{5'}$ is hydrogen and that $R^{5'}$ is —O—$(CH_2)_m$—Cl, —O—$CH_2$-phenyl or hydroxy, when $R^{4'}$ is hydrogen, halogen, $C_{1-4}$ alkyl, $C_{1-4}$ alkoxy, or trifluoromethyl;

When $A^1$ is N in compounds of formula (III) and (III'), $R^{4'}$ is $R^4$ as defined above in the specification for compounds of formula (I) or —O—$(CH_2)_n$—Cl and $R^{5'}$ is $R^5$ as defined above in the specification for compounds of formula (I), or —O—$(CH_2)_m$—Cl or a halogen atom. When $R^{4'}$ or $R^{5'}$ is a halogen atom, it is preferably a chlorine atom.

For compounds of formula (Ib), $R^4$ and $R^5$ are as defined above in the specification for compounds of formula (I).

In a preferred embodiment, $A^1$ is CH in intermediates (III), (III'), (Ia) and (Ib).

Hereafter, references is made respectively to steps (i), (ii) and (iii) of Scheme 2.

Steps (i) and (ii): cyclisation may occur by reacting intermediates (III) with a cyclization agent such as thionyl chloride, (diethylamino)sulfur trifluoride, or Deoxo-fluor® according to methods described by Philipps et al. in Org. Lett. 2000, 2, 1165 and reference cited therein.

When $A^1$ is N, cyclisation may occur according to methods described by Dormoy et al. in Tetrahedron 1993, 49, 2885 or Zhang et al. in J. Med. Chem. 2002, 45, 2832. Preferably, when $A^1$ is N in intermediates (III), (III') and (Ia), $R^{4'}$ is H and $R^{5'}$ is a chlorine atom.

Conversion of compounds of formula (Ia) into compounds of formula (Ib), may occur in one or more steps, under a variety of reaction conditions depending on the nature of the $R^{4'}$ group, $R^{5'}$ group and $A^1$ group, according to conditions described hereafter in steps (iiia), (iiib), (iiic) (iiid) and (iiie):

Step (iiia): intermediates of formula (Ia) wherein $A^1$ is CH and $R^{4'}$ or $R^{5'}$ is —O—$CH_2$-phenyl may be converted to intermediates of same general formula as intermediates (Ia) wherein $R^{4'}$ or $R^{5'}$ is —OH, using a catalyst, for example palladium on charcoal (Pd/C or Pd(OH)$_2$/C), in the presence of a solvent such as methanol or ethanol under a hydrogen atmosphere.

Step (iiib): intermediates (Ia) wherein $A^1$ is CH and $R^{4'}$ or $R^{5'}$ is OH may be converted into intermediates (Ia), wherein $A^1$ is CH and $R^{4'}$ is —O—$(CH_2)_n$—Cl or $R^{5'}$ is —O—$(CH_2)_m$—Cl by reacting with a di-haloalkane respectively of general formula —Y—$(CH_2)_n$—Cl or Y—$(CH_2)_m$—Cl, wherein Y is a halogen except a fluorine, in the presence of a base. Preferably, Y is a bromine atom. This reaction may occur according to methods described by Walsh et al. in J. Med. Chem. 1989, 32, 105.

Step (iiic): intermediates (Ia) wherein $A^1$ is CH and $R^{4'}$ is —O—$(CH_2)_n$—Cl or $R^{5'}$ is —O—$(CH_2)_m$—Cl may react respectively with $HNR^{12a}R^{12b}$ or with $HNR^{13a}R^{13b}$ in the presence of a base such as triethylamine or potassium carbonate in acetonitrile or acetone as solvent, to afford compounds of formula (Ib). The reaction may be performed according to conventional methods known to the man skilled in the art.

Step (iiid): intermediates (Ia), wherein $A^1$ is a nitrogen atom, and $R^{4'}$ or $R^{5'}$ is a halogen atom, preferably a chlorine or a bromine atom, are reacted respectively with amino alcohols of formula HO—$(CH_2)_n$—$NR^{12a}R^{12b}$ or HO—$(CH_2)_m$—$NR^{13a}R^{13b}$ to afford compound (Ib) according to conventional methods known to the man skilled in the art. Alternatively a base, such as potassium tert-butylate, cesium carbonate or sodium hydride, with a solvent, such as dimethylformamide or tetrahydrofuran, in the presence of a palladium- or a copper-based catalyst, may be added, according to methods described by Penning et al. in J. Med. Chem. 2000, 43, 721.

Step (iiie): intermediates (Ia), wherein $A^1$ is CH, and $R^{4'}$ or $R^{5'}$ is a hydroxy group, are reacted respectively with amino alcohols of formula HO—$(CH_2)_n$—$NR^{12a}R^{12b}$ or HO—$(CH_2)_m$—$NR^{13a}R^{13b}$ to afford compound (Ib) according to conventional methods known to the man skilled in the art. Alternatively, diethylazodicarboxylate in the presence of triphenylphosphine in a solvent such as dichloromethane may be used.

Amino-alcohols HO—$(CH_2)_n$—$NR^{12a}R^{12b}$ and HO—$(CH_2)_m$—$NR^{13a}R^{13b}$ may be synthesized from the corresponding amino esters according to conventional methods known to the man skilled in the art, for example, by using a reducing agent such as lithium aluminium hydride in tetrahydrofuran as a solvent. Said amino esters are obtained from corresponding haloesters, according to methods described by G. Meier et al. in Eur. J. Pharm. Sci., C. 2001, 13, 249. Alternatively, said amino-alcohols may be prepared by reacting a β-halo-alcohol with an amine of formula $HNR^{12a}R^{12b}$ or $HNR^{13a}R^{13b}$.

B. Alternatively, compounds of formula (Ib) wherein $A^1$ is CH or a nitrogen atom and $R^6$ is H or a methyl group, $R^8$ and $R^9$ are hydrogen and $R^7$ is —$(CH_2)_v$—$NR^{14a}R^{14b}$ and v is 1, the other groups being defined as above in the specification for compounds of general formula (I), hereafter referred to as compound (Ic), may be synthesized from intermediates of formula (I), as shown in Scheme 3, Scheme 4 and Scheme 4'.

In compounds (IV), (V), (VI), (VIa) and (VIb), $R^1$ and $R^3$ are as defined above in the specification for compounds of formula (I). In compounds (IV), (V) and (VI), $R^{4'}$ and $R^{5'}$ are as defined above in the specification respectively for $R^4$ and $R^5$ in compounds of formula (I), except that $R^{4'}$ cannot be a chlorine atom. In compounds (VIa) and (VIb), $R^4$ and $R^5$ are as defined for compounds of general formula (I).

R' is a $C_{1-4}$ alkyl, preferably a methyl.

Y' is a halogen atom, preferably a chlorine atom; or a sulfonate group, preferably a methanesulfonate or para-toluenesulfonate.

In following Schemes 3 and 4, $A^1$ is CH, $R^{4'}$ is preferably a hydrogen atom and $R^{5'}$ is preferably $—O—(CH_2)m—NR^{13a}R^{13b}$.

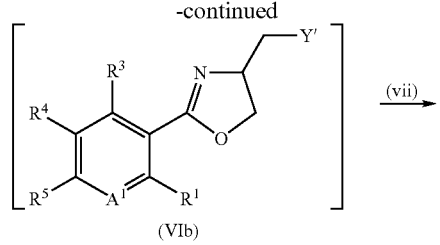

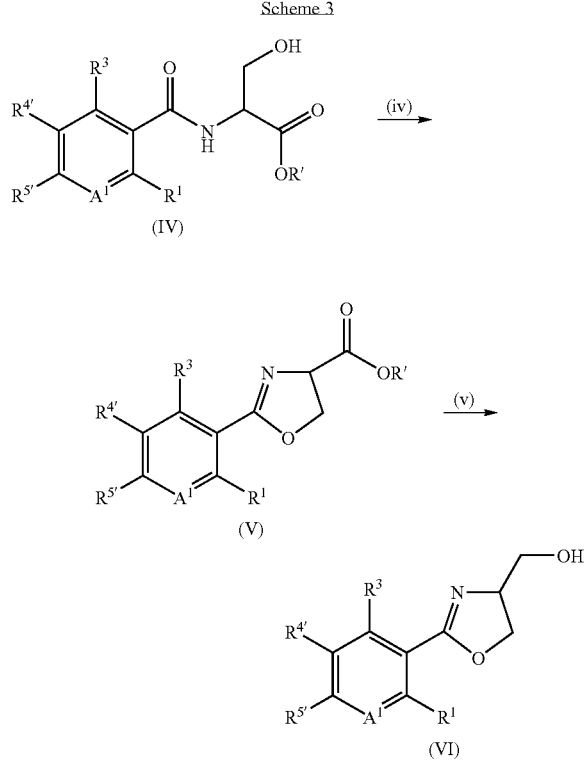

Hereafter, reference is made respectively to steps (iv) and (v) of Scheme 3.

Step (iv): intermediates of formula (V) are obtained by reacting intermediates of formula (IV) according to methods described above in steps (i) and (ii) of Scheme 2.

Step (v): intermediate of formula (V) is subsequently reacted with a reducing agent, for example sodium borohydride or lithium borohydride, according to conventional methods known to the man skilled in the art.

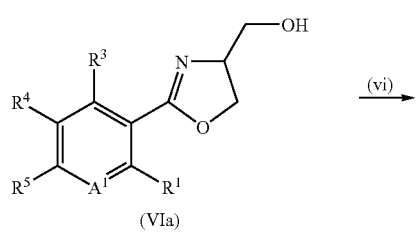

Hereafter, reference is made respectively to steps (vi) and (vii) of Scheme 4.

Steps (vi) and (vii): intermediates (VIa) are reacted with an activating agent, for example methanesulfonyl chloride, in the presence of a base such as triethylamine, and are further reacted with $HNR^{14a}R^{14b}$ to afford compounds (Ic) according to methods described by Kline et al. in J. Med. Chem., 2002, 45, 3112. The intermediate compounds (VIb) may be isolated or immediately engaged in step (vii).

Alternatively, compounds of formula (Ic) wherein $A^1$ is a nitrogen atom, $R^{4'}$H and $R^{5'}$ are as defined above in the specification respectively for $R^4$ and $R^5$, $R^6$ is H or a methyl group, $R^8$ and $R^9$ are hydrogen and $R^7$ is $—(CH_2)_v—NR^{14a}R^{14b}$ and v is 1, the other groups being defined as above in the specification for compounds of general formula (I), may be synthesized from intermediates of formula (VIa), as shown in Scheme 4'.

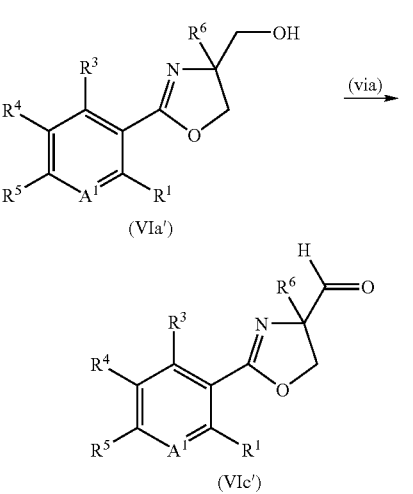

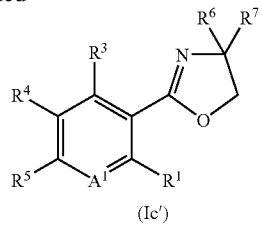

(Ic')

Hereafter, reference is made respectively to steps (via) and (viia) of Scheme 4'.

Step (via): intermediates of formula (VIa') are reacted with an oxidizing agent, such as oxalyl chloride, in the presence of dimethylsulfoxide and triethylamine in a solvent such as dichloromethane, according to conventional methods known to the man skilled in the art to afford compounds of formula (VIc').

Step (viia): compounds of formula (VIc') are reacted with $HNR^{14a}R^{14b}$ in the presence of a reducing agent, such as sodium triacetoxyborohydride in a solvent such as dichloromethane, according to conventional methods known to the man skilled in the art to afford compounds (Ic').

Compounds of formula (VIa), wherein $A^1$ is a nitrogen atom, $R^{4'}$ is a chlorine or $R^{5'}$ is a bromine, are reacted respectively with amino alcohols of formula $HO-(CH_2)_n-NR^{12a}R^{12b}$ or $HO-(CH_2)_m-NR^{13a}R^{13b}$ to afford compound (VIa), wherein $R^{4'}$ is $R^4$ and $R^{5'}$ is $R^5$ as defined above in the specification respectively, according to methods described in steps (iiid) of Scheme 2.

C. Intermediates of formula (III) may be synthesized according to the reaction of Scheme 5 or alternatively according to the reaction of Scheme 7.

Unless otherwise specified, groups in compounds (VII) and (VIII) having the same reference as groups in intermediates (III) are as defined above in the specification for intermediates (III). Y″ is a hydroxy or a halogen, which halogen is preferably a chlorine atom.

Scheme 5

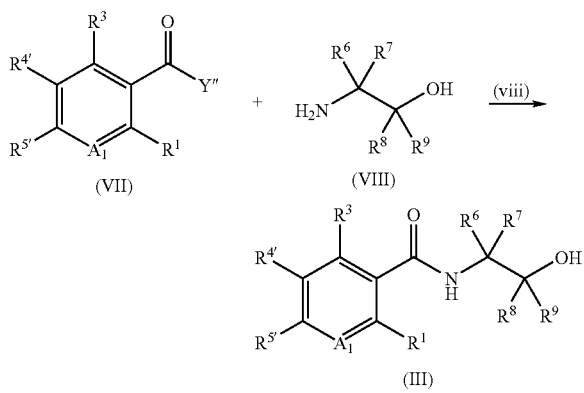

Hereafter, reference is made to step (viii) of Scheme 5.

When Y″ is a hydroxy group, compounds (VII) and (VIII) are reacted in the presence of a coupling agent, for example 1-(3-dimethylaminopropyl)-3-ethylcarbodiimide hydrochloride and an activating agent, for example N-hydroxy-benzotriazole, according to conventional methods known to the man skilled in the art.

Alternatively, compounds (VII) wherein Y″ is a hydroxy group may be transformed to the corresponding acyl chloride using conventional methods known to the man skilled in the art, such as thionyl chloride, to provide compound (VII) wherein Y″ is a chlorine atom, which compounds (VII) is then reacted with (VIII) in the presence of a base, such as triethylamine, to afford intermediate (III).

In another embodiment, the reaction conditions described above in step (viii) can be applied to compound (VII), wherein $A^1$ is a nitrogen atom, $R^{4'}$ is hydrogen and $R^{5'}$ is a chlorine atom.

Compounds (VII) wherein $R^{4'}$ is $-O-(CH_2)_n-NR^{12a}R^{12b}$ or $R^{5'}$ $-O-(CH_2)_m-NR^{13a}R^{13b}$, and Y″ is a hydroxy may be obtained by hydrolysis of the corresponding ester intermediates of formula (VII), wherein Y″ is $C_{1-4}$ alkoxy, preferably a methoxy, according to conventional methods known to the man skilled in the art.

Said ester intermediates of formula (VII), wherein $R^{4'}$ and $R^{5'}$ are as described above, hereafter referred to as compound (VII), may be obtained according to Scheme 6.

Scheme 6

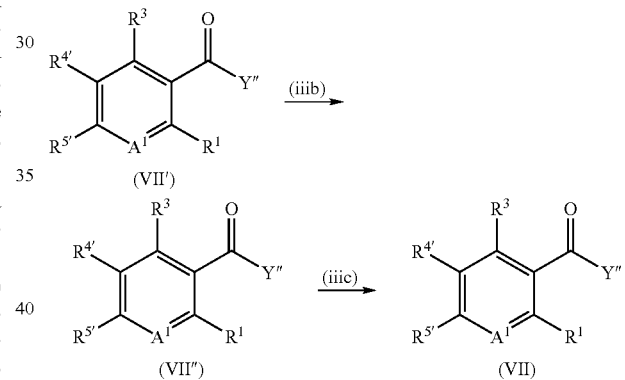

Hereafter, reference is made respectively to step (iiib) and step (iiic) of Scheme 6.

Intermediates (VII) may be obtained from the reaction of the corresponding esters (VII″), wherein $R^{4'}$ is $-O-(CH_2)_n-Cl$ or $R^{5'}-O-(CH_2)_m-Cl$, respectively with an amine of formula $HNR^{12a}R^{12b}$ or $HNR^{13a}R^{13b}$ as described above in the specification for step (iiic) of Scheme 2.

Ester intermediates (VII″) may in turn be prepared from compounds (VII') wherein $R^{4'}$ or $R^{5'}$ is —OH, by reacting (VII') with a di-haloalkane respectively of general formula $-Y-(CH_2)_n-Cl$ or $Y-(CH_2)_m-Cl$, as described above in the specification for step (iiib) of Scheme 2.

Unless otherwise specified, groups in intermediates (VII), (VII') and (VII″) having the same reference as groups in intermediates (III) are as defined for intermediates (III).

Some compounds (VIII) are commercially available or are obtained by reaction of the corresponding amino-esters with a reducing agent, for example, lithium borohydride, according to conventional methods known to the man skilled in the art.

Intermediates (IV) may be obtained by reacting a compounds of formula (VII) with compounds of formula (VIII), wherein $R^6$, $R^8$ and $R^9$ are hydrogen and $R^7$ is —COOR', according to conditions described in Scheme 4 for intermediates (III).

In another particular embodiment, $A^1$ is a nitrogen atom, $R^6$ is a methyl group, $R^8$ and $R^9$ are hydrogen and $R^7$ is —CH$_2$—OH, according to conditions described in Scheme 4' for intermediates (III).

In a particular embodiment according to the invention, intermediates (III) wherein $A^1$ is CH, $R^8$ and $R^9$ are hydrogen and $R^6$ and $R^7$ are linked together to form a $C_{2-8}$ alkylene, in which one methylene is optionally replaced by a nitrogen atom, which nitrogen atom is optionally substituted by arylalkyl or $C_{1-8}$ alkyl, may be obtained according to Scheme 7.

Unless otherwise specified, groups in intermediates (IX) and (X) having the same reference as groups in intermediates (III) are as defined for intermediates (III). $R^1$ is a $C_{1-4}$ alkyl, preferably a methyl.

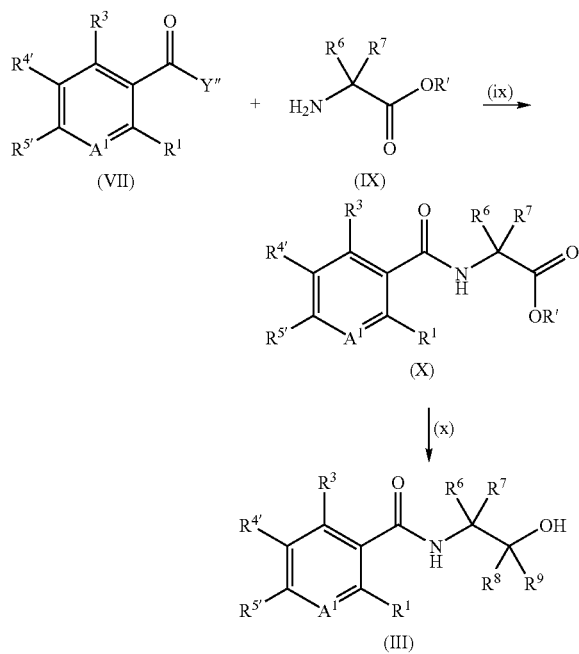

Hereafter, reference is made respectively to step (ix) and step (x) of Scheme 7.

Step (ix): Conditions for step (ix) in Scheme 7 are as described above in the specification for step (viii) of Scheme 5.

Step (x): Intermediates of formula (X) are reacted with a reducing agent, according to the method described in Scheme 3 for the step (v).

Amino-esters (IX) are commercially available or may be obtained from the commercially available corresponding amino-acids according to conventional methods known to the man skilled in the art. Alternatively, amino-esters (IX) may be synthesized according to methods described by Albert, J. S. et al. in J. Med. Chem. 2002, 45, 3972.

D. The man skilled in the art will apply, when appropriate, any of the methods described in Schemes 2 to 7 to synthesize compounds of formula (I) wherein $A^2$ is O and $R^2$ is (II), to the synthesis of compounds of formula (I) wherein $R^2$ is (II) and $A^2$ is sulfur.

Alternatively, said compounds hereafter referred to as compounds of formula (Ic'), may be obtained according to Scheme 8 from intermediate (III).

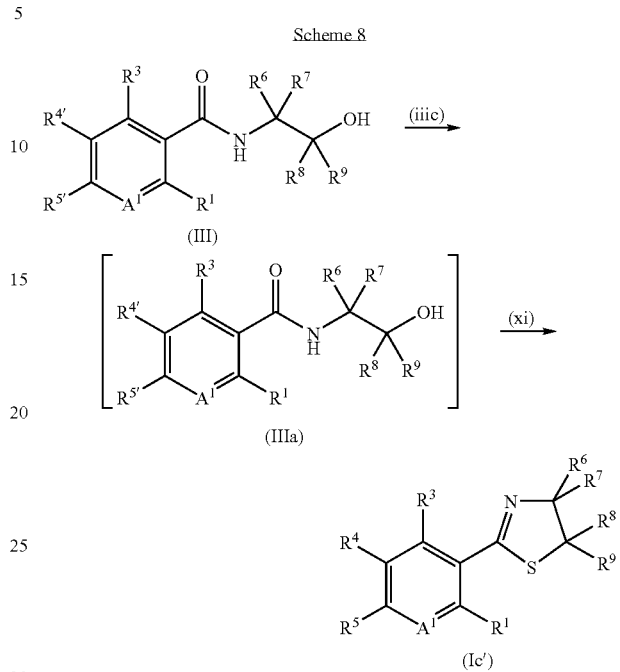

Hereafter, reference is made respectively to steps (iiic) and step (xi) of Scheme 8.

Intermediates (III) wherein $R^{4'}$ is —O—(CH$_2$)$_n$—Cl and $R^{5'}$ is —O—(CH$_2$)$_m$—Cl may be converted to intermediate (IIIa) wherein $R^{4'}$ and $R^{5'}$ are as defined respectively for $R^4$ and $R^5$ above in the specification for compounds of formula (I), according to conditions described in steps (iiia-c) described above in Scheme 2.

Step (xi): intermediates of formula (IIIa) may be converted to compounds of formula (Ic') by reacting with a sulfur-releasing agent, such as Lawesson's reagent described in T. Nishio et al. J. Org. Chem. 1997, 62, 1106 or by any other conventional methods known to the man skilled in the art.

Unless otherwise specified, preferred groups, more preferred and most preferred $R^1$, $R^2$, $R^3$, $R^4$, $R^5$, $R^6$, $R^7$, $R^8$, $R^9$, $R^{12a}$, $R^{12b}$, $R^{13a}$, $R^{13b}$, $R^{14a}$ and $R^{14b}$ groups of compounds represented in Schemes 2 to 8 are as defined above in the specification for compounds of general formula (I).

E. According to another embodiment, some compounds of general formula (I) may be prepared by functional group transformation.

E.1 Compounds of formula (Ib) wherein $A^1$ is CH, $R^1$, $R^2$, $R^3$, $R^4$, $R^5$, $R^{12a}$, $R^{12b}$, $R^{13a}$, $R^{13b}$, $R^{14a}$ and $R^{14b}$ groups are as defined above in the specification for compounds of general formula (I), $R^8$ and $R^9$ are hydrogen and $R^6$ and $R^7$ are linked together to form a $C_{2-8}$ alkylene, in which one methylene is optionally replaced by a nitrogen atom, which nitrogen atom is optionally substituted by arylalkyl or $C_{1-8}$ alkyl, may be obtained from compounds of formula (Ib) wherein the above nitrogen atom substituted by a benzyl group, is deprotected by using conventional methods known to the man skilled in the art. The corresponding NH function obtained by such reaction is then submitted to a $C_{1-8}$ alkyl halide, preferably a cyclopentylbromide, in the presence of a base, such as potassium carbonate in acetonitrile to afford compounds (Ib).

E.2 Compounds of formula (Ib) wherein $A^1$ is CH, $R^1$, $R^2$, $R^3$, $R^5$, $R^{12a}$, $R^{12b}$, $R^{13a}$, $R^{13b}$, $R^{14a}$ and $R^{14b}$ groups are as defined above in the specification for compounds of general formula (I), $R^4$ is a halogen, preferably a bromide may be obtained by treating compounds of formula (Ib), wherein $R^4$ is a hydrogen, with a base such as n-butyllithium and a halogen-releasing agent such as bromine, in tetrahydrofuran at low temperature.

In a particular embodiment, the present invention relates to a synthetic intermediate compound of formula (III), geometrical isomers, enantiomers, diastereoisomers, pharmaceutically acceptable salts and all possible mixtures thereof,

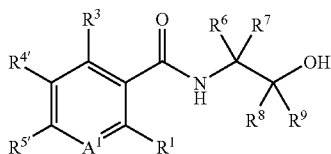

(III)

wherein $A^1$ is CH, C(CH$_3$) or N;

$R^1$ is hydrogen or halogen;

$R^3$ is hydrogen, halogen, $C_{1-4}$ alkyl or $C_{1-4}$ alkoxy;

$R^{4'}$ is hydrogen, halogen, $C_{1-4}$ alkyl, $C_{1-4}$ alkoxy, trifluoromethyl, —O—CH$_2$-phenyl; or —O—(CH$_2$)$_n$—Cl or —O—(CH$_2$)$_n$—NR$^{12a}$R$^{12b}$;

$R^{5'}$ is hydrogen, halogen, —O—CH$_2$-phenyl, —O—(CH$_2$)$_m$—Cl or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl;

$R^6$ is hydrogen or $C_{1-4}$ alkyl; or $R^6$ and $R^7$ are linked together to form a $C_{2-8}$ alkylene in which one methylene of the alkylene is optionally replaced by a nitrogen atom which nitrogen atom is optionally substituted by an arylalkyl or $C_{1-8}$ alkyl;

$R^7$ is hydrogen, $C_{1-8}$ alkyl, aryl, arylalkyl, or —(CH$_2$)$_v$—NR$^{14a}$R$^{14b}$; or $R^6$ and $R^7$ are linked together to form a $C_{2-8}$ alkylene in which one methylene of the alkylene is optionally replaced by a nitrogen atom which nitrogen atom is optionally substituted by arylalkyl or $C_{1-8}$ alkyl; or $R^7$ and $R^9$ are linked together to form a $C_{3-6}$ alkylene;

$R^8$ is hydrogen; or $R^8$ and $R^9$ are linked together to form a $C_{2-8}$ alkylene;

$R^9$ is hydrogen or aryl; or $R^7$ and $R^9$ are linked together to form a $C_{3-6}$ alkylene; or $R^8$ and $R^9$ are linked together to form a $C_{2-8}$ alkylene;

$R^{12a}$ and $R^{12b}$ are linked together to form a $C_{3-6}$ alkylene, each methylene of the alkylene being optionally substituted by a $C_{1-4}$ alkyl;

$R^{13a}$ and $R^{13b}$ are linked together to form a $C_{3-6}$ alkylene, each methylene of the alkylene being optionally substituted by a $C_{1-4}$ alkyl, an amino group or an aminoalkyl, one methylene of the alkylene being optionally replaced by a nitrogen atom, said nitrogen atom being optionally substituted by a $C_{1-8}$ alkyl or an aminoalkyl;

$R^{14a}$ and $R^{14b}$ are linked together to form a $C_{3-6}$ alkylene, each methylene of the alkylene being optionally substituted by a $C_{1-4}$ alkyl;

n and m are independently an integer comprised between 2 and 8;

v is an integer comprised between 1 and 4;

with the proviso that $R^{4'}$ is —O—(CH$_2$)$_n$—NR$^{12a}$R$^{12b}$, —O—(CH$_2$)$_n$—Cl, or —O—CH$_2$-phenyl when $R^{5'}$ is hydrogen and that $R^{5'}$ is —O—(CH$_2$)$_m$—NR$^{13a}$R$^{13b}$, —O—(CH$_2$)$_m$—Cl, or —O—CH$_2$-phenyl when $R^{4'}$ is hydrogen, halogen, $C_{1-4}$ alkyl, $C_{1-4}$ alkoxy or trifluoromethyl;

with the proviso that at least one of $R^6$, $R^7$, $R^8$ and $R^9$ is different from H; and with the proviso that said compound of formula (III) is different from 4-(benzyloxy)-N-(2-hydroxy-1,1-dimethylethyl)benzamide and 6-chloro-N-(2-hydroxy-1,1-dimethylethyl)nicotinamide.

In a particular embodiment, the present invention relates to a compound of formula (III) wherein when $R^6$ and $R^7$ are not linked together $R^6$ is different from $R^7$.

In another particular embodiment, the present invention relates to a compound of formula (III) wherein $R^{4'}$ is hydrogen, halogen, $C_{1-4}$ alkyl, $C_{1-4}$ alkoxy, trifluoromethyl or —O—(CH$_2$)$_n$—Cl or —O—(CH$_2$)$_n$—NR$^{12a}$R$^{12b}$; and $R^{5'}$ is hydrogen, halogen, —O—(CH$_2$)$_m$—Cl or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl.

Preferably, $A^1$ is CH or C(CH$_3$). More preferably, $A^1$ is CH.

In another particular embodiment, the present invention relates to a synthetic intermediate compound of formula (IV), geometrical isomers, enantiomers, diastereoisomers, pharmaceutically acceptable salts and all possible mixtures thereof,

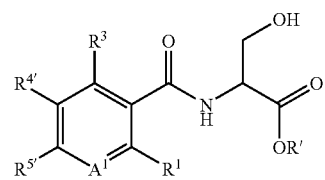

(IV)

wherein $A^1$ is CH, C(CH$_3$) or N;

R' is $C_{1-4}$ alkyl;

$R^1$ is hydrogen or halogen;

$R^3$ is hydrogen, halogen, $C_{1-4}$ alkyl or $C_{1-4}$ alkoxy;

$R^{4'}$ is hydrogen, $C_{1-4}$ alkyl, $C_{1-4}$ alkoxy, trifluoromethyl or —O—(CH$_2$)$_n$—NR$^{12a}$R$^{12b}$;

$R^{5'}$ is hydrogen or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl;

$R^{12a}$ and $R^{12b}$ are linked together to form a $C_{3-6}$ alkylene, each methylene of the alkylene being optionally substituted by a $C_{1-4}$ alkyl;

$R^{13a}$ and $R^{13b}$ are linked together to form a $C_{3-6}$ alkylene, each methylene of the alkylene being optionally substituted by a $C_{1-4}$ alkyl, an amino group or an aminoalkyl, one methylene of the alkylene being optionally replaced by a nitrogen atom, said nitrogen atom being optionally substituted by a $C_{1-8}$ alkyl or an aminoalkyl;

n and m are independently an integer comprised between 2 and 8; and with the proviso that $R^{4'}$ is —O—(CH$_2$)$_n$—NR$^{12a}$R$^{12b}$ when $R^{5'}$ is hydrogen and that $R^{5'}$ is —O—(CH$_2$)$_m$—NR$^{13a}$R$^{13b}$ when $R^{4'}$ is hydrogen, $C_{1-4}$ alkyl, $C_{1-4}$ alkoxy or trifluoromethyl.

Preferably, R' is methyl.

Preferably, $A^1$ is CH or C(CH$_3$). More preferably, $A^1$ is CH.

Preferably, $R^{4'}$ is hydrogen and $R^{5'}$ is —O—(CH$_2$)$_m$—NR$^{13a}$R$^{13b}$.

In another particular embodiment, the present invention relates to a synthetic intermediate compound of formula (V), geometrical isomers, enantiomers, diastereoisomers, pharmaceutically acceptable salts and all possible mixtures thereof,

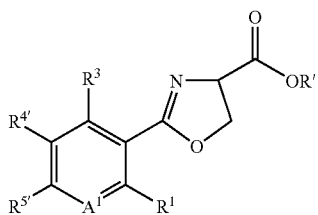

(V)

wherein
$A^1$ is CH, C(CH$_3$) or N;
R' is $C_{1-4}$ alkyl;
$R^1$ is hydrogen or halogen;
$R^3$ is hydrogen, halogen, $C_{1-4}$ alkyl or $C_{1-4}$ alkoxy;
$R^{4'}$ is hydrogen, $C_{1-4}$ alkyl, $C_{1-4}$ alkoxy, trifluoromethyl or —O—(CH$_2$)$_n$—NR$^{12a}$R$^{12b}$;
$R^{5'}$ is hydrogen or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl;
$R^{12a}$ and $R^{12b}$ are linked together to form a $C_{3-6}$ alkylene, each methylene of the alkylene being optionally substituted by a $C_{1-4}$ alkyl;
$R^{13a}$ and $R^{13b}$ are linked together to form a $C_{3-6}$ alkylene, each methylene of the alkylene being optionally substituted by a $C_{1-4}$ alkyl, an amino group or an aminoalkyl, one methylene of the alkylene being optionally replaced by a nitrogen atom, said nitrogen atom being optionally substituted by a $C_1$ g alkyl or an aminoalkyl;
n and m are independently an integer comprised between 2 and 8; and
with the proviso that $R^{4'}$ is —O—(CH$_2$)$_n$—NR$^{12a}$R$^{12b}$ when $R^{5'}$ is hydrogen and that $R^{5'}$ is —O—(CH$_2$)$_m$—NR$^{13a}$R$^{13b}$ when $R^{4'}$ is hydrogen, $C_{1-4}$ alkyl, $C_{1-4}$ alkoxy or trifluoromethyl.

Preferably, $A^1$ is CH or C(CH$_3$). More preferably, $A^1$ is CH.
Preferably, $R^{4'}$ is hydrogen and $R^{5'}$ is —O—(CH$_2$)$_m$—NR$^{13a}$R$^{13b}$.

In another particular embodiment, the present invention relates to a synthetic intermediate compound of formulae (VI), geometrical isomers, enantiomers, diastereoisomers, pharmaceutically acceptable salts and all possible mixtures thereof

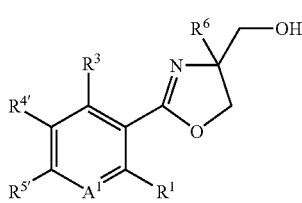

(VI)

wherein
$A^1$ is CH, C(CH$_3$) or N;
$R^1$ is hydrogen or halogen;
$R^3$ is hydrogen, halogen, $C_{1-4}$ alkyl or $C_{1-4}$ alkoxy;
$R^{4'}$ is hydrogen, $C_{1-4}$ alkyl, $C_{1-4}$ alkoxy, trifluoromethyl or —O—(CH$_2$)$_n$—NR$^{12a}$R$^{12b}$;
$R^{5'}$ is hydrogen or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl;
$R^6$ is hydrogen or methyl;
$R^{12a}$ and $R^{12b}$ are linked together to form a $C_{3-6}$ alkylene, each methylene of the alkylene being optionally substituted by a $C_{1-4}$ alkyl;
$R^{13a}$ and $R^{13b}$ are linked together to form a $C_{3-6}$ alkylene, each methylene of the alkylene being optionally substituted by a $C_{1-4}$ alkyl, an amino group or an aminoalkyl, one methylene of the alkylene being optionally replaced by a nitrogen atom, said nitrogen atom being optionally substituted by a $C_{1-8}$ alkyl or an aminoalkyl;
n and m are independently an integer comprised between 2 and 8; and
with the proviso that $R^{4'}$ is —O—(CH$_2$)$_n$—NR$^{12a}$R$^{12b}$ when $R^{5'}$ is hydrogen and that $R^{5'}$ is —O—(CH$_2$)$_m$—NR$^{13a}$R$^{13b}$ when $R^{4'}$ is hydrogen, $C_{1-4}$ alkyl, $C_{1-4}$ alkoxy or trifluoromethyl.

Preferably, $R^{4'}$ is hydrogen and $R^{5'}$ is —O—(CH$_2$)—NR$^{13a}$R$^{13b}$.

In another particular embodiment, the present invention relates to a synthetic intermediate compound of formula (VII), geometrical isomers, enantiomers, diastereoisomers, pharmaceutically acceptable salts and all possible mixtures thereof,

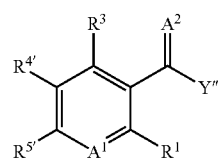

(VII)

wherein
$A^1$ is CH, C(CH$_3$) or N;
$A^2$ is O or S;
Y" is halogen, hydroxy or $C_{1-4}$ alkoxy;
$R^1$ is hydrogen or halogen;
$R^3$ is hydrogen, halogen, $C_{1-4}$ alkyl or $C_{1-4}$ alkoxy;
$R^{4'}$ is hydrogen, halogen, $C_{1-4}$ alkyl, $C_{1-4}$ alkoxy, trifluoromethyl, —O—CH$_2$-phenyl; or —O—(CH$_2$)$_n$—Cl or —O—(CH$_2$)$_n$—NR$^{12a}$R$^{12b}$;
$R^{5'}$ is hydrogen, halogen, —O—CH$_2$-phenyl, —O—(CH$_2$)$_m$—Cl or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl;
$R^{12a}$ and $R^{12b}$ are linked together to form a $C_{3-6}$ alkylene, each methylene of the alkylene being optionally substituted by a $C_{1-4}$ alkyl;
$R^{13a}$ and $R^{13b}$ are linked together to form a $C_{3-6}$ alkylene, each methylene of the alkylene being optionally substituted by a $C_{1-4}$ alkyl, an amino group or an aminoalkyl, one methylene of the alkylene being optionally replaced by a nitrogen atom, said nitrogen atom being optionally substituted by a $C_{1-8}$ alkyl or an aminoalkyl;
n and m are independently an integer comprised between 2 and 8;
with the proviso that $R^{4'}$ is —O—(CH$_2$)$_n$—NR$^{12a}$R$^{12b}$, —O—(CH$_2$)$_n$—Cl, or —O—CH$_2$-phenyl when $R^{5'}$ is hydrogen and that $R^{5'}$ is —O—(CH$_2$)$_m$—NR$^{13a}$R$^{13b}$, —O—(CH$_2$)$_m$—Cl, or —O—CH$_2$-phenyl when $R^{4'}$ is hydrogen, halogen, $C_{1-4}$ alkyl, $C_{1-4}$ alkoxy or trifluoromethyl; and with the proviso that said compound of formula (VII) is different from methyl 4-(3-chloropropoxy)benzoate, 4-(3-chloropropoxy)benzoic acid, 4-(3-chloropropoxy)benzoyl-chloride, methyl 3-(3-chloropropoxy)benzoate, methyl 4-(3-piperidin-1-ylpropoxy)benzoate, methyl 3-(3-piperidin-1-ylpropoxy)benzoate, methyl 4-(3-pyrrolidin-1-ylpropoxy) benzoate), 4-(3-piperidin-1-ylpropoxy)benzoic acid and 4-(3-pyrrolidin-1-ylpropoxy)benzoic acid.

Preferably, $A^1$ is CH or C(CH$_3$). More preferably, $A^1$ is CH.
Preferably, $A^2$ is O.

Y″ is preferably a hydroxy, a chlorine atom or a methoxy.

In another particular embodiment, the present invention relates to a synthetic intermediate compound of formula (Ia) geometrical isomers, enantiomers, diastereoisomers, pharmaceutically acceptable salts and all possible mixtures thereof,

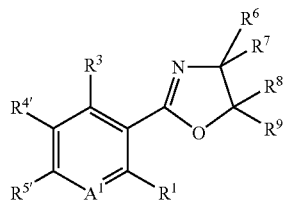

(Ia)

wherein,
$A^1$ is CH, C(CH$_3$) or N;
$R^1$ is hydrogen or halogen;
$R^3$ is hydrogen, halogen, C$_{1-4}$ alkyl or C$_{1-4}$ alkoxy;
$R^{4'}$ is hydrogen, halogen, C$_{1-4}$ alkyl, C$_{1-4}$ alkoxy, trifluoromethyl, hydroxy, —O—CH$_2$-phenyl, or —O—(CH$_2$)$_n$—Cl;
$R^{5'}$ is hydrogen, halogen, hydroxy, —O—CH$_2$-phenyl, or —O—(CH$_2$)$_m$Cl;
$R^6$ is hydrogen or C$_{1-4}$ alkyl; or $R^6$ and $R^7$ are linked together to form a C$_{2-8}$ alkylene in which one methylene of the alkylene is optionally replaced by a nitrogen atom which nitrogen atom is optionally substituted by an arylalkyl or C$_{1-8}$ alkyl;
$R^7$ is hydrogen, C$_{1-8}$ alkyl, aryl, arylalkyl, or —(CH$_2$)$_v$—NR$^{14a}$R$^{14b}$; or $R^6$ and $R^7$ are linked together to form a C$_{2-8}$ alkylene in which one methylene of the alkylene is optionally replaced by a nitrogen atom which nitrogen atom is optionally substituted by arylalkyl or C$_{1-8}$ alkyl; or $R^7$ and $R^9$ are linked together to form a C$_{3-6}$ alkylene;
$R^8$ is hydrogen; or $R^8$ and $R^9$ are linked together to form a C$_{2-8}$ alkylene;
$R^9$ is hydrogen or aryl; or $R^7$ and $R^9$ are linked together to form a C$_{3-6}$ alkylene; or $R^8$ and $R^9$ are linked together to form a C$_{2-8}$ alkylene;
$R^{14a}$ and $R^{14b}$ are linked together to form a C$_{3-6}$ alkylene, each methylene of the alkylene being optionally substituted by a C$_{1-4}$ alkyl;
v is an integer comprised between 1 and 4;
with the proviso that $R^{4'}$ is —O—(CH$_2$)$_n$—Cl or —O—CH$_2$-phenyl or hydroxy, when $R^{5'}$ is hydrogen and that $R^{5'}$ is —O—(CH$_2$)$_m$—Cl, —O—CH$_2$-phenyl or hydroxy, when $R^{4'}$ is hydrogen, halogen, C$_{1-4}$ alkyl, C$_{1-4}$ alkoxy, or trifluoromethyl;
with the proviso that at least one of $R^6$, $R^7$, $R^8$ and $R^9$ is different from H; and
with the proviso that said compound of formula (Ia) is different from 2-[3-(benzyloxy)phenyl]-4,4-dimethyl-4,5-dihydro-1,3-oxazole, (4,4-dimethyl-4,5-dihydro-1,3-oxazol-2-yl)phenol, 2-chloro-5-(4,4-dimethyl-4,5-dihydro-1,3-oxazol-2-yl)pyridine and 2-[4-(benzyloxy)phenyl]-4,4-dimethyl-4,5-dihydro-1,3-oxazole and 4-(4,4-dimethyl-4,5-dihydro-1,3-oxazol-2-yl)phenol.

In a particular embodiment, the present invention relates to a compound of formula (Ia) wherein when $R^6$ and $R^7$ are not linked together $R^6$ is different from $R^7$.

Preferably, $A^1$ is CH.

In another particular embodiment, the present invention relates to compounds of formula (Ia) wherein
$R^{4'}$ is hydrogen, halogen, C$_{1-4}$ alkyl, C$_{1-4}$ alkoxy, trifluoromethyl or —O—(CH$_2$)$_n$—Cl and $R^{5'}$ is hydrogen, halogen or —O—(CH$_2$)$_m$—Cl, provided that $R^{4'}$ is —O—(CH$_2$)$_n$—Cl when $R^{5'}$ is hydrogen and that $R^{5'}$ is —O—(CH$_2$)$_m$—Cl when $R^{4'}$ is hydrogen, halogen, C$_{1-4}$ alkyl, C$_{1-4}$ alkoxy, or trifluoromethyl.

In a particular aspect, the present invention relates to compounds of general formula (Ib),

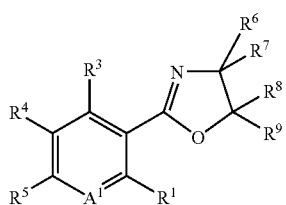

(Ib)

wherein $A^1$, $R^1$, $R^3$, $R^4$, $R^5$, $R^6$, $R^7$, $R^8$, $R^9$ and provisos are as defined above in the specification for compounds of formula (I).

In another particular aspect, the present invention relates to compounds of general formula (Ic),

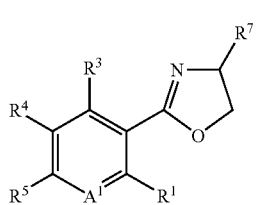

(Ic)

wherein $A^1$, $R^1$, $R^3$, $R^4$, $R^5$, $R^7$ and provisos are as defined above in the specification for compounds of formula (I).

In a further embodiment, the invention relates to a synthetic intermediate compound selected from the group consisting of:
4-[(benzyloxy)methyl]-N-[1-(hydroxymethyl)cyclohexyl] benzamide;
3-(benzyloxy)-N-(2-hydroxy-1,1-dimethylethyl)benzamide;
N-(2-hydroxy-1-methyl-2-phenylethyl)-4-(3-piperidin-1-yl-propoxy)benzamide;
N-[1-(hydroxymethyl)cyclohexyl]-4-(3-piperidin-1-ylpropoxy)benzamide;
N-[1-(hydroxymethyl)cyclohexyl]-3-(3-piperidin-1-ylpropoxy)benzamide;
N-[1-(hydroxymethyl)cyclohexyl]-4-[3-(2-methylpiperidin-1-yl)propoxy]benzamide;
N-[1-(hydroxymethyl)cyclohexyl]-4-(3-pyrrolidin-1-ylpropoxy)benzamide;
N-[1-(hydroxymethyl)cyclohexyl]-3-(3-pyrrolidin-1-ylpropoxy)benzamide;

N-[1-(hydroxymethyl)-3-pyrrolidin-1-ylpropyl]-4-(3-piperidin-1-ylpropoxy)benzamide;
N-[1-(hydroxymethyl)cyclopropyl]-4-(3-piperidin-1-ylpropoxy)benzamide;
N-(1-benzyl-2-hydroxyethyl)-4-(3-piperidin-1-ylpropoxy)benzamide;
N-(2-hydroxy-1,1-dimethylethyl)-4-(3-piperidin-1-ylpropoxy)benzamide;
N-[1-(hydroxymethyl)-2,2-dimethylpropyl]-4-[3-(2-methylpyrrolidin-1-yl)propoxy]benzamide;
N-[(1R,2R)-2-hydroxycyclohexyl]-4-[3-(2-methylpyrrolidin-1-yl)propoxy]benzamide;
N-(2-hydroxy-1-phenylethyl)-4-[3-(2-methylpyrrolidin-1-yl)propoxy]benzamide;
N-[2-cyclohexyl-1-(hydroxymethyl)ethyl]-4-[3-(2-methylpyrrolidin-1-yl)propoxy]benzamide;
6-chloro-N-[1-(hydroxymethyl)cyclohexyl]nicotinamide;
4-(3-chloropropoxy)-N-(2-hydroxy-1,1-dimethylethyl)benzamide;
methyl N-[4-(3-piperidin-1-ylpropoxy)benzoyl]serinate;
methyl 2-[4-(3-piperidin-1-ylpropoxy)phenyl]-4,5-dihydro-1,3-oxazole-4-carboxylate;
{2-[4-(3-piperidin-1-ylpropoxy)phenyl]-4,5-dihydro-1,3-oxazol-4-yl}methanol;
methyl 3-(3-pyrrolidin-1-ylpropoxy)benzoate;
methyl 4-[3-(2-methylpiperidin-1-yl)propoxy]benzoate;
methyl 4-[3-(2,6-dimethylpiperidin-1-yl)propoxy]benzoate;
methyl 4-[3-(2-methylpyrrolidin-1-yl)propoxy]benzoate;
3-(3-piperidin-1-ylpropoxy)benzoic acid;
3-(3-pyrrolidin-1-ylpropoxy)benzoic acid;
4-[3-(2-methylpiperidin-1-yl)propoxy]benzoic acid;
4-[3-(2,6-dimethylpiperidin-1-yl)propoxy]benzoic acid;
4-[3-(2-methylpyrrolidin-1-yl)propoxy]benzoic acid;
2-[4-(benzyloxy)phenyl]-3-oxa-1-azaspiro[4.5]dec-1-ene;
4-(3-oxa-1-azaspiro[4.5]dec-1-en-2-yl)phenol;
2-[4-(3-chloropropoxy)phenyl]-4,4-dimethyl-4,5-dihydro-1,3-oxazole;
2-[4-(3-chloropropoxy)phenyl]-3-oxa-1-azaspiro[4.5]dec-1-ene;
2-[3-(3-chloropropoxy)phenyl]-4,4-dimethyl-4,5-dihydro-1,3-oxazole;
2-(6-chloropyridin-3-yl)-3-oxa-1-azaspiro[4.5]dec-1-ene;
N-[(1-hydroxycyclohexyl)methyl]-4-(3-piperidin-1-ylpropoxy)benzamide;
[2-(6-chloropyridin-3-yl)-4-methyl-4,5-dihydro-1,3-oxazol-4-yl]methanol;
(4-methyl-2-{6-[3-(2-methylpyrrolidin-1-yl)propoxy]pyridin-3-yl}-4,5-dihydro-1,3-oxazol-4-yl)methanol;
4-methyl-2-{6-[3-(2-methylpyrrolidin-1-yl)propoxy]pyridin-3-yl}-4,5-dihydro-1,3-oxazole-4-carbaldehyde;
4-amino-1-benzylpiperidine-4-carboxylic acid hydrochloride;
methyl 3-amino-1-benzylpyrrolidine-3-carboxylate;
methyl 1-benzyl-4-({4-[3-(2-methylpyrrolidin-1-yl)propoxy]benzoyl}amino)piperidine-4-carboxylate;
methyl 1-benzyl-3-({4-[3-(2-methylpyrrolidin-1-yl)propoxy]benzoyl}amino)pyrrolidine-3-carboxylate;
N-[1-benzyl-4-(hydroxymethyl)piperidin-4-yl]-4-[3-(2-methylpyrrolidin-1-yl)propoxy]benzamide;
N-[1-benzyl-3-(hydroxymethyl)pyrrolidin-3-yl]-4-[3-(2-methylpyrrolidin-1-yl)propoxy]benzamide;
2-[4-(3-chloro-2-methylpropoxy)phenyl]-3-oxa-1-azaspiro[4.5]dec-1-ene; and
2-amino-4-pyrrolidin-1-ylbutan-1-ol.

Particularly, the present invention relates to the use of said synthetic intermediates for the preparation of compounds of formula (I).

It has now been found that compounds of formula (I) according to the present invention and their pharmaceutically acceptable salts are useful in a variety of medical disorders.

For example, the compounds according to the invention are useful for the treatment and prevention of diseases or pathological conditions of the central nervous system including mild-cognitive impairment, Alzheimer's disease, learning and memory disorders, cognitive disorders, attention deficit disorder, attention-deficit hyperactivity disorder, Parkinson's disease, schizophrenia, dementia, depression, epilepsy, seizures, convulsions, sleep/wake disorders, narcolepsy, and/or obesity.

Furthermore, compounds according to the invention alone or in combination with an antiepileptic drug (AED) may be useful in the treatment of epilepsy, seizure or convulsions. It is known from literature that the combination of $H_3$-receptor ligands with an AED may produce additive synergistic effects on efficacy with reduced side-effects such as decreased vigilance, sedation or cognitive problems.

Furthermore, compounds of general formula (I) alone or in combination with a histamine $H_1$-receptor antagonist may also be used for the treatment of upper airway allergic disorders.

In a particular embodiment of the present invention, compounds of general formula (I), alone or in combination with muscarinic receptor ligands and particularly with a muscarinic $M_2$-receptor antagonist, may be useful for the treatment of cognitive disorders, Alzheimer's disease, and attention-deficit hyperactivity disorder.

Particularly, compounds of general formula (I) displaying NO-donor properties, alone or in combination with a nitric oxide (NO) releasing agent may be useful in the treatment of cognitive dysfunctions.

Compounds of general formula (I) may also be used in the treatment of sleep/wake and arousal/vigilance disorders such as hypersomnia, and narcolepsy.

Usually, compounds of general formula (I) may be used in the treatment of all types of cognitive-related disorders.

Preferably, compounds of general formula (I) may be used for the treatment of cognitive dysfunctions in diseases such as mild cognitive impairment, dementia, Alzheimer's disease, Parkinson's disease, Down's syndrome as well as for the treatment of attention-deficit hyperactivity disorder.

In another preferred embodiment, compounds of general formula (I) may also be used for the treatment of psychotic disorders, such as schizophrenia; or for the treatment of eating disorders, such as obesity; or for the treatment of inflammation and pain; or for the treatment of anxiety, stress and depression; or for the treatment of cardiovascular disorders, for example, myocardial infarction.

In a further aspect, compounds of formula (I) according to the present invention may be used as a medicament.

In a particular embodiment, the present invention concerns the use of a compound of formula (I) or a pharmaceutically acceptable salt thereof or of a pharmaceutical composition comprising an effective amount of said compound for the manufacture of a medicament for the treatment and prevention of mild-cognitive impairment, Alzheimer's disease, learning and memory disorders, attention-deficit hyperactivity disorder, Parkinson's disease, schizophrenia, dementia, depression, epilepsy, seizures, convulsions, sleep/wake disorders, cognitive dysfunctions, narcolepsy, hypersomnia, obesity, upper airway allergic disorders, Down's syndrome, anxiety, stress, cardiovascular disorders, inflammation and pain.

Preferably, the present invention concerns the use of a compound of formula (I) or a pharmaceutically acceptable salt thereof or a pharmaceutical composition comprising an effective amount of said compound for the manufacture of a medicament for the treatment of cognitive dysfunctions in diseases such as mild cognitive impairment, dementia, Alzheimer's disease, Parkinson's disease, Down's syndrome as well as for the treatment of attention-deficit hyperactivity disorder.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 3 to 3000 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The expression "cognitive disorders" as used herein refers to disturbances of cognition, which encompasses perception, learning and reasoning or in other terms the physiological (mental/neuronal) process of selectively acquiring, storing, and recalling information.

The expression "attention-deficit hyperactivity disorder" (ADHD) as used herein refers to a problem with inattentiveness, over-activity, impulsivity, or a combination of these. For these problems to be diagnosed as ADHD, they must be out of the normal range for the child's age and development. The term "attention-deficit disorder" (ADD) is also commonly used for the same disorder.

The expression "Alzheimer's disease" (AD) as used herein refers to a progressive, neurodegenerative disease characterized in the brain by abnormal clumps (amyloid plaques) and tangled bundles of fibers (neurofibrillary tangles) composed of misplaced proteins. Age is the most important risk factor for AD; the number of people with the disease doubles every 5 years beyond age 65. Three genes have been discovered that cause early onset (familial) AD. Other genetic mutations that cause excessive accumulation of amyloid protein are associated with age-related (sporadic) AD. Symptoms of AD include memory loss, language deterioration, impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging.

The expression "Parkinson's disease" (PD) as used herein refers to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. As the disease progresses, the shaking, or tremor, which affects the majority of PD patients may begin to interfere with daily activities. Other symptoms may include depression and other emotional changes; difficulty in swallowing, chewing, and speaking; urinary problems or constipation; skin problems; and sleep disruptions.

The expression "Down's syndrome" as used herein refers to a chromosome abnormality, usually due to an extra copy of the 21st chromosome. This syndrome, usually but not always, results in mental retardation and other conditions. The term "mental retardation" refers to a below-average general intellectual function with associated deficits in adaptive behavior that occurs before age 18.

The term "mild-cognitive impairment" as used herein refers to a transitional stage of cognitive impairment between normal aging and early Alzheimer's disease. It refers particularly to a clinical state of individuals who are memory impaired but are otherwise functioning well and do not meet clinical criteria for dementia.

The term "obesity" as used herein refers to a body mass index (BMI) which is greater than 30 kg/m$^2$.

The term "dementia" as used herein refers to a group of symptoms involving progressive impairment of brain function. American Geriatrics Society refers to dementia as a condition of declining mental abilities, especially memory. The person will have problems doing things he or she used to be able to do, like keep the check book, drive a car safely, or plan a meal. He or she will often have problems finding the right words and may become confused when given too many things to do at once. The person with dementia may also change in personality, becoming aggressive, paranoid, or depressed.

The term "schizophrenia" as used herein refers to a group of psychotic disorders characterized by disturbances in thought, perception, attention, affect, behavior, and communication that last longer than 6 months. It is a disease that makes it difficult for a person to tell the difference between real and unreal experiences, to think logically, to have normal emotional responses to others, and to behave normally in social situations.

The term "anxiety" as used herein refers to a feeling of apprehension or fear. Anxiety is often accompanied by physical symptoms, including twitching or trembling, muscle tension, headaches, sweating, dry mouth, difficulty swallowing and/or abdominal pain.

The term "narcolepsy" as used herein refers to a sleep disorder associated with uncontrollable sleepiness and frequent daytime sleeping.

The term "depression" as used herein refers to a disturbance of mood and is characterized by a loss of interest or pleasure in normal everyday activities. People who are depressed may feel "down in the dumps" for weeks, months, or even years at a time. Some of the following symptoms may be symptoms of depression: persistent sad, anxious, or "empty" mood; feelings of hopelessness, pessimism; feelings of guilt, worthlessness, helplessness; loss of interest or pleasure in hobbies and activities that were once enjoyed, including sex; decreased energy, fatigue, being "slowed down"; difficulty concentrating, remembering, making decisions; insomnia, early-morning awakening, or oversleeping; appetite and/or weight loss or overeating and weight gain; thoughts of death or suicide; suicide attempts; restlessness, irritability; persistent physical symptoms that do not respond to treatment, such as headaches, digestive disorders, and chronic pain.

The term "epilepsy" as used herein refers a brain disorder in which clusters of nerve cells, or neurons, in the brain sometimes signal abnormally. In epilepsy, the normal pattern of neuronal activity becomes disturbed, causing strange sensations, emotions, and behavior or sometimes convulsions, muscle spasms, and loss of consciousness. Epilepsy is a disorder with many possible causes. Anything that disturbs the normal pattern of neuron activity—from illness to brain damage to abnormal brain development—can lead to seizures. Epilepsy may develop because of an abnormality in brain wiring, an imbalance of nerve signaling chemicals called neurotransmitters, or some combination of these factors. Having a seizure does not necessarily mean that a person has epilepsy. Only when a person has had two or more seizures is he or she considered to have epilepsy.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The pain of a migraine headache is often described as an intense pulsing or throbbing pain in one area of the head. It is often accompanied by extreme sensitivity to light and sound, nausea, and vomiting. Some individuals can predict the onset of a migraine because it is preceded by an "aura," visual disturbances that appear as flashing lights, zig-zag lines or a temporary loss of vision. People with migraine tend to have recurring attacks triggered by a lack of food or sleep, exposure to light, or hormonal irregularities (only in women). Anxiety, stress, or relaxation after stress can also be triggers. For many years, scientists believed that migraines were linked to the dilation and constriction of blood vessels in the head. Investigators now believe that migraine is caused by inherited abnormalities in genes that control the activities of certain cell populations in the brain. The International Headache Society (IHS, 1988) classifies migraine with aura (classical migraine) and migraine without aura (common migraine) as the major types of migraine.

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

For the preferred oral compositions, the daily dosage is in the range 3 to 3000 milligrams (mg) of compounds of formula (I).

In compositions for parenteral administration, the quantity of compound of formula (I) present is at least 0.5% by weight and can be up to 33% by weight with respect to the total weight of the composition. For the preferred parenteral compositions, the dosage unit is in the range 3 mg to 3000 mg of compounds of formula (I).

The daily dose can fall within a wide range of dosage units of compound of formula (I) and is generally in the range 3 to 3000 mg. However, it should be understood that the specific doses can be adapted to particular cases depending on the individual requirements, at the physician's discretion.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in dimethylsulfoxide-$d_6$ (DMSO-$d_6$) or chloroform-d (CDCl$_3$) solution at a probe temperature of 313 K or 300 K and at a concentration of 20 mg/ml. The instrument is locked respectively on the deuterium signal of dimethylsulfoxide-$d_6$ (DMSO-$d_6$) or chloroform-d (CDCl$_3$).

Chemical shifts are given in ppm downfield from TMS taken as internal standard.

HPLC analyses are performed using one of the following systems:

an Agilent 1100 series HPLC system mounted with an INERTSIL ODS 3 C18, DP 5 μm, 250×4.6 mm column. The gradient runs from 100% solvent A (acetonitrile, water, phosphoric acid (5/95/0.001, v/v/v)) to 100% solvent B (acetonitrile, water, phosphoric acid (95/5/0.001, v/v/v)) in 6 min with a hold at 100% B of 4 min. The flow rate is set at 2.5 ml/min. The chromatography is carried out at 35° C.

a HP 1090 series HPLC system mounted with a HPLC Waters Symmetry C18, 250×4.6 mm column. The gradient runs from 100% solvent A (methanol, water, phosphoric acid (15/85/0.001M, v/v/M)) to 100% solvent B (methanol, water, phosphoric acid (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:

HPLC Conditions

Analyses are performed using a WATERS Alliance HPLC system mounted with an INERTSIL ODS 3, DP 5 μm, 250×4.6 mm column.

The gradient runs from 100% solvent A (acetonitrile, water, trifluoroacetic acid (10/90/0.1, v/v/v)) to 100% solvent B (acetonitrile, water, trifluoroacetic acid (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μg/ml. API spectra (+ or −) are performed using a FINNIGAN LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN TSQ 700 tandem quadrupole mass spectrometer. The source temperature is set at 150° C.

Mass spectrometric measurements on a TSQ 700 tandem quadrupole mass spectrometer (Finnigan MAT) in GC/MS mode are performed with a gas chromatograph model 3400 (Varian) fitted with a split/splitless injector and a DB-5MS fused-silica column (15 m×0.25 mm I.D., 1 μm) from J&W Scientific. Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

Specific rotation is recorded on a Perkin-Elmer 341 polarimeter. The angle of rotation is recorded at 25° C. on 1% solutions in methanol, at 589 nm. For some molecules, the solvent is dichloromethane or dimethylsulfoxide, due to solubility problems.

Melting points are determined on a Büchi 535 or 545 Tottoli-type fusionometre, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at 1350 ml/min. Solvent mixtures as described in individual procedures.

Experiments requiring microwave irradiation were performed either on a CEM Discover apparatus (CEM corporation) or on a Biotage Initiator (Biotage AB) microwave oven using the flasks and stirrers sold by these companies.

EXAMPLES

Example 1

Synthesis of 1-{3-[4-(4,4-dimethyl-4,5-dihydro-oxazol-2-yl)-phenoxy]-propyl}-piperidine 1

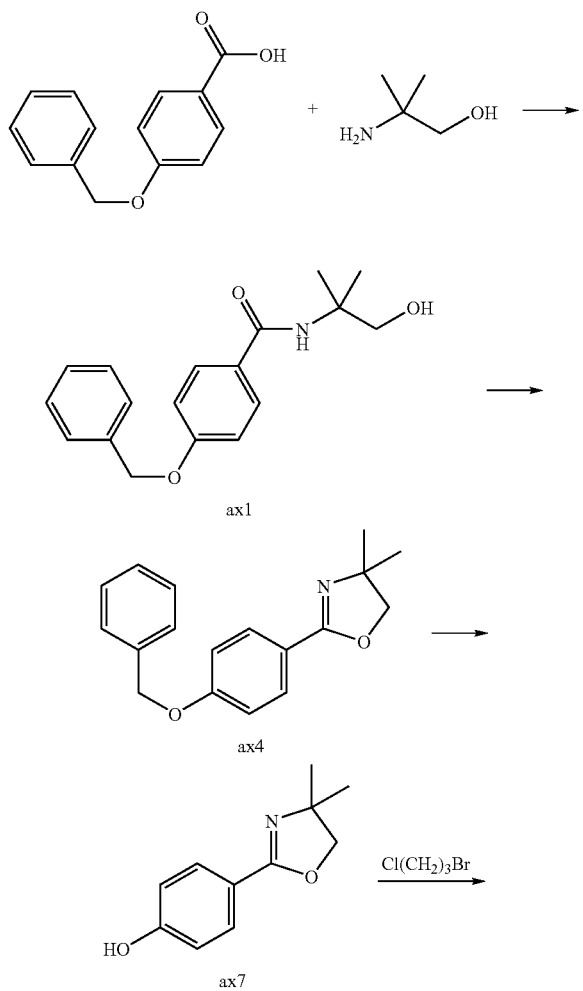

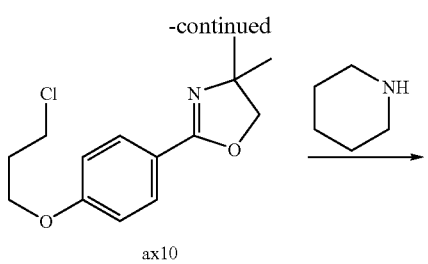

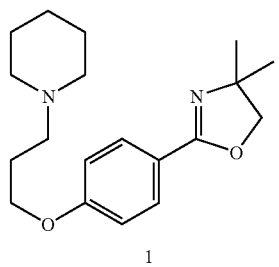

1.1 Synthesis of 4-(benzyloxy)-N-(2-hydroxy-1,1-dimethylethyl)benzamide ax1

Oxalyl chloride (6.6 ml, 76 mmol, 1.2 eq) is added into a cold (ice bath) solution of 4-benzyloxy-benzoic acid (14.38 g, 63 mmol, 1 eq) and triethylamine (43.8 ml, 315 mmol, 5 eq) in dichloromethane (400 ml). The dark red mixture is warmed to room temperature and stirred for 2 h and then cooled to 0° C. A solution of 2-amino-2-methyl-propan-1-ol (5.6 g, 63 mmol, 1 eq) in dichloromethane (20 ml) is added and the mixture is stirred overnight at room temperature. The solvent is then removed under vacuum and the residue is dissolved in dichloromethane. This solution is washed once with water and the aqueous layer is extracted with dichloromethane. The organic layers are washed with a solution of 0.1 M sodium hydroxide and dried over magnesium sulfate. The solvent is removed under vacuum, to afford 15 g of 4-(benzyloxy)-N-(2-hydroxy-1,1-dimethylethyl)benzamide ax1 as a brown solid.

Yield: 80%.

LC-MS (MH$^+$): 300.

The following compounds may be synthesized according to the same method:

| ax2 | 4-[(benzyloxy)methyl]-N-[1-(hydroxymethyl)-cyclohexyl]benzamide | $^1$H NMR: $\delta_H$(CDCl$_3$, 300 MHz) 7.7-7.67 (d, 2H), 7.42-7.38 (m, 5H), 7.02-6.99 (d, 2H), 6.02 (s, 1H, NH), 5.13 (s, 2H), 3.75 (s, 2H, —CH$_2$OH), 1.65-1.26 (m, 10H, —(CH$_2$)$_5$—) |
| ax3 | 3-(benzyloxy)-N-(2-hydroxy-1,1-dimethylethyl)benzamide | LC-MS (MH$^+$): 300 |

1.2 Synthesis of 2-[4-(benzyloxy)phenyl]-4,4-dimethyl-4,5-dihydro-1,3-oxazole ax4

Thionyl chloride (11 ml, 150 mmol, 3 eq) is added to a solution of 4-(benzyloxy)-N-(2-hydroxy-1,1-dimethylethyl)benzamide ax1 (14.98 g, 50 mmol, 1 eq) in chloroform (400 ml) and the mixture is heated at reflux for 2 h. The solvent is then removed under vacuum, and the residue is dissolved into dichloromethane. The organic layer is washed with a saturated solution of aqueous sodium bicarbonate, dried over magnesium sulfate, and concentrated under vacuum to give 2-[4-(benzyloxy)phenyl]-4,4-dimethyl-4,5-dihydro-1,3-oxazole ax4 (4.3 g).

Yield: 99%.

LC-MS (MH$^+$): 282.

The following compounds may be synthesized according to the same method:

| ax5 | 2-[4-(benzyloxy)-phenyl]-3-oxa-1-azaspiro[4.5]-dec-1-ene | $^1$H NMR: $\delta_H$(CDCl$_3$, 300 MHz) 7.92-7.87 (d, 2H), 7.42-7.35 (m, 5H), 7.00-6.96 (d, 2H), 5.11 (s, 2H), 4.14 (s, 2H, —CH$_2$—O), 1.78-1.65 (m, 10H, —(CH$_2$)$_5$—) |
| ax6 | 2-[3-(benzyloxy)-phenyl]-4,4-dimethyl-4,5-dihydro-1,3-oxazole | LC-MS (MH$^+$): 282 |

1.3 Synthesis of 4-(4,4-dimethyl-4,5-dihydro-1,3-oxazol-2-yl)phenol ax7

To a solution of 2-(4-benzyloxy-phenyl)-4,4-dimethyl-4,5-dihydro-oxazole ax4 (4.0 g, 140 mmol, 1 eq) in ethanol (200 ml) is added 1.5 g of 10% Pd/C (1.42 mmol, 0.1 eq). The mixture is stirred for 48 h at room temperature, under 40 psi of a hydrogen atmosphere. The mixture is then filtered on celite and the solvent removed under vacuum. The residual solid is triturated in hexane to give 2.6 g of 4-(4,4-dimethyl-4,5-dihydro-1,3-oxazol-2-yl)phenol ax7.

Yield: 95%.

LC-MS (MH$^+$): 192.

The following compounds may be synthesized according to the same method:

| ax8 | 4-(3-oxa-1-azaspiro[4.5]dec-1-en-2-yl)phenol | LC-MS (MH$^+$): 232 |
| ax9 | 3-(4,4-dimethyl-4,5-dihydro-1,3-oxazol-2-yl)phenol | GC-MS (M$^+$•): 191 |

1.4 Synthesis of 2-[4-(3-chloropropoxy)phenyl]-4,4-dimethyl-4,5-dihydro-1,3-oxazole ax10

A mixture of 4-(4,4-dimethyl-4,5-dihydro-1,3-oxazol-2-yl)phenol ax7 (5 g, 26 mmol, 1 eq), potassium carbonate (7.19 g, 52 mmol, 2 eq), and 1-bromo-3-chloropropane (2.8 ml, 29 mmol, 1.1 eq) in acetone (120 ml) is stirred at reflux for 36 h. The mixture is then concentrated; the residue is dissolved in dichloromethane, and washed with a saturated solution of aqueous ammonium chloride. The organic layer is dried over magnesium sulfate and concentrated under vacuum to obtain 2-[4-(3-chloropropoxy)phenyl]-4,4-dimethyl-4,5-dihydro-1,3-oxazole ax10 as a white solid (6.75 g).

Yield: 97%.

LC-MS (MH$^+$): 268/270.

The following compounds may be synthesized according to the same method:

| | | |
|---|---|---|
| ax11 | 2-[4-(3-chloropropoxy)phenyl]-3-oxa-1-azaspiro[4.5]dec-1-ene | LC-MS (MH$^+$): 308/310 |
| ax12 | 2-[3-(3-chloropropoxy)phenyl]-4,4-dimethyl-4,5-dihydro-1,3-oxazole | GC-MS (M$^+$•): 267/269 |

1.5 Synthesis of 1-{3-[4-(4,4-dimethyl-4,5-dihydro-1,3-oxazol-2-yl)phenoxy]propyl}piperidine 1

A mixture of 2-[4-(3-chloropropoxy)phenyl]-4,4-dimethyl-4,5-dihydro-1,3-oxazole ax10 (0.5 g, 1.87 mmol, 1 eq) and piperidine (0.37 ml, 3.73 mmol, 2 eq) is stirred in a sealed tube at 100° C. overnight. The mixture is then concentrated under vacuum to give 0.8 g of an orange solid. This solid is purified by chromatography on silica gel (eluent: dichloromethane/ethanol 95:5) to obtain 0.49 g of 1-{3-[4-(4,4-dimethyl-4,5-dihydro-1,3-oxazol-2-yl)phenoxy]propyl}piperidine 1 as an orange oil.

Yield: 83%.

LC-MS (MH$^+$): 317.

Example 2

Synthesis of 1-{3-[3-bromo-4-(4,4-dimethyl-4,5-dihydro-1,3-oxazol-2-yl)phenoxy]propyl}piperidine 17

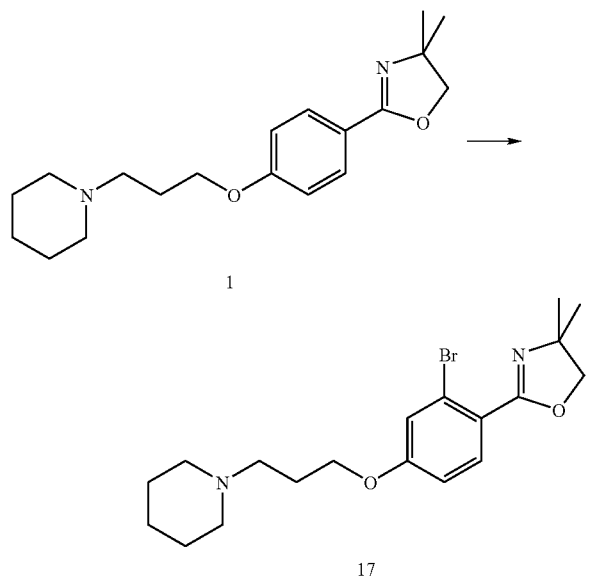

A 2.1 M solution of n-butyllithium in hexane (580 μl, 2 eq, 1.28 mmol) is added dropwise to a solution of 1-{3-[4-(4,4-dimethyl-4,5-dihydro-1,3-oxazol-2-yl)phenoxy]propyl}piperidine 1 (200 mg, 0.64 mmol, 1 eq) in cold (0° C.) tetrahydrofuran (10 ml), and the resulting solution is stirred 4 hours at 0° C. Bromine (64 μL, 2 eq, 1.28 mmol) is then added and the mixture is left to stir at 22° C. overnight. The solution is then poured into 5 ml of 0.1 N aqueous hydrogen chloride and extracted with ether. The aqueous layer is then made basic (pH 10) with 5 N sodium hydroxide and extracted with dichloromethane. The chlorinated solution is then dried over magnesium sulfate, concentrated under reduced pressure. 1-{3-[3-bromo-4-(4,4-dimethyl-4,5-dihydro-1,3-oxazol-2-yl)phenoxy]propyl}piperidine 17 is separated from the remaining starting material by careful chromatography over silicagel (dichloromethane/methanol, gradient).

Yield: 29% (37 mg).

LC-MS (MH$^+$): 395/397.

Example 3

Synthesis of 4,4-dimethyl-2-(4-{3-[(2R)-2-methylpyrrolidin-1-yl]propoxy}phenyl)-4,5-dihydro-1,3-oxazole 15

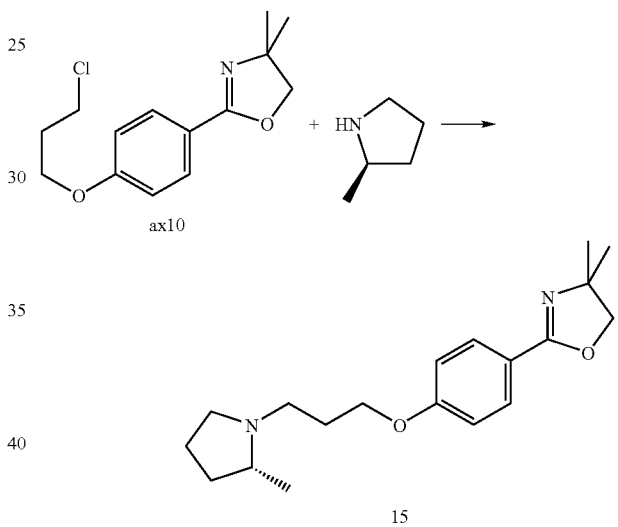

A mixture of 2-[4-(3-chloropropoxy)phenyl]-4,4-dimethyl-4,5-dihydro-1,3-oxazole ax10 (0.25 g, 0.9 mmol, 1 eq), 0.15 g of (2R)-2-methylpyrrolidine hydrochloride (1.2 mmol, 1.4 eq) and triethylamine (0.3 ml, 2.2 mmol, 2.4 eq) is stirred under microwave irradiation (120° C., 3.75 h). The mixture is then filtered. Triethylamine (0.2 ml, 1.44 mmol, 1.6 eq) is added to the organic layer, and the mixture is again stirred under microwave irradiation, at 120° C. for another 1.5 h. The solvent is then removed under vacuum and the residue diluted with ethyl acetate. The organic layer is washed with water, with a saturated solution of sodium chloride, dried over magnesium sulfate and concentrated under vacuum. The residue is purified over silicagel (eluent: dichloromethane/ethanol/ammonia, gradient from 98:2:0.2 to 96:4:0.4) to give 4,4-dimethyl-2-(4-{3-[(2R)-2-methylpyrrolidin-1-yl]propoxy}phenyl)-4,5-dihydro-1,3-oxazole 15 (60 mg) as a beige powder.

Yield: 21%.

LC-MS (MH$^+$): 317.

Alpha$_D$ (C=1%, MeOH): −51.14°.

Example 4

Synthesis of 1{3-[4-(5-methyl-4-phenyl-4,5-dihydro-oxazol-2-yl)-phenoxy]-propyl}-piperidine 6

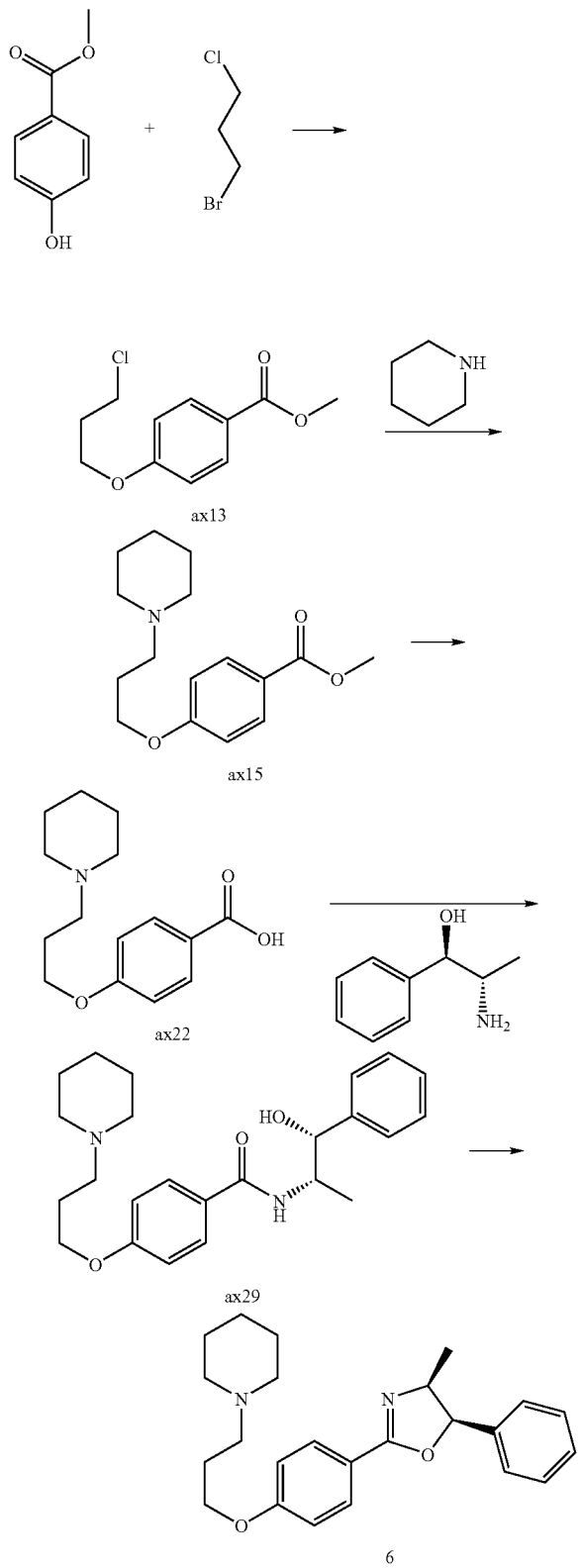

4.1 Synthesis of methyl 4-(3-chloropropoxy)benzoate ax13

1-bromo-3-chloropropane (6.8 ml, 78.3 mmol, 1.1 eq) is added to a mixture of methyl 4-hydroxybenzoate (10 g, 65.7 mmol, 1 eq), potassium bicarbonate (18 g, 130 mmol, 2 eq) in acetone (260 ml). The mixture is then stirred at reflux overnight, filtered and concentrated under vacuum. The residue is triturated in hexane and ether and then filtered. The resulting solution is concentrated to give 4-(3-chloropropoxy)benzoate ax13 as a yellow oil (14.3 g).
Yield: 95%.
LC-MS (MH$^+$): 229/231.
The following compound may be synthesized according to the same method:

| | | |
|---|---|---|
| ax14 | methyl 3-(3-chloropropoxy)benzoate | LC-MS (MH$^+$): 229/231 |

4.2 Synthesis of methyl 4-(3-piperidin-1-ylpropoxy)benzoate ax15

A mixture of 4-(3-chloropropoxy)benzoate ax13 (2.01 g, 8.79 mmol, 1 eq), potassium carbonate (2.43 g, 17.6 mmol, 2 eq), sodium iodide (catalytic amount) and piperidine (1 ml, 9.67 mmol, 1.1 eq) in acetonitrile (100 ml) is stirred at reflux for 56 h. The solvent is removed under vacuum and the solid is triturated in hexane and filtered. The resulting solution is concentrated to give methyl 4-(3-piperidin-1-ylpropoxy)benzoate ax15 as a yellow oil (2.2 g).
Yield: 92%.
LC-MS (MH$^+$): 278.
The following compounds may be synthesized according to the same method:

| | | |
|---|---|---|
| ax16 | methyl 3-(3-piperidin-1-ylpropoxy)benzoate | LC-MS (MH$^+$): 278 |
| ax17 | methyl 4-(3-pyrrolidin-1-ylpropoxy)benzoate | LC-MS (MH$^+$): 264 |
| ax18 | methyl 3-(3-pyrrolidin-1-ylpropoxy)benzoate | LC-MS (MH$^+$): 264 |
| ax19 | methyl 4-[3-(2-methylpiperidin-1-yl)propoxy]benzoate | LC-MS (MH$^+$): 292 |
| ax20 | methyl 4-[3-(2,6-dimethylpiperidin-1-yl)propoxy]benzoate | LC-MS (MH$^+$): 307 |
| ax21 | methyl 4-[3-(2-methylpyrrolidin-1-yl)propoxy]benzoate | LC-MS (MH$^+$): 278 |

4.3 Synthesis of 4-(3-piperidin-1-ylpropoxy)benzoic acid ax22

To methyl 4-(3-piperidin-1-ylpropoxy)benzoate ax15 (4.41 g, 15.9 mmol, 1 eq) in ethanol (160 ml) is added a 5 N aqueous solution of sodium hydroxide (9.54 ml, 47.7 mmol, 3 eq) and the mixture is stirred at 60° C. for 4 h and at 28° C. overnight. The mixture is concentrated under vacuum to give a white solid, which is then dissolved in a 1:1 mixture of ethanol/water (100 ml). A solution of 5 N aqueous hydrochloric acid is then added until the pH of the mixture reaches 2-3. The ethanol is then evaporated under vacuum and the mixture filtered to give a white solid. This solid is washed with water and dried under vacuum at 40° C.

Yield: 99%.

LC-MS (MH$^+$): 264.

The following compounds may be synthesized according to the same method:

| ax23 | 3-(3-piperidin-1-ylpropoxy)benzoic acid | LC-MS (MH$^+$): 264 |
|---|---|---|
| ax24 | 4-(3-pyrrolidin-1-ylpropoxy)benzoic acid | LC-MS (MH$^+$): 250 |
| ax25 | 3-(3-pyrrolidin-1-ylpropoxy)benzoic acid | LC-MS (MH$^+$): 250 |
| ax26 | 4-[3-(2-methylpiperidin-1-yl)propoxy]benzoic acid | LC-MS (MH$^+$): 278 |
| ax27 | 4-[3-(2,6-dimethylpiperidin-1-yl)propoxy]benzoic acid | LC-MS (MH$^+$): 292 |
| ax28 | 4-[3-(2-methylpyrrolidin-1-yl)propoxy]benzoic acid | LC-MS (MH$^+$): 264 |

4.4 Synthesis of N-(2-hydroxy-1-ethyl-2-phenylethyl)-4-(3-piperidin-1-ylpropoxy)benzamide ax29

4.4.1 Method A.

To 4-(3-piperidin-1-ylpropoxy)benzoic acid ax22 (0.263 g, 1 mmol, 1 eq) in chloroform is added thionyl chloride (0.25 ml, 3 mmol, 3 eq) and dimethylformamide (one drop). The mixture is then stirred for 2 h at reflux. Another portion of thionyl chloride (0.25 ml, 3 mmol, 3 eq) is added and the mixture is stirred at reflux for 30 min. The mixture is then diluted with dichloromethane and cooled to 0° C. (ice bath). Triethylamine is slowly added, until the pH reaches 8. (1R, 2S)-2-Amino-1-phenylpropan-1-ol (0.15 g, 1 mmol, 1 eq) in chloroform is added slowly, and the mixture is stirred at 25° C. overnight. The mixture is then diluted with dichloromethane (30 ml) and washed with water (3×50 ml), with a saturated solution of sodium chloride (2×50 ml) and dried over magnesium sulfate to give N-(1S,2R-2-hydroxy-1-methyl-2-phenylethyl)-4-(3-piperidin-1-ylpropoxy)benzamide ax29 as a yellow oil (0.29 g).

Yield: 73%.

LC-MS (MH$^+$): 397.

The following compounds may be synthesized according to the same method:

| ax30 | N-[1-(hydroxymethyl)cyclohexyl]-4-(3-piperidin-1-ylpropoxy)benzamide | LC-MS (MH$^+$): 375 |
|---|---|---|

4.4.2 Method B.

To a solution of the acid (1 eq) and the amine (1 eq) in a suitable solvent such as dichloromethane (12 ml) is added triethylamine (2 eq), 1-hydroxybenzotriazole (0.2 eq), and 1-(3-dimethylaminopropyl)-3-ethylcarbodiimide hydrochloride (1.1 eq). The mixture is then stirred at room temperature overnight. It is then washed with water, then with a saturated solution of sodium chloride, dried over magnesium sulfate and concentrated under vacuum.

The following compounds may be synthesized according to Method B:

| ax31 | N-[1-(hydroxymethyl)cyclohexyl]-3-(3-piperidin-1-ylpropoxy)benzamide | LC-MS (MH$^+$): 375 |
|---|---|---|
| ax32 | N-[1-(hydroxymethyl)cyclohexyl]-4-[3-(2-methylpiperidin-1-yl)propoxy]benzamide | LC-MS (MH$^+$): 389 |
| ax33 | N-[1-(hydroxymethyl)cyclohexyl]-4-(3-pyrrolidin-1-ylpropoxy)benzamide | LC-MS (MH$^+$): 361 |
| ax34 | N-[1-(hydroxymethyl)cyclohexyl]-3-(3-pyrrolidin-1-ylpropoxy)benzamide | LC-MS (MH$^+$): 361 |
| ax36 | N-[1-(hydroxymethyl)-3-pyrrolidin-1-ylpropyl]-4-(3-piperidin-1-ylpropoxy)benzamide | LC-MS (MH$^+$): 312 |
| ax37 | methyl N-[4-(3-piperidin-1-ylpropoxy)benzoyl]serinate | LC-MS (MH$^+$): 365 |
| ax38 | N-[1-(hydroxymethyl)cyclopropyl]-4-(3-piperidin-1-ylpropoxy)benzamide | LC-MS (MH$^+$): 264 |
| ax39 | N-(1-benzyl-2-hydroxyethyl)-4-(3-piperidin-1-ylpropoxy)benzamide | LC-MS (MH$^+$): 397 |
| ax40 | N-(2-hydroxy-1,1-dimethylethyl)-4-(3-piperidin-1-ylpropoxy)benzamide | LC-MS (MH$^+$): 335 |
| ax41 | N-[1-(hydroxymethyl)-2,2-dimethylpropyl]-4-[3-(2-methylpyrrolidin-1-yl)propoxy]benzamide | LC-MS (MH$^+$): 364 |
| ax42 | N-[(1R,2R)-2-hydroxycyclohexyl]-4-[3-(2-methylpyrrolidin-1-yl)propoxy]benzamide | LC-MS (MH$^+$): 403 |
| ax43 | N-(2-hydroxy-1-phenylethyl)-4-[3-(2-methylpyrrolidin-1-yl)propoxy]benzamide | LC-MS (MH$^+$): 383 |
| ax44 | N-[2-cyclohexyl-1-(hydroxymethyl)ethyl]-4-[3-(2-methylpyrrolidin-1-yl)propoxy]benzamide | LC-MS (MH$^+$): 361 |
| ax54 | N-[(1-hydroxycyclohexyl)methyl]-4-(3-piperidin-1-ylpropoxy)benzamide | LC-MS (MH$^+$): 375 |

Preparation of N-[1-(hydroxymethyl)-3-pyrrolidin-1-ylpropyl]-4-(3-piperidin-1-ylpropoxy)benzamide ax36 from 2-amino-4-pyrrolidin-1-yl-butan-1-ol ax35

Synthesis of 2-amino-4-pyrrolidin-1-yl-butan-1-ol ax35: a solution of 1M lithium aluminium hydride (12.2 ml, 12.2 mmol) in tetrahydrofuran is added to a cold (−20° C.) suspension of 2-amino-4-pyrrolidin-1-ylbutanoic acid (0.994 g, 4.05 mmol) in tetrahydrofuran (20 ml). The mixture is left to warm to 22° C. and is then heated for one hour at 60° C. The mixture is then cooled to 0° C. and is carefully quenched by the successive addition of water, 1 N aqueous sodium hydroxide and water. After one hour stirring at 0° C., the suspension is filtered and the solid is washed with ethyl acetate. The liquid phase is concentrated in vacuo to yield 318 mg of 2-amino-4-pyrrolidin-1-ylbutan-1-ol ax35 as a yellow oil.

Yield: 65.5%

LC-MS (MH$^+$): 159.

N-[1-(hydroxymethyl)-3-pyrrolidin-1-ylpropyl]-4-(3-piperidin-1-ylpropoxy)benzamide ax36 is prepared according to method B described above.

4.5 Synthesis of 1-(3-{4-[(4S,5R)-4-methyl-5-phenyl-4,5-dihydro-1,3-oxazol-2-yl]phenoxy}propyl)piperidine 6

To a cold (ice-bath) solution of N-(2-hydroxy-1-methyl-2-phenylethyl)-4-(3-piperidin-1-ylpropoxy)benzamide ax29 (0.266 g, 0.67 mmol, 1 eq) in chloroform (10 ml), is slowly added thionyl chloride (0.2 ml, 2.68 mmol, 4 eq) and the mixture is stirred at reflux for 2 h 30. The mixture is then diluted with dichloromethane (50 ml) and washed with a saturated solution of sodium bicarbonate (2×50 ml). The organic layers are dried over magnesium sulfate and concentrated under vacuum to give 0.24 g of a brown oil. The product is purified by chromatography on silicagel (eluent: dichloromethane/ethanol/ammonia 95:4.5:0.5).

Yield: 94%.

LC-MS (MH$^+$): 379.

alpha$_D$ (C=9.79 mg/ml, MeOH): +25.54°.

Example 5

Synthesis of 1-(3-{4-[4-(piperidin-1-ylmethyl)-4,5-dihydro-1,3-oxazol-2-yl]phenoxy}propyl)piperidine 20

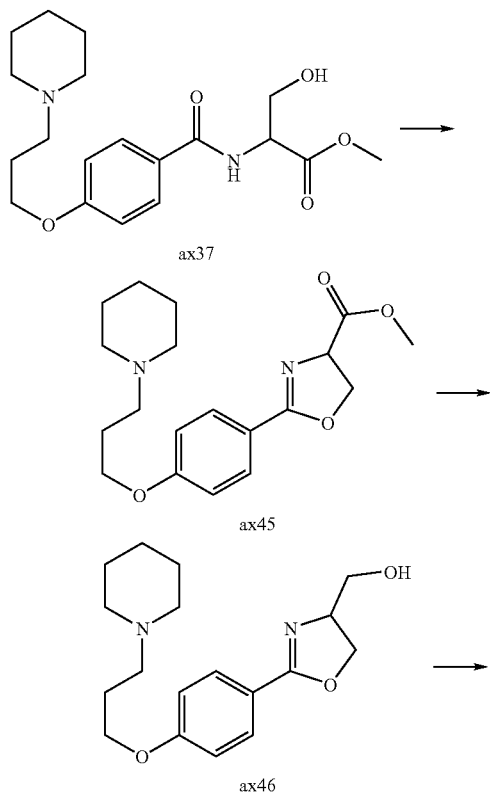

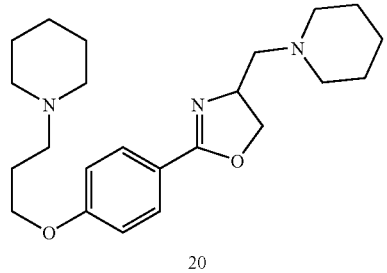

20

5.1 Synthesis of methyl 2-[4-(3-piperidin-1-ylpropoxy)phenyl]-4,5-dihydro-1,3-oxazole-4-carboxylate ax45

A mixture of methyl N-[4-(3-piperidin-1-ylpropoxy)benzoyl]serinate ax37 (0.922 g, 2.54 mmol, 1 eq) and (diethylamino)sulfur trifluoride (0.34 ml, 2.78 mmol, 1.1 eq) in dichloromethane (25 ml) is stirred under argon at room temperature for 3.5 h before addition of potassium carbonate (0.35 g, 2.53 mmol, 1 eq). The mixture is stirred for a further 1 h and washed with a saturated solution of potassium hydrogencarbonate and the aqueous layer is extracted with dichloromethane. The organic layers are then dried over magnesium sulfate and concentrated under vacuum to give methyl 2-[4-(3-piperidin-1-ylpropoxy)phenyl]-4,5-dihydro-1,3-oxazole-4-carboxylate ax45 as an orange oil (1.036 g) which is used without further purification.

LC-MS (MH$^+$): 347.

5.2 Synthesis of {2-[4-(3-piperidin-1-ylpropoxy)phenyl]-4,5-dihydro-1,3-oxazol-4-yl}methanol ax46

Sodium borohydride (0.525 g, 13.88 mmol, 5 eq) is added in small portions to a solution of methyl 2-[4-(3-piperidin-1-ylpropoxy)phenyl]-4,5-dihydro-1,3-oxazole-4-carboxylate ax45 (0.962 g, 2.78 mmol, 1 eq) in methanol (28 ml) at 0° C. (ice bath). The mixture is stirred at room temperature for 4 h, the solvent removed under vacuum and the residue dissolved in ethyl acetate. The organic layer is washed with a 0.1 M solution of aqueous sodium hydroxide and this aqueous layer is extracted with ethyl acetate. The organic layers are dried over magnesium sulfate and concentrated under vacuum to give 0.72 g of a yellow oil, which is purified on silicagel with a 9:1 mixture of dichloromethane and ethanol. {2-[4-(3-piperidin-1-ylpropoxy)phenyl]-4,5-dihydro-1,3-oxazol-4-yl}methanol ax46 is obtained as a yellow solid (0.28 g).

Yield: 32%.

LC-MS (MH$^+$): 319.

5.3 Synthesis of 1-(3-{4-[4-(piperidin-1-ylmethyl)-4,5-dihydro-1,3-oxazol-2-yl]phenoxy}propyl)piperidine 20

To a cold (−23° C.) solution of {2-[4-(3-piperidin-1-ylpropoxy)phenyl]-4,5-dihydro-1,3-oxazol-4-yl}methanol ax46 (0.27 g, 0.85 mmol, 1 eq) and triethylamine (0.413 ml, 2.98 mmol, 3.5 eq) in tetrahydrofuran (10 ml) is added methanesulfonyl chloride (0.23 ml, 2.98 mmol, 3.5 eq). The mixture is stirred for 2 h at −23° C., and then, concentrated under vacuum. The residual oil is treated with piperidine (0.08 ml, 0.8 nmol, 2 eq) and triethylamine (0.05 ml, 0.42 mmol, 1 eq) and stirred at 100° C. in a sealed tube overnight. After 24 h, piperidine (1 eq) and triethylamine (1 eq) are added and the mixture is stirred for another 48 h at 100° C. Concentration under vacuum gives 0.33 g of brown oil. The oil is purified on silicagel (eluent: dichloromethane/ethanol/ammonia 92:7.2: 0.8) to give 45 mg of 1-(3-{4-[4-(piperidin-1-ylmethyl)-4,5-dihydro-1,3-oxazol-2-yl]phenoxy}propyl)piperidine 20.

Yield: 28%.

LC-MS (MH+): 386.

Example 6

Synthesis of 2-[(6-[3-(2-methylpyrrolidin-1-yl)propoxy]pyridin-3-yl]-3-oxa-1-azaspiro[4.5]dec-1-ene 16.

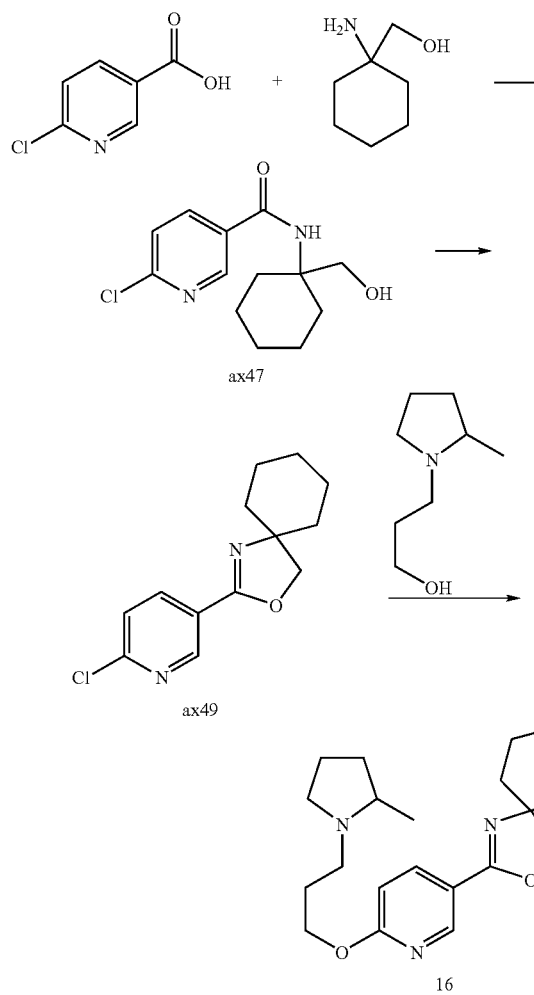

16

6.1 Synthesis of 6-chloro-N-[1-(hydroxymethyl)cyclohexyl]nicotinamide ax47

Triethylamine (2.2 ml, 16.12 mmol, 2 eq), hydroxybenzotriazole hydrate (0.217 g, 1.61 mmol, 0.2 eq), and 1-(3-dimethylaminopropyl)-3-ethylcarbodiimide hydrochloride (1.7 g, 8.87 mmol, 1.1 eq) are added to a cold (ice bath) solution of 6-chloronicotinic acid (1.27 g, 8.06 mmol, 1 eq) and (1-aminocyclohexyl)methanol (1.04 g, 8.06 mmol, 1 eq) in dichloromethane (80 ml), stirred 30 min at 0° C. and then at room temperature for 1 h. The organic layer is then washed with water, with a saturated solution of aqueous sodium hydrogenocarbonate and dried over magnesium sulfate. The solvent is finally removed to give 2.46 g of a yellow oil.

Yield: 100%.

LC-MS (MH+): 269/271.

The following compound may be synthesized according to the same method:

| ax48 | 6-chloro-N-(2-hydroxy-1,1-dimethylethyl)nicotinamide | 1H NMR: δ$_H$(CDCl$_3$, 200 MHz) 8.68 (s, 1H) 8.05 (d, 6 Hz, 1H), 7.42 (d, 6 Hz, 1H), 6.18 (s, 1H), 3.68 (s, 2H), 1.42 (s, 6H) |
|---|---|---|

6.2 Synthesis of 2-(6-chloropyridin-3-yl)-3-oxa-1-azaspiro[4.5]dec-1-ene ax49.

To a solution of 6-chloro-N-[1-(hydroxymethyl)cyclohexyl]nicotinamide ax47 (2.17 g, 8.06 mmol, 1 eq) in chloroform (80 ml) is added thionyl chloride (1.8 ml, 24.18 mmol, 3 eq). The mixture is stirred at reflux for 2 h 30 before removing the volatiles under vacuum. The residue is dissolved in acetone and treated with potassium carbonate (2 eq), at reflux. After an aqueous work-up, the organic phase is dried over magnesium sulfate and concentrated in vacuo to give 1.86 g of a yellow solid. Purification over silicagel (eluent: dichloromethane/methanol/ammonia 99:1:0.1) finally yields 0.56 g of 2-(6-chloropyridin-3-yl)-3-oxa-1-azaspiro[4.5]dec-1-ene ax49.

Yield: 55%.

LC-MS (MH+): 251/253.

The following compound may be synthesized according to the same method:

| ax50 | 2-chloro-5-(4,4-dimethyl-4,5-dihydro-1,3-oxazol-2-yl)pyridine | 1H NMR: δ$_H$(CDCl$_3$, 200 MHz) 8.88 (d, 1H), 8.13 (d, 1H), 7.37 (d, 1H)), 4.11 (s, 2H, —CH$_2$—), 1.36 (s, 6H, —C(CH$_3$)$_2$—) |
|---|---|---|

6.3 Synthesis of 2-{6-[3-(2-methylpyrrolidin-1-yl)propoxy]pyridin-3-yl}-3-oxa-1-azaspiro[4.5]dec-1-ene 16.

2-(6-chloropyridin-3-yl)-3-oxa-1-azaspiro[4.5]dec-1-ene ax49 (0.109 g, 0.76 mmol, 1 eq) and potassium tert-butanolate (0.102 g, 0.91 mmol, 1.2 eq) are added to a cold (0° C.) solution of 3-(2-methylpyrrolidin-1-yl)propan-1-ol (0.2 g, 0.8 mmol, 1.05 eq) in tetrahydrofuran (4 ml). The mixture is stirred under microwave irradiation (150 W) at 60° C. for 21 min. Ethyl acetate is then added. The organic layer is washed with a saturated solution of sodium hydrogenocarbonate, dried over magnesium sulfate and the solvent is removed under vacuum to give 0.227 g of yellow oil. The oil is purified over silica (eluent: dichloromethane/methanol/ammonia 97:2.7:0.3) to give 0.149 g of 2-{6-[3-(2-methylpyrrolidin-1-yl)propoxy]pyridin-3-yl}-3-oxa-1-azaspiro[4.5]dec-1-ene 16 as a yellow oil.
Yield: 55%.
LC-MS (MH+): 358.

Example 7

Synthesis of the maleate salt of 2-(4-{3-[2,5-dimethylpyrrolidin-1-yl]propoxy}phenyl)-4,4-dimethyl-4,5-dihydro-1,3-oxazole 18

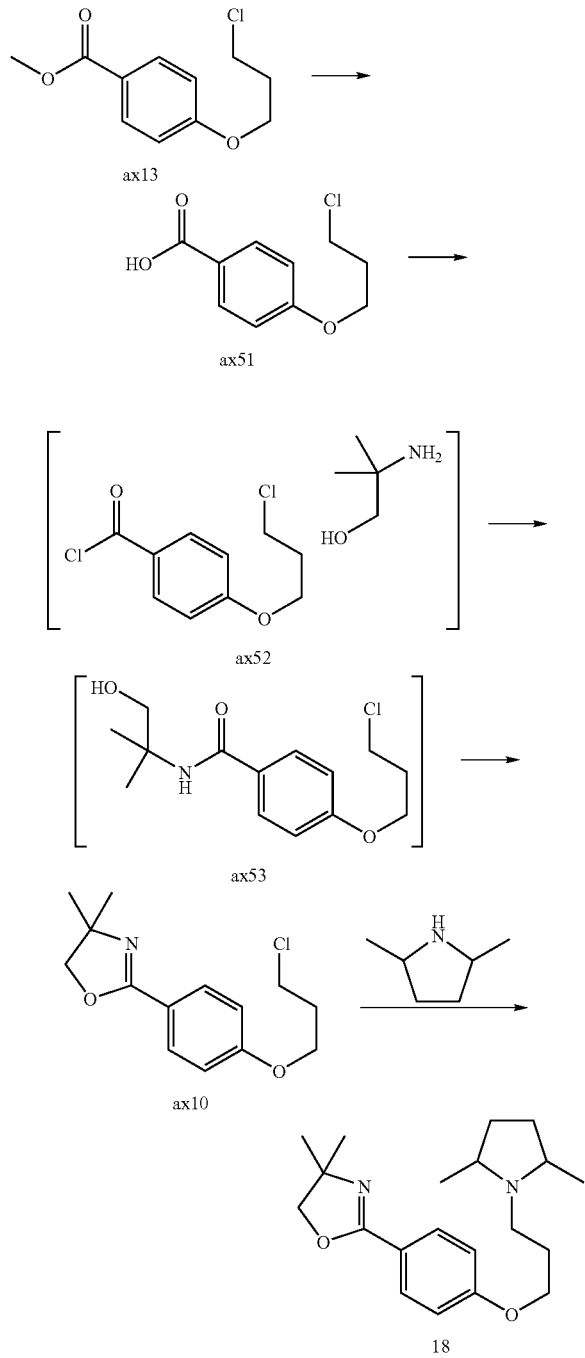

7.1 Synthesis of 4-(3-chloropropoxy)benzoic acid ax51

To a solution of methyl 4-(3-chloropropoxy)benzoate ax13 (3 g, 13 mmol, 1 eq) in ethanol (30 ml) is added 2.5 M aqueous sodium hydroxide (10 ml, 25 mmol, 2 eq). The mixture is refluxed for 1 hour, concentrated under vacuum, acidified with 2 M aqueous hydrochloric acid to pH 1 and extracted with ethyl acetate (3×50 ml). The combined organic layers are evaporated to give 2.75 g of 4-(3-chloropropoxy)benzoic acid ax51.
Yield: 98%.
$^1$H NMR: $\delta_H$ (CDCl$_3$): 7.87 (d, 2H), 7.05 (d, 2H), 4.12 (t, 2H), 3.81 (t, 2H), 2.14 (quintet, 2H).

7.2 Synthesis of 2-[4-(3-chloropropoxy)phenyl]-4,4-dimethyl-4,5-dihydro-1,3-oxazole ax10

Thionyl chloride (1.82 ml, 25 mmol, 2 eq), dimethylformamide (catalytic amount) and 4-(3-chloropropoxy)benzoic acid ax51 (2.67 g, 12.47 mmol, 1 eq) are stirred at reflux for 3 hours in chloroform (25 ml). The volatiles are then removed under vacuum, toluene is added and the mixture is concentrated again to remove residual traces of thionyl chloride. 4-(3-chloropropoxy)benzoyl chloride ax52 (2.95 g) is used for the next step without any further purification.

A solution of 2-amino-2-methylpropanol (0.914 g, 10.2 mmol, 1.1 eq) and triethylamine (2.6 ml, 18.7 mmol, 2 eq) in dry dichloromethane (75 ml) is cooled (ice bath) and a solution of 4-(3-chloropropoxy)benzoyl chloride ax52 (2.95 g, 12.4 mmol, 1 eq) in dichloromethane (15 ml) is added dropwise, over 30 min. The mixture is then stirred at room temperature overnight. The suspension is washed with 1 M aqueous hydrochloric acid (2 times), an aqueous potassium carbonate solution (2 times) and brine, dried over magnesium sulfate and evaporated in vacuum to give 4-(3-chloropropoxy)-N-(2-hydroxy-1,1-dimethylethyl)benzamide ax53 (3.4 g).

Thionyl chloride (1.55 g, 13.09 mmol, 1.1 equiv.) is added dropwise to 4-(3-chloropropoxy)-N-(2-hydroxy-1,1-dimethylethyl)benzamide ax53 (3.18 g, 11.9 mmol, 1 eq) in dry dichloromethane (100 ml), under a nitrogen atmosphere over 30 min. The solution is then stirred for 3 h. Water and potassium carbonate are finally added and the mixture is stirred until no more bubbles are formed (pH=10). The layers are separated and the dichloromethane layer is washed with brine, dried over sodium sulfate and evaporated under vacuum to give 3.18 g of 2-[4-(3-chloropropoxy)phenyl]-4,4-dimethyl-4,5-dihydro-1,3-oxazole ax10.
Yield: 99%.
LC-MS (MH+): 268/270.

7.3 Synthesis of 2-(4-{3-[2,5-dimethylpyrrolidin-1-yl]propoxy}phenyl)-4,4-dimethyl-4,5-dihydro-1,3-oxazole 18

2-[4-(3-chloropropoxy)phenyl]-4,4-dimethyl-4,5-dihydro-1,3-oxazole ax10 (500 mg, 1.87 mmol, 1 eq), sodium iodide (0.56 mg, 3.74 mmol, 2 eq), sodium hydrogenocarbonate (0.31 mg, 3.74 mmol, 2 eq) and 2,5-dimethylpyrrolidine (0.24 ml, 2.8 mmol, 1.5 eq) are stirred at reflux overnight in dry acetonitrile (10 ml). Water and ethyl acetate are added to the mixture and the layers are separated. The organic layer is dried with brine, sodium sulfate and evaporated in vacuum. Flash chromatography over silica with ethyl acetate as the eluent gives 0.253 g of 2-(4-{3-[2,5-dimethylpyrrolidin-1-yl]propoxy}phenyl)-4,4-dimethyl-4,5-dihydro-1,3-oxazole 18 as a free base.

Yield: 41%.

$^1$H NMR: $\delta_H$ (CDCl$_3$): 7.85 (d, 2H), 6.89 (d, 2H), 4.15-3.92 (m, 4H), 2.65-2.43 (m, 6H), 1.90 (quintet, 2H), 1.35 (s, 6H), 1.00 (t, 6H).

Synthesis of the Maleate Salt of 18

2-[4-{3-(2,5-dimethylpyrrolidin-1-yl)propoxy}phenyl)]-4,4-dimethyl-4,5-dihydro-1,3-oxazole (0.253 g, 0.76 mmol, 1 eq) is added to a solution of maleic acid (89 mg, 0.76 mmol, 1 eq) in a 95:5 mixture of ethyl acetate and ethanol. The maleate salt is recrystallised in ethyl acetate to give 0.27 g of crystals of 2-(4-{3-[2,5-dimethylpyrrolidin-1-yl]propoxy}phenyl)-4,4-dimethyl-4,5-dihydro-1,3-oxazole maleate 18.

Yield: 100%.

LC-MS (MH$^+$): 331.

Example 8

Synthesis of 1-{3-[4-(4,4-dimethyl-4,5-dihydro-1,3-thiazol-2-yl)phenoxy]propyl}piperidine 23

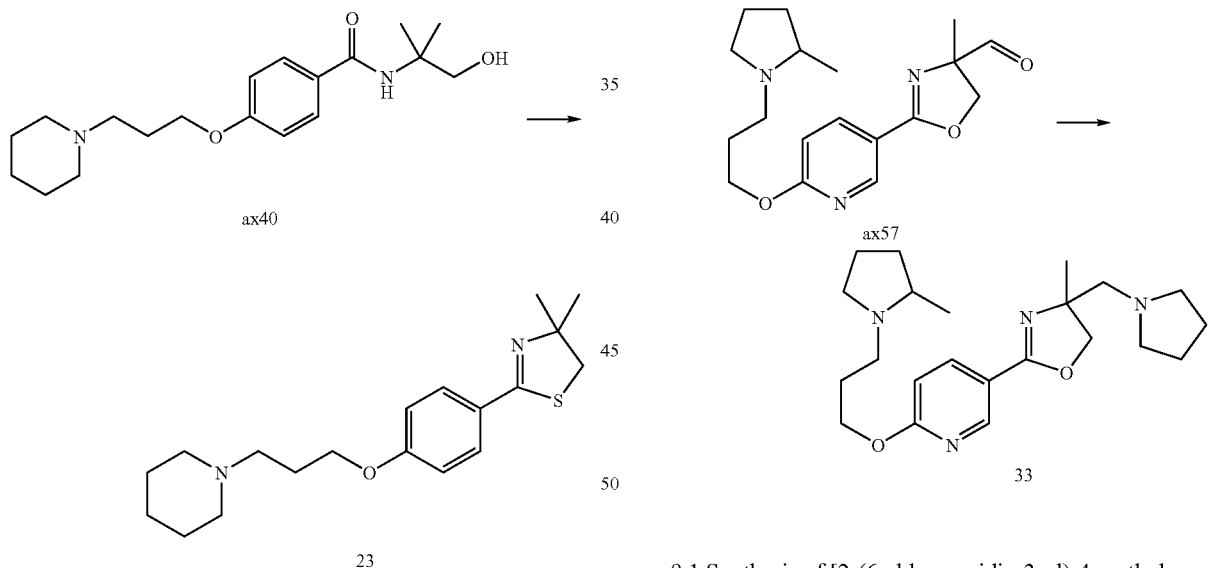

N-(2-hydroxy-1,1-dimethylethyl)-4-(3-piperidin-1-ylpropoxy)benzamiden ax40 (850 mg, 2.53 mmol) and Lawesson's reagent (1.02 g, 2.52 mmol) are suspended in toluene. The mixture is refluxed for 0.5 h. More Lawesson's reagent (100 mg, 0.25 mmol) is added and reflux is continued for 0.5 h. Upon cooling, a solid settles on the bottom. The toluene is removed and the residue is purified by chromatography over silicagel, eluting with a gradient of triethylamine in ethyl acetate, to afford 100 mg of 1-{3-[4-(4,4-dimethyl-4,5-dihydro-1,3-thiazol-2-yl)phenoxy]propyl}piperidine 23.

LC-MS (MH$^+$): 333.

Example 9

Synthesis of 5-(4-methyl-4-(pyrrolidin-1-ylmethyl)-4,5-dihydrooxazol-2-yl)-2-(3-(2-methylpyrrolidin-1-yl)propoxy)pyridine 33

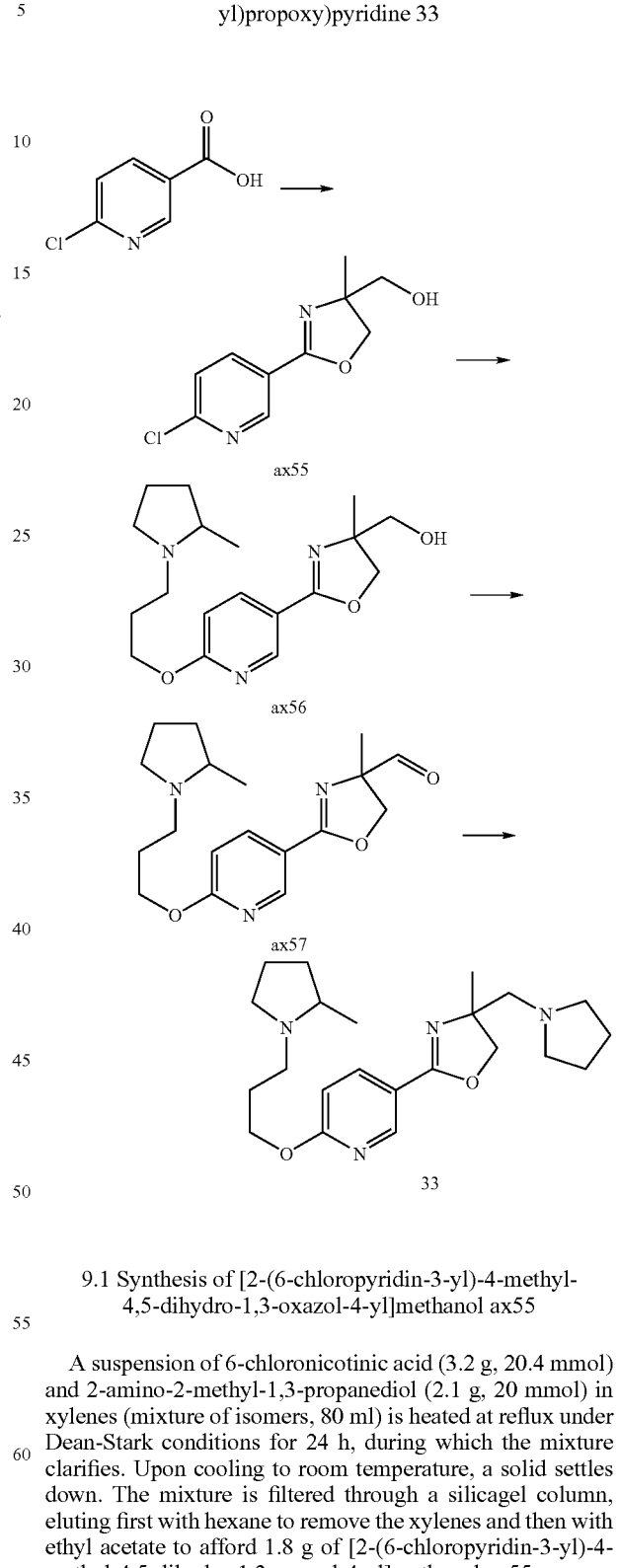

9.1 Synthesis of [2-(6-chloropyridin-3-yl)-4-methyl-4,5-dihydro-1,3-oxazol-4-yl]methanol ax55

A suspension of 6-chloronicotinic acid (3.2 g, 20.4 mmol) and 2-amino-2-methyl-1,3-propanediol (2.1 g, 20 mmol) in xylenes (mixture of isomers, 80 ml) is heated at reflux under Dean-Stark conditions for 24 h, during which the mixture clarifies. Upon cooling to room temperature, a solid settles down. The mixture is filtered through a silicagel column, eluting first with hexane to remove the xylenes and then with ethyl acetate to afford 1.8 g of [2-(6-chloropyridin-3-yl)-4-methyl-4,5-dihydro-1,3-oxazol-4-yl]methanol ax55.

Yield: 40%.

LC-MS (MH$^+$): 227.

9.2 Synthesis of (4-methyl-2-{6-[3-(2-methylpyrrolidin-1-yl)propoxy]pyridin-3-yl}-4,5-dihydro-1,3-oxazol-4-yl)methanol ax56

A solution of 3-(2-methylpyrrolidin-1-yl)propan-1-ol (1.9 g, 13.4 mmol) in dry DMF (40 ml) is treated at 0° C. with sodium hydride (60% dispersion in mineral oil, 536 mg, 13.4 mmol) and stirred 15 minutes at 0° C. Then, a solution of [2-(6-chloropyridin-3-yl)-4-methyl-4,5-dihydro-1,3-oxazol-4-yl]methanol ax55 (1.8 g, 7.9 mmol) in dry DMF (40 ml) is added dropwise over 15 minutes and the resulting mixture is stirred at room temperature for 1 day. The mixture is then poured into ice-cold water (250 ml) and extracted with ethyl acetate (4×50 ml). The organic layers are combined, dried over sodium sulfate and concentrated. The residue is dried under high-vacuum with heating to leave a solid. This solid is taken up in ethyl acetate, washed with brine and filtered. After phase separation, the aqueous layer is extracted twice with ethyl acetate, the combined organic phases are washed three times with water, dried over magnesium sulfate and concentrated to afford 1.4 g of 80% pure (4-methyl-2-{6-[3-(2-methylpyrrolidin-1-yl)propoxy]pyridin-3-yl}-4,5-dihydro-1,3-oxazol-4-yl)methanol ax56.

Yield: 40%.
LC-MS (MH$^+$): 334.

9.3 Synthesis of 4-methyl-2-{6-[3-(2-methylpyrrolidin-1-yl)propoxy]pyridin-3-yl}-4,5-dihydro-1,3-oxazole-4-carbaldehyde ax57

A solution of oxalyl chloride (0.38 ml, 4.32 mmol) in dichloromethane (30 ml) is cooled to −78° C. and is treated slowly with dimethylsulfoxide (0.51 ml, 7.2 mmol). After 20 min at −78° C., a solution of (4-methyl-2-{6-[3-(2-methylpyrrolidin-1-yl)propoxy]pyridin-3-yl}-4,5-dihydro-1,3-oxazol-4-yl)methanol ax56 (1.2 g, 80% purity, ca. 3.0 mmol) in dichloromethane (10 ml) is added dropwise over 10 min. After 60 min at −78° C., triethylamine (2.5 ml, 18 mmol) is added and the mixture is allowed to warm to 22° C. Water is then added and after vigorous stirring, the organic layer is separated and the aqueous phase extracted twice with dichloromethane. The combined organic layers are washed with brine, dried over sodium sulfate and concentrated in vacuo to yield 1.2 g of ca. 80% pure 4-methyl-2-{6-[3-(2-methylpyrrolidin-1-yl)propoxy]pyridin-3-yl}-4,5-dihydro-1,3-oxazole-4-carbaldehyde ax57.

Yield: 90%.
LC-MS (MH$^+$): 332.

9.4 Synthesis of 5-[4-methyl-4-(pyrrolidin-1-ylmethyl)-4,5-dihydro-1,3-oxazol-2-yl]-2-[3-(2-methylpyrrolidin-1-yl)propoxy]pyridine 33

A solution of 4-methyl-2-{6-[3-(2-methylpyrrolidin-1-yl)propoxy]pyridin-3-yl}-4,5-dihydro-1,3-oxazole-4-carbaldehyde ax57 (273 mg, ca. 80% pure, ca. 0.66 mmol) in dichloroethane (4 ml) is treated with pyrrolidine (0.27 ml, 3.28 mmol) and sodium triacetoxyborohydride (0.35 g, 1.64 mmol), and the turbid solution is stirred at 22° C. overnight. Fresh pyrrolidine (0.145 ml, 1.64 mmol) and sodium triacetoxyborohydride (0.35 g, 1.64 mmol) are added and the solution is stirred for an additional 2 hours at room temperature. Water is then added and the mixture stirred vigorously for 5 minutes. Extraction is performed with dichloromethane until the organic extract does not contain significant UV-active spots. The combined organic layers are dried over sodium sulfate and concentrated to yield a brown oil. The product is purified by chromatography over silicagel (eluent: gradient 10 to 20% triethylamine in 90 to 80% hexanes) to afford 66 mg of 5-[4-methyl-4-(pyrrolidin-1-ylmethyl)-4,5-dihydro-1,3-oxazol-2-yl]-2-[3-(2-methylpyrrolidin-1-yl)propoxy]pyridine 33.

Yield: 25%.
LC-MS (MH$^+$): 334.

Example 10

Synthesis of 8-benzyl-2-{4-[3-(2-methylpyrrolidin-1-yl)propoxy]phenyl}-3-oxa-1,8-diazaspiro[4.5]dec-1-ene 30, 2-{4-[3-(2-methylpyrrolidin-1-yl)propoxy]phenyl}-3-oxa-1,8-diazaspiro[4.5]dec-1-ene 36 and 8-cyclopentyl-2-{4-[3-(2-methylpyrrolidin-1-yl)propoxy]phenyl}-3-oxa-1,8-diazaspiro[4.5]dec-1-ene 32.

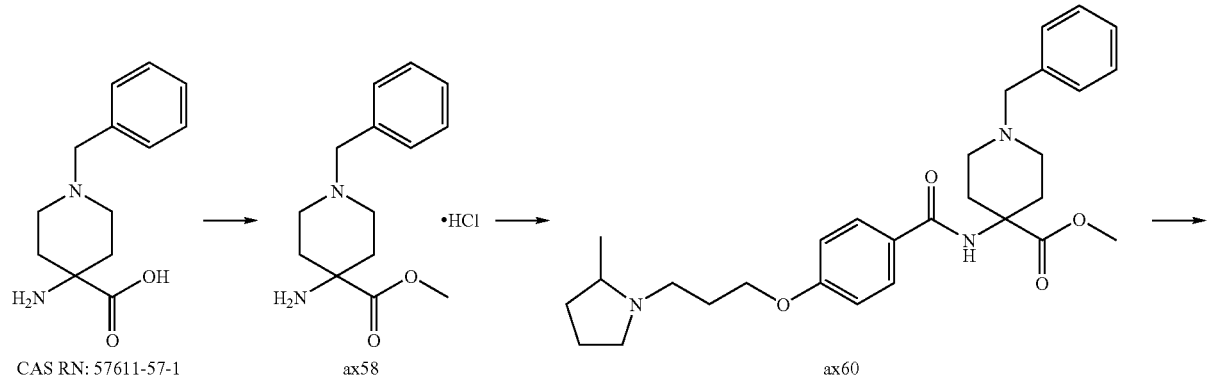

-continued

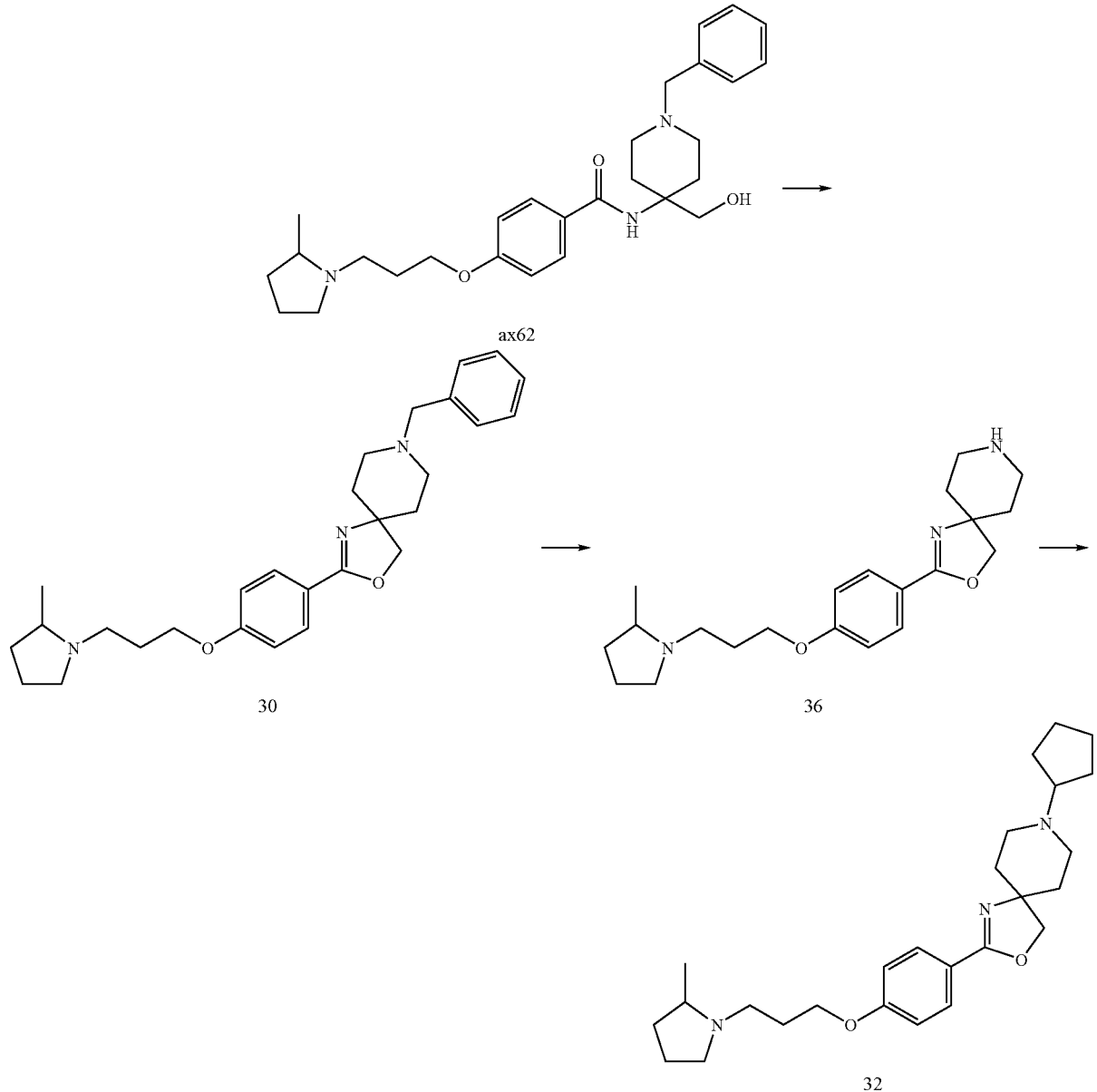

10.1 Synthesis of 4-amino-1-benzylpiperidine-4-carboxylic acid hydrochloride ax58

A solution of 4-amino-1-benzylpiperidine-4-carboxylic acid (5 g, 21 mmol) in methanol (90 ml) is cooled down to 0° C. and treated dropwise with thionyl chloride. The mixture is then brought to reflux for 5 hours and stirred at 20° C. overnight. The mixture is concentrated under reduced pressure, the residue is taken up in toluene and concentrated again to give 6.14 g of 4-amino-1-benzylpiperidine-4-carboxylic acid hydrochloride ax58 as a hygroscopic white solid.

Yield: 100%.
LC-MS (MH+): 249.

The following compound may be synthesized according to the same method:

| ax59 | methyl 3-amino-1-benzylpyrrolidine-3-carboxylate | LC-MS (MH+): 235 |

10.2 Synthesis of methyl 1-benzyl-4-({4-[3-(2-methylpyrrolidin-1-yl)propoxy]benzoyl}amino)piperidine-4-carboxylate ax60

A suspension of 4-[3-(2-methyl-1-pyrrolidinyl)propoxy] benzoic acid ax26 (0.924 g, 3.51 mmol) and methyl 4-amino-1-benzylpiperidine-4-carboxylate hydrochloride ax58 (1 g, 3.51 mmol) in dichloromethane (35 ml) is treated with triethylamine (1.46 ml, 10.53 mmol) and the mixture is cooled to 0° C. N-[3-(dimethylamino)propyl]-N'-ethylcarbodiimide hydrochloride (0.740 g, 3.86 mmol) and 1-hydroxybenzotriazole hydrate (0.09 g, 0.70 mmol) are then added, and the mixture is stirred at 22° C. overnight. The mixture is then washed two times with water, then with a saturated solution of sodium chloride. The organic layer is dried over magnesium sulfate, filtered and concentrated under reduced pressure to give 1.61 g of a yellow oil. The crude product is purified by chromatography over silicagel (eluent: dichloromethane/methanol, gradient 96/4 to 60/40) to give 1.01 g of methyl 1-benzyl-4-({4-[3-(2-methylpyrrolidin-1-yl)propoxy]benzoyl}amino)piperidine-4-carboxylate ax60 as an orange oil.

Yield: 58%.

LC-MS (MH$^+$): 494.

The following compound may be synthesized according to the same method:

| ax61 | methyl 1-benzyl-3-({4-[3-(2-methylpyrrolidin-1-yl)propoxy]benzoyl}amino)-pyrrolidine-3-carboxylate | LC-MS (MH$^+$): 480 |
| --- | --- | --- |

10.3 Synthesis of N-[1-benzyl-4-(hydroxymethyl)piperidin-4-yl]-4-[3-(2-methylpyrrolidin-1-yl)propoxy]benzamide ax62

A solution of methyl 1-benzyl-4-({4-[3-(2-methylpyrrolidin-1-yl)propoxy]benzoyl}amino)piperidine-4-carboxylate ax60 (0.93 g, 1.89 mmol) in dry tetrahydrofurane (20 ml) is cooled to 0° C. and lithium borohydride (1.4 ml, 2.83 mmol, 2 M in tetrahydrofurane) is added dropwise. The mixture is then stirred at room temperature overnight. The reaction mixture is then cooled to 0° C. and water (1.4 ml) and 1 N sodium hydroxide (1.4 ml) are added. After stirring for 20 minutes at 20° C., the mixture is concentrated and the residue is taken up in acetone (30 ml). The solution is cooled to 0° C., then 1 N hydrochloric acid (9.45 ml, 9.45 mmol) is added and the mixture is stirred at room temperature for 1 hour and concentrated to afford a pink oil. This oil is taken up in dichloromethane and treated with a saturated solution of potassium carbonate to reach pH 10. Dichloromethane is removed under reduced pressure and the aqueous phase is extracted twice with ethyl acetate. The combined organic extracts are dried over magnesium sulfate, filtered and concentrated to give 0.63 g of N-[1-benzyl-4-(hydroxymethyl)piperidin-4-yl]-4-[3-(2-methylpyrrolidin-1-yl)propoxy]benzamide ax62.

Yield: 72%.

LC-MS (MH$^+$): 466.

The following compound may be synthesized according to the same method:

| ax63 | N-[1-benzyl-3-(hydroxymethyl)pyrrolidin-3-yl]-4-[3-(2-methylpyrrolidin-1-yl)propoxy]benzamide | LC-MS (MH$^+$): 452 |
| --- | --- | --- |

10.4 Synthesis of 8-benzyl-2-{4-[3-(2-methylpyrrolidin-1-yl)propoxy]phenyl}-3-oxa-1,8-diazaspiro[4.5]dec-1-ene 30.

A solution of N-[1-benzyl-4-(hydroxymethyl)piperidin-4-yl]-4-[3-(2-methylpyrrolidin-1-yl)propoxy]benzamide ax62 (0.46 g, 0.98 mmol) in dichloromethane (10 ml) is cooled at 0° C. and diethylaminosulfur trifluoride (180 µl, 1.47 mmol) is added. After stirring at 20° C. for 1.5 hours, the reaction mixture is cooled to 0° C. and another portion of diethylaminosulfur trifluoride (40 µl, 0.33 mmol) is added. This is repeated once more with another portion of 20 µl. Potassium carbonate (0.203 g, 1.47 mmol) is then added to the mixture, which is stirred at room temperature for 30 minutes. The mixture is then washed with a saturated solution of sodium bicarbonate, and the aqueous layer is extracted again with dichloromethane. The combined organic extracts are dried over magnesium sulfate, filtered and concentrated under reduced pressure to give 0.453 g of an orange oil, which is purified by chromatography over silicagel (dichloromethane/methanol/ammonia 94:5.4:0.6) to give 0.17 g of 8-benzyl-2-{4-[3-(2-methylpyrrolidin-1-yl)propoxy]phenyl}-3-oxa-1,8-diazaspiro[4.5]dec-1-ene 30.

Yield: 38%.

LC-MS (MH$^+$): 448.

10.5 Synthesis of 2-{4-[3-(2-methylpyrrolidin-1-yl)propoxy]phenyl}-3-oxa-1,8-diazaspiro[4.5]dec-1-ene 36.

A suspension of 8-benzyl-2-{4-[3-(2-methylpyrrolidin-1-yl)propoxy]phenyl}-3-oxa-1,8-diazaspiro[4.5]dec-1-ene 30 (0.22 g, 0.49 mmol) and palladium hydroxide (0.02 g, 10% wt) in ethanol (10 ml) is placed in a Parr apparatus under a hydrogen atmosphere (40 psi) overnight. After this time, palladium hydroxide (0.02 g, 10% wt) is added again, and the mixture is stirred further under hydrogen at 50° C. for 2 days. The mixture is then filtered on celite and the filtrate is concentrated under reduced pressure to give 0.22 g of 2-{4-[3-(2-methylpyrrolidin-1-yl)propoxy]phenyl}-3-oxa-1,8-diazaspiro[4.5]dec-1-ene 36 as a paste.

Yield: 100%.

LC-MS (MH$^+$): 258.

10.6 Synthesis of 8-cyclopentyl-2-{4-[3-(2-methylpyrrolidin-1-yl)propoxy]phenyl}-3-oxa-1,8-diazaspiro[4.5]dec-1-ene 32.

A solution of 2-{4-[3-(2-methyl-1-pyrrolidinyl)propoxy]phenyl}-3-oxa-1,8-diazaspiro[4.5]dec-1-ene 36 (0.11 g, 0.245 mmol) in acetonitrile (4 ml) is placed under an argon atmosphere. Bromocyclopentane (0.039 ml, 0.368 mmol, 1.5 eq), potassium carbonate (0.068 g, 0.49 mmol, 2 eq) and potassium iodide (0.08 g, 0.05 mmol, 0.2 eq) are added and the mixture is stirred at 50° C. overnight. The mixture is then filtered and the filtrate is concentrated under reduced pressure, taken up in dichloromethane, and washed twice with a saturated aqueous solution of ammonium chloride. The aqueous phases are extracted with dichloromethane and the organic extracts are collected together and dried over magnesium sulfate. Dichloromethane is removed under reduced pressure to give 0.086 g of yellow oil. This crude product is purified by chromatography over silica gel (eluent: dichloromethane/ethanol/ammonia 89:10.9:0.1) to afford 0.034 g of 8-cyclopentyl-2-{4-[3-(2-methylpyrrolidin-1-yl)propoxy]phenyl}-3-oxa-1,8-diazaspiro[4.5]dec-1-ene 32.

Yield: 33%.

LC-MS (MH$^+$): 426.

Example 11

Synthesis of 2-[4-(1-methyl-3-piperidin-1-ylpropoxy)phenyl]-3-oxa-1-azaspiro[4.5]dec-1-ene 37.

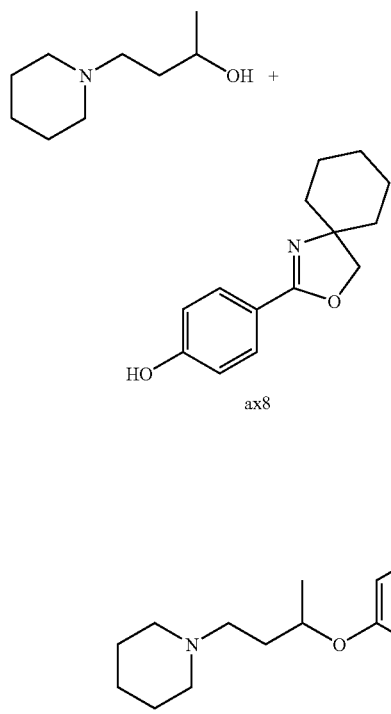

Example 12

Synthesis of 2-[4-(2-methyl-3-piperidin-1-ylpropoxy)phenyl]-3-oxa-β-azaspiro[4.5]dec-1-ene 38.

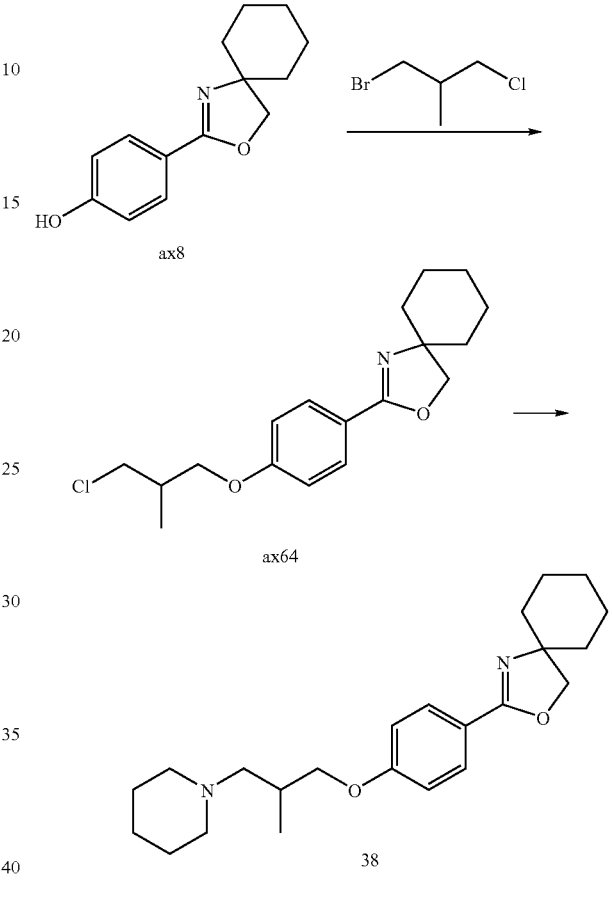

To a solution of triphenylphosphine (1.03 g, 3.92 mmol, 1.1 eq) in tetrahydrofuran (10 ml) at 0° C. is added dropwise diisopropylazodicarboxylate (0.776 ml, 3.92 mmol, 1.1 eq). The mixture is stirred for 5 minutes and 4-(1-piperidinyl)-2-butanol (0.56 g, 3.56 mmol, 1 eq) is added slowly. Then, a solution of 4-(3-oxa-1-azaspiro[4.5]dec-1-en-2-yl)phenol ax8 (0.82 g, 3.56 mmol, 1 eq) in tetrahydrofuran (5 ml) is added at 0° C. The mixture is allowed to warm at room temperature and stirred for 2 hours. It is then poured into 0.5 N hydrochloric acid and extracted with diethyl ether. The aqueous layer is treated with a 1 M aqueous solution of sodium hydroxide to reach pH 9 and extracted 3 times with diethyl ether. The combined organic layers are dried over magnesium sulfate and the solvent is removed under reduced pressure to give 1.18 g of an orange oil. The crude product is purified by chromatography over silica gel to give 0.41 g of 2-[4-(1-methyl-3-piperidin-1-ylpropoxy)phenyl]-3-oxa-1-azaspiro[4.5]dec-1-ene 37 as a yellow oil.

Yield: 31%.

LC-MS (MH$^+$): 371.

12.1 Synthesis of 2-[4-(3-chloro-2-methylpropoxy)phenyl]-3-oxa-1-azaspiro[4.5]dec-1-ene ax64.

To a solution of 4-(3-oxa-1-azaspiro[4.5]dec-1-en-2-yl)phenol ax8 (0.5 g, 2.16 mmol, 1 eq) in acetone (30 ml) is added 1-bromo-3-chloro-2-methylpropane (0.25 ml, 2.16 mmol, 1 eq) and potassium carbonate (0.6 g, 4.32 mmol, 2 eq). The mixture is stirred at reflux for 13 days. The mixture is concentrated, taken up in dichloromethane and washed twice with a saturated aqueous solution of ammonium chloride. The organic layer is dried over magnesium sulfate and the solvent is removed under reduced pressure to afford 0.7 g of 2-[4-(3-chloro-2-methylpropoxy)phenyl]-3-oxa-1-azaspiro[4.5]dec-1-ene ax64 as a colorless oil. This crude product is used in the next step without further purification.

Yield: 100%.

LC-MS (MH$^+$): 322/324.

12.2 Synthesis of 2-[4-(2-methyl-3-piperidin-1-ylpropoxy)phenyl]-3-oxa-1-azaspiro[4.5]dec-1-ene 38.

A solution of 2-[4-(3-chloro-2-methylpropoxy)phenyl]-3-oxa-1-azaspiro[4.5]dec-1-ene ax64 (0.35 g, 1.1 mmol, 1 eq) in acetonitrile (20 ml) is treated with potassium carbonate (0.3 g, 2.2 mmol, 2 eq), sodium iodide (0.01 g, 0.073 mmol, 0.07 eq) and piperidine (0.52 ml, 5.2 mmol, 4.7 eq), and the mixture is stirred at reflux for 5 days. After this time, the mixture is concentrated, taken up in ethyl acetate and washed with water. The organic layer is dried over magnesium sulfate and concentrated to dryness to give 0.36 g of a yellow oil. This crude product is purified by flash chromatography over silica gel (eluent: dichloromethane/methanol/ammonia 96:3.6:0.4) to give 0.13 g of 2-[4-(2-methyl-3-piperidin-1-ylpropoxy)phenyl]-3-oxa-1-azaspiro[4.5]dec-1-ene 38 as a colorless oil.

Yield: 40%.

LC-MS (MH+): 371.

Table I gives characteristics of some compounds of general formula (I). Said table indicates the stereochemical information in the columns headed "configuration": the second one indicates whether a compound has no stereogenic center (achiral), is a pure enantiomer (pure), a racemate (rac) or is a mixture of two stereoisomers, possibly in unequal proportions (mixture); the first one contains the stereochemical assignment for the recognized center, following the IUPAC numbering used in the "IUPAC name" column. A number alone indicates the existence of both configurations at that center. A number followed by 'R' or 'S' indicates the known absolute configuration at that center. Table 1 indicates also the type and stoichiometry of salt, which was synthesized (if not the free base), the IUPAC name of the compound, the ion peak observed in mass spectrometry, the $^1$H NMR description and the optical rotation in the case of enantiomerically pure compounds.

TABLE I

| n° | Salt | Configuration | IUPAC Name | MH+ (M+•) | $^1$H NMR (solvent) $\delta_H$(ppm) | AlphaD |
|---|---|---|---|---|---|---|
| 1 |  | achiral | 1-{3-[4,4,4-dimethyl-4,5-dihydro-1,3-oxazol-2-yl)phenoxy]propyl}piperidine | 317 | (CDCl$_3$): 1.37 (s, 6H), 1.61 (m, 4H), 2.00 (m, 3H), 2.43 (s, 4H), 2.50 (m, 2H), 4.05 (m, 4H), 6.89 (d, 8.80 Hz, 2H), 7.86 (d, 8.80 Hz, 2H) |  |
| 2 | 2 maleate |  | achiral | 1-{3-[4(4,4-dimethyl-4,5-dihydro-1,3-oxazol-2-yl)phenoxy]propyl}-4-isopropylpiperazine | 360 | (DMSO): 1.2 (d, 6H), 1.3 (s, 6H), 2.0 (p, 2H), 3.2-2.6 (m, 10H), 3.3 (h, 1H), 4.09-3.95 (m, 4H), 6.63 (s, 4H), 7.0 (d, 2H), 7.78 (d, 2H) |  |
| 3 |  | achiral | 1-{3-[4-(4,4-dimethyl-4,5-dihydro-1,3-oxazol-2-yl)phenoxy]propyl}-4-isopropylpiperazine | 360 | (CDCl$_3$): 1.05 (m, 6H), 1.39 (m, 6H), 1.98 (m, 2H), 2.52 (m, 11H), 4.05 (m, 4H), 6.89 (d, 8.80 Hz, 2H), 7.86 (m, 2H) |  |
| 4 |  | 3,5-cis (75%) 3,5-trans (25%) | achiral | 1-{3-[4-(4,4-dimethyl-4,5-dihydro-1,3-oxazol-2-yl)phenoxy]propyl}-3,5-dimethylpiperidine | 345 | (CDCl$_3$): 1.42 (m, 25H), 2.78 (m, 2H), 3.98 (m, 4H), 6.82 (m, 2H), 7.78 (m, 2H) |  |
| 5 |  | 2 | rac | 4,4-dimethyl-2-{3-[3-(2-methylpyrrolidin-1-yl)propoxy]phenyl}-4,5-dihydro-1,3-oxazole | 317 | (CDCl$_3$): 1.14 (m, 3H), 1.37 (m, 6H), 1.99 (m, 10H), 3.05 (m, 1H), 3.27 (m, 1H), 4.09 (m, 4H), 7.00 (m, 1H), 7.29 (m, 1H), 7.49 (m, 2H) |  |
| 6 |  | 4S,5R | pure | 1-(3-{4-[(4S,5R)-4-methyl-5-phenyl-4,5-dihydro-1,3-oxazol-2-yl]phenoxy}propyl)piperidine | 379 | (CDCl$_3$): 1.47 (d, 10.49 Hz, 5H), 1.59 (s, 4H), 1.77 (m, 1H), 1.99 (m, 2H), 2.43 (m, 6H), 4.06 (t, 10.25 Hz, 2H), 5.06 (d, 12.44 Hz, 1H), 6.93 (d, 14.40 Hz, 2H), 7.36 (d, 1.71 Hz, 5H), 7.94 (d, 14.15 Hz, 2H) | +25.54 |
| 7 |  |  | achiral | 2-[4-(3-piperidin-1-ylpropoxy)phenyl]-3-oxa-1-azaspiro[4.5]dec-1-ene | 357 | (CDCl$_3$): 1.55 (m, 16H), 1.98 (m, 2H), 2.39 (s, 4H), 2.46 (m, 2H), 4.03 (t, 6.41 Hz, 2H), 4.11 (s, 2H), 6.88 (d, 8.80 Hz, 2H), 7.85 (d, 9.05 Hz, 2H) |  |
| 8 |  |  | achiral | 2-[3-(3-piperidin-1-ylpropoxy)phenyl]-3-oxa-1-azaspiro[4.5]dec-1-ene | 357 | (CDCl$_3$): 1.60 (m, 20H), 2.33 (m, 4H), 2.50 (m, 2H), 4.03 (m, 2H), 4.11 (m, 2H), 6.99 (dd, 8.05 and 2.39 Hz, 1H), 7.28 (m, 1H), 7.47 (m, 2H) |  |
| 9 |  | 4R | pure | 1-(3-{4-[(4R)-4-benzyl-4,5-dihydro-1,3-oxazol-2-yl]phenoxy}propyl)piperidine | 379 | (CDCl$_3$): 1.44 (d, 4.53 Hz, 2H), 1.59 (m, 3H), 1.85 (s, 1H), 1.98 (m, 2H), 2.44 (m, 6H), 2.71 (dd, 13.58, 8.93 Hz, 1H), 3.24 (dd, 13.83, 4.90 Hz, 1H), 4.08 (m, 3H), 4.31 (t, 8.80 Hz, 1H), 4.55 (dd, 7.29, 5.28 Hz, 1H), 6.90 (d, 8.55 Hz, 2H), 7.27 (m, 5H), 7.87 (d, 8.80 Hz, 2H) | −36.47 |
| 10 |  |  | achiral | 2-[4-(3-pyrrolidin-1-ylpropoxy)phenyl]-3-oxa-1-azaspiro[4.5]dec-1-ene | 343 | (CDCl$_3$): 1.65 (m, 16H), 2.53 (m, 4H), 2.62 (m, 2H), 4.08 (m, 4H), 6.89 (d, 8.80 Hz, 2H), 7.85 (m, 2H) |  |
| 11 |  | 2 | rac | 2-{4-[3-(2-methylpiperidin-1-yl)propoxy]phenyl}-3-oxa-1-azaspiro[4.5]dec-1-ene | 371 | (CDCl$_3$): 1.07 (d, 6.04 Hz, 3H), 1.31 (m, 5H), 1.62 (d, 9.81 Hz, 7H), 1.78 (m, 4H), 1.96 (m, 2H), 2.18 (m, 1H), 2.31 (s, 1H), 2.50 (m, 1H), 2.88 (m, 2H), 4.02 (d, 2.77 Hz, 2H), 4.11 (s, 2H), 6.88 (d, 8.80 Hz, 2H), 7.86 (d, 8.55 Hz, 2H) |  |
| 12 |  |  | achiral | 2-[3-(3-pyrrolidin-1-ylpropoxy)phenyl]-3-oxa-1-azaspiro[4.5]dec-1-ene | 343 | (CDCl$_3$): 1.30 (m, 4H), 1.61 (m, 2 H), 1.80 (m, 8H), 2.01 (m, 3H), 2.54 (s, 4H), 2.63 (m, 2H), 4.07 (s, 2H), 4.13 (s, 2H), 6.99 (m, 1H), 7.47 (m, 1H), 7.50 (d, 7.55 Hz, 1H) |  |

TABLE I-continued

| n° | Salt | Configuration | | IUPAC Name | MH+ (M+•) | 1H NMR (solvent) δH(ppm) | AlphaD |
|---|---|---|---|---|---|---|---|
| 13 | | 2 | rac | 4,4-dimethyl-2-{4-[3-(2-methylpyrrolidin-1-yl)propoxy]phenyl}-4,5-dihydro-1,3-oxazole | 317 | (CDCl3): 1.08 (d, 6.06 Hz, 3H), 1.37 (s, 7H), 2.00 (m, 9H), 3.07 (m, 2H), 4.07 (m, 4H), 6.88 (m, 2H), 7.86 (m, 2H) | |
| 14 | 1 maleate | 2 | rac | 5-(4,4-dimethyl-4,5-dihydro-1,3-oxazol-2-yl)-2-[3-(2-methylpyrrolidin-1-yl)propoxy]pyridine | 318 | (DMSO): 1.31 (m, 9H), 1.60 (m, 1H), 2.05 (dd, 6.57, 6.57, 5.05 & 0.76 Hz, 5H), 3.10 (d, 8.34 Hz, 2H), 3.62 (d, 1.26 Hz, 1H), 4.10 (s, 2H), 4.40 (d, 5.56 Hz, 2H), 6.02 (s, 2H), 6.91 (d, 8.59 Hz, 1H), 8.11 (dd, 8.59, 2.40 Hz, 1H), 8.59 (d, 1.77 Hz, 1H) | |
| 15 | | 2R | pure | 4,4-dimethyl-2-(4-{3-[(2R)-2-methylpyrrolidin-1-yl]propoxy}phenyl)-4,5-dihydro-1,3-oxazole | 317 | (CDCl3): 1.09 (d, 6.29 Hz, 3H), 1.37 (s, 6H), 2.02 (m, 10H), 2.98 (m, 1H), 3.18 (td, 8.80, 2.58 Hz, 1H), 4.06 (m, 4H), 6.90 (m, 2H), 7.86 (d, 9.05 Hz, 2H) | −51.14 |
| 16 | | 2 | rac | 2-{6-[3-(2-methylpyrrolidin-1-yl)propoxy]pyridin-3-yl}-3-oxa-1-azaspiro[4.5]dec-1-ene | 358 | (CDCl3): 1.09 (d, 6.06 Hz, 3H), 1.35 (m, 5H), 1.97 (m, 14H), 2.97 (m, 1H), 3.18 (d, 1.77 Hz, 1H), 4.12 (s, 2H), 4.40 (m, 2H), 6.72 (d, 8.59 Hz, 1H), 8.10 (dd, 8.84, 2.40 Hz, 1H), 8.65 (d, 1.77 Hz, 1H) | |
| 17 | | | achiral | 1-{3-[3-bromo-4-(4,4-dimethyl-4,5-dihydro-1,3-oxazol-2-yl)phenoxy]propyl}piperidine | 395/397 | (CDCl3): 1.42 (m, 8H), 1.59 (m, 4H), 1.96 (m, 2H), 2.43 (m, 6H), 4.01 (s, 2H), 4.10 (s, 2H), 6.84 (dd, 8.55, 2.52 Hz, 1H), 7.15 (d, 2.52 Hz, 1H), 7.60 (d, 8.80 Hz, 1H) | |
| 18 | 1 maleate | 2,5 | pure cis | 2-(4-{3-[2,5-dimethylpyrrolidin-1-yl]propoxy}phenyl)-4,4-dimethyl-4,5-dihydro-1,3-oxazole | 331 | (DMSO): 1.32 (m, 14H), 1.61 (s, 2H), 2.12 (m, 5H), 4.11 (m, 4H), 6.04 (s, 3H), 7.03 (d, 8.80 Hz, 2H), 7.81 (d, 8.80 Hz, 2H) | |
| 19 | | 3 | rac | 1-{3-[4-(4,4-dimethyl-4,5-dihydro-1,3-oxazol-2-yl)phenoxy]propyl}-N,N-dimethylpyrrolidin-3-amine | 346 | | |
| 20 | | 4 | rac | 1-(3-{4-[4-(piperidin-1-ylmethyl)-4,5-dihydro-1,3-oxazol-2-yl]phenoxy}propyl)piperidine | 386 | (CDCl3): 1.57 (m, 8H), 1.98 (m, 3H), 2.59 (m, 12H), 4.04 (t, 6.29 Hz, 2H), 4.20 (m, 1H), 4.43 (m, 2 H), 6.91 (m, 2H), 7.89 (m, 2H) | |
| 21 | | 4 | rac | 1-(3-{4-[4-(pyrrolidin-1-ylmethyl)-4,5-dihydro-1,3-oxazol-2-yl]phenoxy}propyl)piperidine | 372 | (CDCl3): 1.58 (m, 4H), 1.78 (s, 4H), 1.98 (m, 2H), 2.53 (m, 12H), 2.79 (m, 1H), 4.04 (t, 6.29 Hz, 2H), 4.22 (t, 7.67 Hz, 1H), 4.43 (m, 2H), 6.89 (m, 2H), 7.86 (m, 2H) | |
| 22 | | 4 | rac | 1-(3-{4-[4-(2-pyrrolidin-1-ylethyl)-4,5-dihydro-1,3-oxazol-2-yl]phenoxy}propyl)piperidine | 365 | (CDCl3): 1.73 (m, 16H), 2.54 (m, 12H), 4.04 (m, 3H), 4.30 (m, 1H), 4.48 (m, 1H), 6.90 (d, 8.80 Hz, 2H), 7.86 (m, 2H) | |
| 23 | | 4,2,6 | mixture | 1-[3-(4-{4-[(3,5-dimethylisoxazol-4-yl)methyl]-4-methyl-4,5-dihydro-1,3-oxazol-2-yl}phenoxy)propyl]-2,6-dimethylpiperidine | 440 | (CDCl3): 7.65 (d, 2H), 6.80 (d, 2H), 3.95 (t, 2H), 3.10 (s, 2H), 2.2-2.5 (m, 6H), 1.9 (p, 2H), 1.5 (m, 4H), 1.4 (m, 2H), 1.3 (s, 6H) | |
| 24 | | | achiral | 5-[4-(3-piperidin-1-ylpropoxy)phenyl]-6-oxa-4-azaspiro[2.4]hept-4-ene | 315 | (CDCl3): 0.78 (m, 3H), 1.24 (m, 6H), 1.59 (m, 5H), 1.98 (m, 3H), 2.45 (m, 6H), 4.04 (t, 6.41 Hz, 2H), 4.38 (s, 2H), 6.89 (d, 8.80 Hz, 2H), 7.84 (d, 8.80 Hz, 2H) | |
| 25 | | 4S,2 | mixture | (4S)-4-tert-butyl-2-{4-[3-(2-methylpyrrolidin-1-yl)propoxy]phenyl}-4,5-dihydro-1,3-oxazole | 345 | (CDCl3): 0.72 (s, 9 H), 0.88 (d, 6.04 Hz, 3H), 1.65 (m, 9H), 2.76 (m, 1H), 2.97 (m, 1H), 3.80 (m, 3H), 3.98 (m, 1H), 4.08 (m, 1H), 6.67 (d, 8.80 Hz, 2H), 7.65 (d, 8.80 Hz, 2H) | |
| 26 | | 3aR,7aR,2 | mixture | (3aR,7aR)-2-{4-[3-(2-methylpyrrolidin-1-yl)propoxy]phenyl}-3a,4,5,6,7,7a-hexahydro-1,3-benzoxazole | 343 | (DMSO): 1.38 (m, 21H), 4.07 (m, 3H), 4.65 (m, 1H), 6.97 (d, 9.04 Hz, 2H), 7.77 (d, 8.79 Hz, 2H) | |
| 27 | | 4S,2 | mixture | (4S)-2-{4-[3-(2-methylpyrrolidin-1-yl)propoxy]phenyl}-(4S)-phenyl-4,5-dihydro-1,3-oxazole | 365 | (CDCl3): 1.11 (s, 3H), 1.89 (m, 10H), 3.10 (m, 2H), 4.17 (m, 3H), 4.76 (s, 1H), 5.35 (s, 1H), 6.94 (s, 2H), 7.97 (s, 2H) | |
| 28 | | 4S,2 | mixture | (4S)-4-(cyclohexylmethyl)-2-{4-[3-(2-methylpyrrolidin-1-yl)propoxy]phenyl}-4,5-dihydro-1,3-oxazole | 385 | (CDCl3): 1.63 (m, 25H), 2.97 (d, 11.80 Hz, 1H), 3.17 (d, 2.01 Hz, 1H), 3.95 (t, 7.79 Hz, 1H), 4.06 (m, 2H), 4.32 (m, 1H), 4.46 (m, 1H), 6.90 (d, 8.79 Hz, 2H), 7.86 (d, 8.79 Hz, 2H) | |

TABLE I-continued

| n° | Salt | Configuration | IUPAC Name | MH+ (M+•) | $^1$H NMR (solvent) $\delta_H$(ppm) | AlphaD |
|---|---|---|---|---|---|---|
| 29 | | achiral | 2-[4-(3-piperidin-1-ylpropoxy)phenyl]-1-oxa-3-azaspiro[4.5]dec-2-ene | 357 | (CDCl$_3$): 1.28 (m, 1H), 1.48 (m, 6H), 1.59 (m, 6H), 1.80 (m, 4H), 1.98 (m, 2H), 2.40 (s, 4H), 2.47 (m, 2H), 3.70 (s, 2H), 4.04 (t, 6.41 Hz, 2H), 6.90 (m, 2H), 7.86 (m, 2H) | |
| 30 | | 2 | rac | 8-benzyl-2-{4-[3-(2-methylpyrrolidin-1-yl)propoxy]phenyl}-3-oxa-1,8-diazaspiro[4.5]dec-1-ene | 448 | (CDCl$_3$): 1.09 (m, 3H), 1.43 (m, 1H), 1.74 (m, 5H), 1.94 (m, 6H), 2.11 (m, 1H), 2.24 (m, 4H), 2.83 (m, 2H), 2.97 (m, 1H), 3.17 (m, 1H), 3.55 (m, 2H), 4.06 (m, 2H), 4.11 (m, 2H), 6.89 (m, 2H), 7.26 (m, 2H), 7.32 (m, 4H), 7.86 (m, 2H) | |
| 31 | | 5,2 | mixture | 7-benzyl-2-{4-[3-(2-methylpyrrolidin-1-yl)propoxy]phenyl}-3-oxa-1,7-diazaspiro[4.4]non-1-ene | 434 | (CDCl$_3$): 1.08 (d, 6.04 Hz, 3H), 1.42 (m, 1H), 1.75 (m, 3H), 1.95 (m, 4H), 2.12 (q, 8.80 Hz, 1H), 2.20 (m, 1H), 2.30 (m, 2H), 2.64 (m, 2H), 2.73 (m, 1H), 2.93 (m, 2H), 3.17 (m, 1H), 3.65 (m, 2H), 4.05 (m, 2H), 4.20 (d, 8.55 Hz, 1H), 4.37 (d, 8.55 Hz, 1H), 6.89 (d, 8.80 Hz, 2H), 7.29 (m, 6H), 7.85 (d, 8.80 Hz, 2H) | |
| 32 | | 2 | rac | 8-cyclopentyl-2-{4-[3-(2-methylpyrrolidin-1-yl)propoxy]phenyl}-3-oxa-1,8-diazaspiro[4.5]dec-1-ene | 426 | (CDCl$_3$): 1.01 (d, 6.04 Hz, 3H), 1.78 (m, 23H), 2.47 (m, 1H), 2.86 (m, 3H), 3.10 (m, 1H), 4.00 (m, 4H), 6.82 (d, 8.80 Hz, 2H), 7.79 (d, 8.55 Hz, 2H) | |
| 33 | | 2,4 | mixture | 5-[4-methyl-4-(pyrrolidin-1-ylmethyl)-4,5-dihydro-1,3-oxazol-2-yl]-2-[3-(2-methylpyrrolidin-1-yl)propoxy]pyridine | 334 | (CDCl$_3$): 1.0 (d, 3H), 1.3 (s, 3H), 1.3-2.5 (m, 17H), 2.55 (d, 1H), 2.65 (d, 1H), 2.90 (m, 1H), 3.2 (m, 1H), 3.95 (d, 1H), 4.3 (t, 2H), 4.35 (d, 1H), 6.70 (d, 1H), 8.0 (dd, 1H), 8.60 (d, 1H) | |
| 34 | | 2,4 | mixture | 5-[4-methyl-4-(piperidin-1-ylmethyl)-4,5-dihydro-1,3-oxazol-2-yl]-2-[3-(2-methylpyrrolidin-1-yl)propoxy]pyridine | 401 | (CDCl$_3$): 1.09 (d, 5.78 Hz, 3H), 1.40 (m, 9H), 2.28 (m, 14H), 2.96 (m, 3H), 3.19 (s, 1H), 3.99 (d, 7.79 Hz, 1H), 4.39 (m, 3H), 6.72 (d, 8.54 Hz, 1H), 8.07 (dd, 8.79 Hz, 2.13 Hz, 1H), 8.65 (d, 1.51 Hz, 1H) | |
| 35 | | 2,4 | mixture | 1-[(4-methyl-2-{6-[3-(2-methylpyrrolidin-1-yl)propoxy]pyridin-3-yl}-4,5-dihydro-1,3-oxazol-4-yl)methyl]azepane | 415 | (CDCl$_3$): 1.0 (d, 3H), 1.3 (s, 3H), 1.3-2.5 (m, 21H), 2.45 (d, 1H), 2.75 (d, 1H), 2.90 (m, 1H), 3.2 (m, 1H), 3.9 (d, 1H), 4.3 (t, 2H), 4.35 (d, 1H), 6.70 (d, 1H), 8.0 (dd, 1H), 8.6 (d, 1H) | |
| 36 | | 2 | rac | 2-{4-[3-(2-methylpyrrolidin-1-yl)propoxy]phenyl}-3-oxa-1,8-diazaspiro[4.5]dec-1-ene | 358 | (DMSO): 0.98 (d, 6.03 Hz, 3H), 1.26 (m, 2H), 1.66 (m, 6H), 1.87 (m, 3H), 2.04 (d, 8.79 Hz, 1H), 2.12 (m, 1H), 2.25 (m, 1H), 2.62 (s, 2H), 2.77 (d, 8.29 Hz, 1H), 2.90 (m, 1H), 3.07 (m, 3H), 4.06 (t, 6.28 Hz, 2H), 4.15 (s, 1H), 6.99 (d, 8.79 Hz, 2H), 7.78 (m, 2H) | |
| 37 | | 1 | rac | 2-[4-(1-methyl-3-piperidin-1-ylpropoxy)phenyl]-3-oxa-1-azaspiro[4.5]dec-1-ene | 371 | (CDCl$_3$): 1.37 (m, 8H), 1.59 (m, 7H), 1.77 (m, 5H), 1.92 (m, 1H), 2.37 (m, 6H), 4.11 (s, 2H), 4.50 (d, 6.28 Hz, 1H), 6.89 (d, 8.79 Hz, 2H), 7.84 (d, 8.79 Hz, 2H) | |
| 38 | | 2 | rac | 2-[4-(2-methyl-3-piperidin-1-ylpropoxy)phenyl]-3-oxa-1-azaspiro[4.5]dec-1-ene | 371 | (CDCl$_3$): 1.04 (d, 6.28 Hz, 3H), 1.37 (m, 6H), 1.59 (m, 5H), 1.78 (m, 5H), 2.16 (d, 8.29 Hz, 2H), 2.35 (m, 5H), 3.78 (dd, 8.79, 6.66 Hz, 1H), 4.05 (dd, 9.29, 4.14 Hz, 1H), 4.11 (s, 2H), 6.91 (d, 8.79 Hz, 2H), 7.85 (d, 8.54 Hz, 2H) | |

Example 13

Affinity for the Histamine H$_3$-Receptor

Inverse Agonism, Antagonism and Agonism Activity: [$^{35}$S]GTPγS-Binding Assay Human Histaine H$_3$-Receptor Material and Methods Reagents Reagents and reference compounds were of analytical grade and obtained from various commercial sources. [$^3$H]-N-α-methylhistamine (80-85 Ci/mmol) and [$^{35}$S]-GTPγS (1250 Ci/mmol) were purchased from Perkin Elmer (Belgium). Cell culture reagents were purchased from Cambrex (Belgium).

Test and reference compounds were dissolved in 100% DMSO to give a 1 mM stock solution. Final DMSO concentration in the assay did not exceed 1%.

A CHO cell line expressing the human H$_3$ histamine receptor (sequence as published by Lovenberg et al. in Mol. Pharmacol. 1999, Mol. Pharmacol., 55, 1101-1107) was purchased from Euroscreen S.A. (Belgium).

Cell Culture

Cells were grown in HAM-F12 culture media containing 10% fetal bovine serum, 100 IU/ml penicillin, 100 µg/ml streptomycin, 1% sodium pyruvate and 400 µg/ml of gentamycin. Cells were maintained at 37° C. in a humidified atmosphere composed of 95% air and 5% $CO_2$.

Membrane Preparation

Confluent cells were detached by 10 min incubation at 37° C. in PBS/EDTA 0.02%. The cell suspension was centrifuged at 1,500×g for 10 min at 4° C. The pellet was homogenized in a 15 mM Tris-HCl buffer (pH 7.5) containing 2 nM $MgCl_2$, 0.3 mM EDTA, 1 mM EGTA (buffer A). The crude homogenate was frozen in liquid nitrogen and thawed. DNAse (1 µl/ml) was then added and the homogenate was further incubated for 10 min at 25° C. before being centrifuged at 40,000×g for 25 min at 4° C. The pellet was resuspended in buffer A and washed once more under the same conditions. The final membrane pellet was resuspended, at a protein concentration of 1-3 mg/ml, in a 7.5 mM Tris-HCl buffer (pH 7.5) enriched with 12.5 mM $MgCl_2$, 0.3 mM EDTA, 1 mM EGTA and 250 mM sucrose and stored in liquid nitrogen until used.

Binding Assays

[$^3$H]—N-α-methylhistamine Binding Assay

Affinity of compounds for human $H_3$ histamine receptors was measured by competition with [$^3$H]-N-α-methylhistamine. This binding assay was performed essentially as described by Lovenberg et al. (Mol. Pharmacol. 1999, Mol. Pharmacol., 55, 1101-1107) and Tedford et al. (J. Pharmacol. Exper. Ther., 1999, 289, 1160-1168) with minor modifications. Briefly, membranes (20-40 µg proteins) expressing human $H_3$ histamine receptors were incubated at 25° C. in 0.5 ml of a 50 mM Tris-HCl buffer (pH 7.4) containing 2 mM $MgCl_2$, 0.2 nM [$^3$H]-N-α-methylhistamine and increasing concentrations of drugs. The non specific binding (NSB) was defined as the residual binding observed in the presence of 10 µM thioperamide or histamine. Membrane-bound and free radioligand were separated by rapid filtration through glass fiber filters presoaked in 0.1% PEI. Samples and filters were rinsed by at least 6 ml of ice-cold 50 mM Tris-HCl buffer (pH 7.4). The entire filtration procedure did not exceed 10 seconds per sample. Radioactivity trapped onto the filters was counted by liquid scintillation in a β-counter.

[$^{35}$S]-GTPγS Binding Assay

Stimulation (agonist) or inhibition (inverse agonist) of [$^{35}$S]-GTPγS binding to membrane expressing human $H_3$ histamine receptors was measured as described by Lorenzen et al. (Mol. Pharmacol. 1993, 44, 115-123) with a few modifications. Briefly, membranes (10-20 µg proteins) expressing human $H_3$ histamine receptors were incubated at 25° C. in 0.2 ml of a 50 mM Tris-HCl buffer (pH 7.4) containing 3 mM $MgCl_2$, 50 mM NaCl, 1 µM GDP, 2 µg saponin and increasing concentrations of drugs. After 15 min preincubation, 0.2 nM of [$^{35}$S]-GTPγS were added to the samples. The non specific binding (NSB) was defined as the residual binding observed in the presence of 100 µM Gpp(NH)$_p$. Membrane-bound and free radioligand were separated by rapid filtration through glass fiber filters. Samples and filters were rinsed by at least 6 ml of ice-cold 50 mM Tris-HCl buffer (pH 7.4). The entire filtration procedure did not exceed 10 seconds per sample. Radioactivity trapped onto the filters was counted by liquid scintillation in a β-counter.

Data Analysis

Determination of $pIC_{50}/pKi/pEC_{50}/pEC_{50}INV$

Analysis

Raw data are analyzed by non-linear regression using XLfit™ (IDBS, United Kingdom) according to the following generic equation $$B = MIN + [(MAX-MIN)/(1+(((10^X)/(10^{-pX50}))^{nH}))]$$

where:

B is the radioligand bound in the presence of the unlabelled compound (dpm),

MIN is the minimal binding observed (dpm)

MAX is maximal binding observed (dpm),

X is the concentration of unlabelled compound (log M), $pX_{50}$ (−log M) is the concentration of unlabelled compound causing 50% of its maximal effect (inhibition or stimulation of radioligand binding). It stands for pIC50 when determining the affinity of a compound for the receptor in binding studies with [$^3$H]-N-α-methylhistamine, for $pEC_{50}$ for compounds stimulating the binding of [$^{35}$S]-GTPγS (agonists) and for $pEC_{50}INV$ for compounds inhibiting the binding of [$^{35}$S]-GTPγS (inverse agonists).

$n_H$ is the Hill coefficient.

pKi is obtained by applying the following equation (Cheng and Prusoff, 1973, Biochem. Pharmacol., 22: 3099-3108):

$$pKi = pIC_{50} + \log(1+L/Kd)$$

where:

pKi is the unlabelled compound equilibrium dissociation constant (−log M),

L is the radioligand concentration (nM),

Kd is the radioligand equilibrium dissociation constant (nM).

Compounds of formula (I) according to the invention showed $pIC_{50}$ values ranging from 6.5 to 10 for the histamine $H_3$-receptor.

Compounds of formula (I) according to the invention showed $pEC_{50}INV$ values typically ranging from 6.5 to 10 for the histamine $H_3$-receptor.

Example 14

Antagonism Activity

Paced Isolated Guinea Pig Myenteric Plexus—Electric-Field Stimulation Assay

Material and Methods

Reagents

Stock solutions ($10^{-2}$ M) and further dilutions were freshly prepared in DMSO (WNR, Leuven, Belgium). All other reagents (R(−)-α-methylhistamine, mepyramine, ranitidine, propranolol, yohimbine and components of the Krebs' solution) were of analytical grade and obtained from conventional commercial sources.

Animals

Four week-old male Dunkin-Hartley guinea pigs (200-300 g) were supplied by Charles River (Sultfeld, Germany). All animals were ordered and used under protocol "orgisol-GP" approved by the UCB Pharma ethical committee. Animals were housed in the UCB animal facility in groups of 12, in stainless steel cages (75×50×30 cm) and allowed to acclimatise for a minimum of one week before inclusion in the study. Room temperature was maintained between 20 and 24° C. with 40 to 70% relative humidity. A light and dark cycle of 12 h was applied. Animals had free access to food and water.

Organ Preparation

The method was adapted from that described by Menkveld et al. in Eur. J. Pharmacol. 1990, 186, 343-347. Longitudinal myenteric plexus was prepared from the isolated guinea pig ileum. Tissues were mounted in 20-ml organ baths containing modified Krebs' solution with $10^{-7}$ M mepyramine, $10^{-5}$ M ranitidine, $10^{-5}$ M propranolol and $10^{-6}$ M yohimbine. The bathing solution was maintained at 37° C. and gassed with 95% $O_2$-5% $CO_2$. Tissues were allowed to equilibrate for a 60-min period under a resting tension of 0.5 g and an electrical field stimulation (pulses of 5-20 V, 1 ms and 0.1 Hz was applied during the whole experiment). Such a stimulation induces stable and reproductive twitch contractions. Isometric contractions were measured by force-displacement transducers coupled to an amplifier connected to a computer system (EMKA Technologies) capable of controlling (i) automatic data acquisition, (ii) bath washout by automatic fluid circulation through electrovalves at predetermined times or signal stability and (iii) automatic dilution/injection of drug in the bath at predetermined times or signal stability.

Protocol

After a 60 min-stabilisation period, tissues were stimulated twice with $10^{-6}$ M R(-)-α-methylhistamine at 30-min interval. After a 60-min incubation period in the presence of solvent or antagonist test compound, a cumulative concentration-response to R(-)-α-methylhistamine was elicited ($10^{-10}$ à 10 M). Only one concentration of antagonist was tested on each tissue.

Data Analysis

An appropriate estimate of interactions between agonist and antagonist can be made by studying the family of curves observed in the absence or presence of increasing antagonist concentrations. The value of each relevant parameter of each concentration-response curve ($pD_2$ and $E_{max}$) was calculated by an iterative computer software (XLfit, IDBS, Guildford, UK) fitting the experimental data to the four parameter logistic equation. Antagonistic activity of the test substance was estimated by the calculation of $pD'_2$ and/or $pA_2$ values according to the methods described by Van Rossum et al. in Arch. Int. Pharmacodyn. Ther. 1963, 143, 299 and/or by Arunlakshana & Schild in Br. J. Pharmacol. 1959, 14, 48.

Results are expressed as the mean±SD. The number of observations is indicated as n. Compounds of formula (I) according to the invention showed $pA_2$ values typically greater than 6.5 for the histamine $H_3$-receptor.

The invention claimed is:

1. A compound, geometrical isomer, enantiomer, diastereoisomer, pharmaceutically acceptable salt or mixture thereof of formula I,

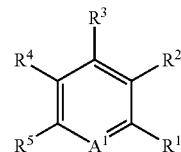

(I)

wherein
$A^1$ is CH or N;
$R^1$ is hydrogen;
$R^2$ is

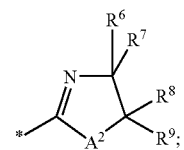

(II)

$A^2$ is O;
$R^3$ is hydrogen;
$R^4$ is hydrogen;
$R^5$ is —O—$(CH_2)_m$—$NR^{13a}R^{13b}$;
$R^6$ is hydrogen or methyl; or $R^6$ and $R^7$ are linked together to form a $C_5$ alkylene, one methylene of the alkylene being optionally replaced by a nitrogen atom, said nitrogen atom being optionally substituted by a cyclopentyl or a benzyl group;
$R^7$ is methyl, piperidin-1-ylmethyl or pyrrolidin-lylmethyl; or $R^6$ and $R^7$ are linked together to form a $C_5$ alkylene, one methylene of the alkylene being optionally replaced by a nitrogen atom, said nitrogen atom being optionally substituted by a cyclopentyl or a benzyl group;
$R^8$ is hydrogen;
$R^9$ is hydrogen;
—$NR^{13a}R^{13b}$ is selected from the group consisting of 1-piperidinyl and 2-methylpyrrolidin-1-yl; and
m is an integer equal to 3.

2. A compound according to claim 1 selected from the group consisting of
1-{3-[4-(4,4-dimethyl-4,5-dihydro-1,3-oxazol-2-yl)phenoxy]propyl}piperidine;
4,4-dimethyl-2-{3-[3-(2-methylpyrrolidin-1-yl)propoxy]phenyl}-4,5-dihydro-1,3-oxazole;
2-[4-(3-piperidin-1-ylpropoxy)phenyl]-3-oxa-1-azaspiro[4.5]dec-1-ene;
2-[3-(3-piperidin-1-ylpropoxy)phenyl]-3-oxa-1-azaspiro[4.5]dec-1-ene;
1-(3-{4-[(4R)-4-benzyl-4,5-dihydro-1,3-oxazol-2-yl]phenoxy}propyl)piperidine;
4,4-dimethyl-2-{4-[3-(2-methylpyrrolidin-1-yl)propoxy]phenyl}-4,5-dihydro-1,3-oxazole;
5-(4,4-dimethyl-4,5-dihydro-1,3-oxazol-2-yl)-2-[3-(2-methylpyrrolidin-1-yl)propoxy]pyridine;
4,4-dimethyl-2-(4-{3-[(2R)-2-methylpyrrolidin-1-yl]propoxy}phenyl)-4,5-dihydro-1,3-oxazole;

2-{6-[3-(2-methylpyrrolidin-1-yl)propoxy]pyridin-3-yl}-3-oxa-1-azaspiro[4.5]dec-1-ene;

1-{3-[4-(4,4-dimethyl-4,5-dihydro-1,3-oxazol-2-yl)phenoxy]propyl}-N,N-dimethylpyrrolidin-3-amine;

1-(3-{4-[4-(pyrrolidin-1-ylmethyl)-4,5-dihydro-1,3-oxazol-2-yl]phenoxy}propyl)piperidine;

1-(3-{4-[4-(2-pyrrolidin-1-ylethyl)-4,5-dihydro-1,3-oxazol-2-yl]phenoxy}propyl)piperidine;

8-benzyl-2-{4-[3-(2-methylpyrrolidin-1-yl)propoxy]phenyl}-3-oxa-1,8-diazaspiro[4.5]dec-1-ene;

7-benzyl-2-{4-[3-(2-methylpyrrolidin-1-yl)propoxy]phenyl}-3-oxa-1,7-diazaspiro[4.4]non-1-ene;

8-cyclopentyl-2-{4-[3-(2-methylpyrrolidin-1-yl)propoxy]phenyl}-3-oxa-1,8-diazaspiro[4.5]dec-1-ene;

5-[4-methyl-4-(pyrrolidin-1-ylmethyl)-4,5-dihydro-1,3-oxazol-2-yl]-2-[3-(2-methylpyrrolidin-1-yl)propoxy]pyridine;

5-[4-methyl-4-(piperidin-1-ylmethyl)-4,5-dihydro-1,3-oxazol-2-yl]-2-[3-(2-methylpyrrolidin-1-yl)propoxy]pyridine;

2-{4-[3-(2-methylpyrrolidin-1-yl)propoxy]phenyl}-3-oxa-1,8-diazaspiro[4.5]dec-1-ene; and 2-[4-(1-methyl-3-piperidin-1-ylpropoxy)phenyl]-3-oxa-1-azaspiro[4.5]dec-1-ene.

3. A pharmaceutical composition comprising an effective amount of a compound according to claim 1, or a pharmaceutically acceptable salt thereof in combination with a pharmaceutically acceptable diluent or carrier.

* * * * *